(12) United States Patent
Bourland et al.

(10) Patent No.: US 6,201,988 B1
(45) Date of Patent: Mar. 13, 2001

(54) RADIOTHERAPY TREATMENT USING MEDICAL AXIS TRANSFORMATION

(75) Inventors: J. Daniel Bourland, Winston-Salem, NC (US); Oing R. Wu, Westlake, OH (US)

(73) Assignee: Wake Forest University Baptist Medical Center, Winston-Salem, NC (US)

( * ) Notice: Subject to any disclaimer, the term of this patent is extended or adjusted under 35 U.S.C. 154(b) by 0 days.

(21) Appl. No.: 09/117,992
(22) PCT Filed: Feb. 7, 1997
(86) PCT No.: PCT/US97/02105
§ 371 Date: Nov. 12, 1998
§ 102(e) Date: Nov. 12, 1998
(87) PCT Pub. No.: WO97/28845
PCT Pub. Date: Aug. 14, 1997

Related U.S. Application Data
(60) Provisional application No. 60/011,451, filed on Feb. 9, 1996.

(51) Int. Cl.[7] .................................................. A61B 5/05
(52) U.S. Cl. ............................................. 600/427; 378/65
(58) Field of Search .................................... 600/427, 407, 600/425, 428; 378/62, 64, 65; 128/920

(56) References Cited

U.S. PATENT DOCUMENTS

| | | | |
|---|---|---|---|
| 5,418,715 | 5/1995 | Deasy .................................. | 364/413 |
| 5,754,622 | * 5/1998 | Hughes ................................. | 378/65 |
| 5,754,623 | * 5/1998 | Seki ..................................... | 378/65 |
| 6,032,066 | * 2/2000 | Lu et al. .............................. | 600/407 |

OTHER PUBLICATIONS

Zhu, Y., et al., "Accuracy Requirements of the Primary X–ray Spectrum in Dose Calculations Using FFT Convolution Techniques", *2389 Medical Physics; No. 4*, 421–426, (Apr. 22, 1995).

* cited by examiner

*Primary Examiner*—Brian L. Casler
(74) *Attorney, Agent, or Firm*—Schwegman, Lundberg, Woessner & Kluth, P.A.

(57) ABSTRACT

The medial axis analysis of an object can be used to effectively guide and optimize radiosurgery treatment planning. In this method, a fast Euclidean medial axis transformation in three dimensions based on dynamic grassfire simulation and ridge extraction is presented. A ridge occurs when fire fronts collapse during grassfire propagation. Iso-contours(2D) or iso-surfaces(3D) can be obtained from dynamic grassfire transforms. They are locally smooth everywhere except at ridge locations. Ridges are detected by measuring local curvature at each point. This process is invariant under spatial translations and rotations. In radiosurgery treatment planning, optimal shots are only placed on the medial axis of the 3D target, which reduces optimization time and complexity.

20 Claims, 7 Drawing Sheets

RADIOTHERAPY TREATMENT USING MEDICAL AXIS TRANSFORMATION

The application claims benefit to provisional application Ser. No. 60/011,451 Feb. 9, 1996.

BACKGROUND OF THE INVENTION

1. Field of the Invention

The present invention relates to methods for guiding radiation treatments of animals, especially human patients. The present invention is particularly related to methods for guiding the distribution of radiation in medical radiotherapy processes which generate spherical doses of radiation or, more properly, approximately spherical distributions of radiation.

2. Background of the Art

Tumors of the brain are regarded as special candidates for precision conformal radiotherapy. Historically the term "radiosurgery," introduced by Leksell (Leksell, L. 1951, "The Stereotactic Method and Radiosurgery of the Brain," Acta Chir Scand 102:316–319), was used to describe the method by which many narrow radiation beams were used to irradiate intracranial structures from many angels as an alternative to surgery. The Leksell 201 source[60] Co Gamma Knife®[†] used for such radiosurgery, is shown in FIG. 1 (and as with OUR Scientific International, Inc., New York, N.Y., "Rotating Gamma System"). These 201 sources are contained in an upper hemispherical shield. All sources are focused to a single point at a source-to-focus distance of 403 mm. The central beam is at an angle of 55° to the horizontal plane. The sources lie in an arc of ±48 about this central ray in the long axis of the treatment unit and at an arc ±80° along the transverse axis to the patient couch. The final precise collimation is achieved by selection of one of four interchangeable collimator helmets with 201 channels aligning with the sources that produce 4, 8, 14, or 18 mm diameter fields at the focus (Wu, A. 1992, "Physics and Dosimetry of the Gamma Knife," Neurosurgery Clinics of North America, Vol. 3(1):35–50). A stereotactic frame is attached to the patient under local anesthesia and then the frame is positioned into the collimating channel so that the tumor to be treated is at the focal point of the beams.

Treatment planning optimization for radiation therapy, including, but not limited to gamma knife radiosurgery, linear accelerator treatment (either modified or specifically designed for radiosurgery), Brachy treatment (where radiation dose distributions are supplied by small sealed radiation sources, called seeds), and like processes which seek to distribute radiation over bulk (volumetric versus surface area) portions of a patient, as in the treatment of tumors, benign growths, malignant growths, etc., is aimed at maximizing the dose to the target volume while minimizing the dose to adjacent normal tissues. Since radiation deposits energy all along its pathway, treatment planning optimization is a constrained optimization problem, i.e., primarily comprised of two competing limitations on the dose: 1) maximization for the targets, and 2) minimization for the normal tissues. The index of the dose given to a particular area as compared to the target dose which has been determined or established is referred to as homogeneity. In the target areas, the homogeneity is desirably between 100 to 50%. The area around the target area is the penumbra or shadow region of the exposure, and receives a dose measured as homogeneity usually in the range of 50% to 30% of the 100% of the target dose. The percent dose is measured relative to the dose at the focus of the radiation equipment. Percent dose is relative to dose at the focus. The target dose and the dose at the focus are preselected by the operator according to the specific radiation therapy intended by the equipment.

It has been observed that multiple shot treatment may deteriorate both penumbra and homogeneity compared with single shot treatment. This is due to overlap of adjacent shots and the less than optimal shot weights. Pla et al. (Pla, C. Podgorsak, E. B., Pla, M., Souhami, L., Clark, B. G., and Carson, L. J., 1995, "Considerations on the use of Multiple Isocenters in Stereotactic Radiosurgery," Med Phys, Vol. 22, No. 5:765) recently discussed the problem but did not provide any useful solution. Mathematically, the optimization process can be represented as $$P(N, S_1(d, x), \ldots, S_N(d, x)) = P_N(R) \mid N = \min(n),$$

$$\bigcup_{i=1}^{n} S_i(d, x) \approx V(R),$$

where N is the number of shots being used, $S_i$ is the ith shot, and d and x are the shot size and position, respectively. Thus, the number of shots and the position and size of each shot have to be included as parameters for the optimization, and must be optimized simultaneously. Clearly, the irregularity and size of a target volume greatly influence the number of shots needed and the sized of the shots being used to optimize the treatment.

SUMMARY OF THE INVENTION

The present invention describes a method and apparatus for improving the performance of radiotherapy procedures where doses of radiation to a bulk or three-dimensional target are desired, and where a spherical shot or individual dose of radiation is applied by the apparatus or procedure used in the treatment process. The process generally involves the examination (mapping, non-invasive image capturing, as by X-ray, NMR, sonogram, etc.) of a bulk target for radiation therapy, the determination of target lines representing the loci of spheres which, when distributed with various sizes along said target line, fill the bulk target efficiently, without extending areas strongly dosed by radiation greatly outside the bulk target, determining a level of radiation which is therapeutically effective when directed into volumes of the bulk target which are to be therapeutically treated, determining a distribution of shots or doses of radiation which can be directed at said bulk target such that radiation within each shot or dose which exceeds a preselected percentage of said level of radiation which is therapeutically effective by more than a fixed percentage of each dose or shot (e.g., no more than 80%, preferably no more than 65%, more preferably no more than 50%, and most preferably no more than 40%) of said radiation which is therapeutically effective, is not directed at areas outside of said bulk target.

In this invention, a novel method is introduced to solve this special optimization problem. The approach is to determine the configuration of shots according to the shape of the target. This automated procedure mimics manual planning and is logical, since for targets of identical volumes yet different shapes, small shots have to be used for complicated contours while large shots are suitable for regular shapes. In this new method, the medial axis transformation (skeletonization) is used to characterize the target shape and to determine the shot parameters (i.e., position, collimator size and weight). In this scheme, only skeleton points are considered for potential shot positions, and the corresponding shot size is provided by the skeletonization. Hence, the optimization in 3D is reduced to a 1D optimization problem with savings in computational time and mathematical complexity. The relationship between skeleton discs and the dose distributions they predict are discussed and the results of optimal planning and the corresponding dose distributions are presented.

DETAILED DESCRIPTION OF THE INVENTION

Figure 1:
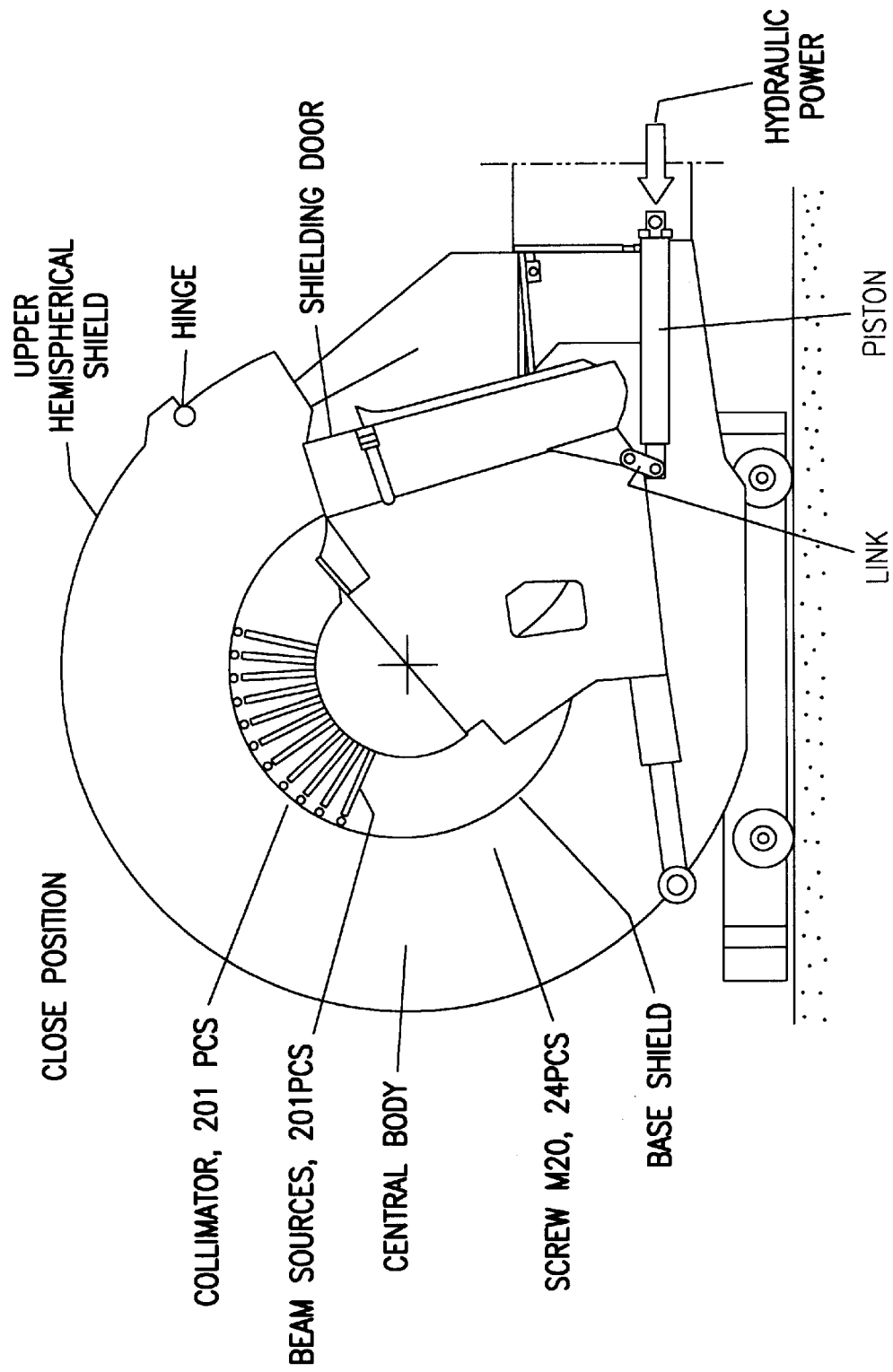
FIG. 1 shows a diagram of a Gamma Knife® apparatus for providing spherical doses of gamma radiation in medical therapy.

The method of the invention may be described as a method for planning and executing radiotherapy treatment comprising the steps of:

a) locating a medial axis of a first target region of a patient;

b) initializing a plan for the distribution of a plurality of spherical distributions of radiation by identifying endpoints of the medial axis and determining a virtual shot for each endpoint of each plan;

c) providing additional virtual shots for each plan by excluding portions of said target region which are already covered by any virtual shot which has already been determined;

d) determining a medial axis for a modified target region which is established by excluding regions from said first target region which would be covered by any virtual shot which has already been determined;

e) placing additional virtual shots at endpoints or cross points of said medial axis for said modified target region to generate a distribution plan for targeting shots of radiation.

The method is preferably performed by repeating steps c), d) and e), particularly until a therapeutically acceptable portion of said first target region is covered by virtual shots. This level of exposure is, of course, determined by proper medical evaluation. Each virtual shot should have a virtual size which is determined as dimensions for each virtual shot. The dimensions or diameters (assuming a circular or spherical shape to the dose) of the dose levels are estimated at a focal plain by determining the loci of points along which the dose level decreases from a predetermined percentage of a dose level (e.g., the maximum dose level within each shot or the optimum dose level for treatment) which exists within said virtual shot. This dose level can be called a standard or normalized dose level, and can be arbitrarily chosen from within the bounds of therapeutically desirable and effective doses (e.g., too high a dose would be effective, but not desirable). The normalized dose level which exists within said virtual shot is assigned a value (e.g., arbitrarily assigned a value of 1, 100 etc.) for normalizing or rationalizing comparisons), and said predetermined percentage which determines the perimeter of a shot is chosen to be less than a selected percentage of a therapeutically effective dose or the maximum dose within a shot. For example, the predetermined percentage may be less than 80%, less than 65% and greater than 25%, 65% and greater than 40%, or any specific range predetermined by the radiotherapist and operator. The dose and parameters are selected by the designers of the treatment procedure, choosing the dose for the prescription and the normalization point. The dose level (for each shot) tends to be about at the 50% for prescription, with the normalization point usually identified as the maximum dose within the dose distribution.

The distribution plan is used to direct a radiation emitting device or radiation implanting procedure which can be used to provide a spherical distribution of radiation to position actual distributions of radiation according to said distribution plan. The radiation emitting device may be selected, for example, from gamma emitting devices, linear accelerators, and Brachy therapy sources. The distribution plan may distribute radiation at a therapeutically effective dose level over at least 85% of said first target region. The preferred effective dose level is often selected as at least about 30%, at least about 40%, or at least about 50 or at least about 60% of the highest single dose radiation level within any shot.

The method of the invention alternatively may be described as a method for planning and executing radiotherapy treatment comprising the steps of:

a) taking a non-invasive pictorial representation of a first target region of a volume portion of a patient which is to be treated by radiation therapy;

b) locating a medial axis within the pictorial representation of the first target region of the patient;

c) calculating from said pictorial representation a plan for the distribution of a plurality of spherical distributions of radiation by identifying endpoints of the medial axis and determining a virtual shot for each endpoint of each plan, said virtual shot at each endpoint having its outer limits defined by a percentage of a therapeutically effective level of radiation which is provided in said virtual shot, the outer limits of each virtual shot extending to at least two edges of the target region, said virtual shots at the endpoints virtually covering a part of the volume portion of the patient, and leaving a virtual untreated portion of said volume where minimally desired therapeutic levels of radiation have not yet been applied, the volume of said target area where minimally desired therapeutic levels of radiation have not yet been applied by virtual shots at the endpoints defining a modified target area;

d) providing additional virtual shots for each plan within said virtual untreated portion of said volume by determining a second or modified medial axis for the modified target region which has been established;

e) placing additional virtual shots at endpoints or cross points of said modified medial axis for said modified target region to generate a distribution plan for targeting shots of radiation comprising both the virtual shots at the endpoints of the medial axis and the virtual shots placed on said modified medial axis.

The method is preferably performed by repeating steps c), d) and e), particularly until a therapeutically acceptable portion of said first target region is covered by virtual shots.

As is well known, if spheres of equal dimensions are used to pack a volume (as would equal size and dose spherical dose distributions of radiation in treating a bulk target), the spheres would fill about 53% percent of the volume and leave about 47% of the volume unfilled. This would not be an effective radiation treatment, leaving significant areas untreated if doses did not overlap, and providing potentially excessive levels of radiation over significant areas if the spheres were targeted to overlap. By the use of the present invention, distributions of spherical radiation doses may be calculated and administered which will properly dose a bulk target with effective radiation levels over at least 60% of the volume, more preferably over 70% of the volume, still more preferably over 75% of the volume, and most preferably over 80% or even over 90% of the volume of the target.

The doses provided during radiotherapy have been referred to as spherical distributions of doses or radiation. This is the theoretic objective of the apparatus or techniques used to apply the radiation, but the actual shape of the dose may vary from true sphericity. As is well understood in the art, the shape of the shot may be nearly spherical in its distribution of radiation, but may also have egg-shaped, ovoid, oblate, ellipse shapes, or other distributions of radiation which are not actually spheres. All of these distributions are conveniently called spherical in the practice of the present invention as the precise shape of the radiation distribution within a shot can be or is considered in the shot distribution calculation. Shots may have distributions of radiation in which a central portion of the shot has a regular gradation of radiation drop-off from the center of the spot to a surrounding portion of the shot, and then a less regular drop-off so that there is a spherical distribution of radiation within the center and an irregular or non-spherical distribution of radiation outside of the spherical center portion.

Figure 2:
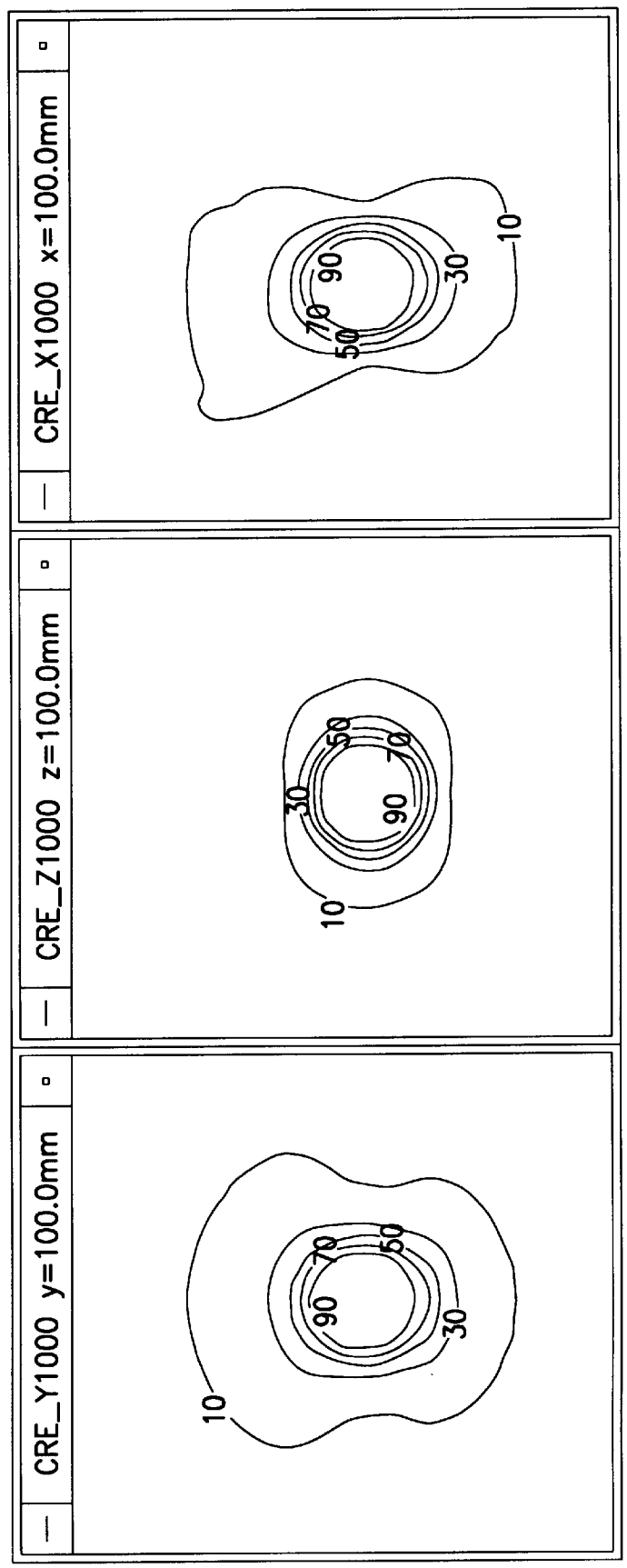
FIG. 2 shows the pictorial representation of the dose distribution in three central planes of a single shot with an 18 mm collimator.

In practical treatment planning, the size of each shot is defined as the diameter of the 50% isodose level (ISL), which is determined by the collimator size and relative weighting. FIG. 2 shows the dose distributions along three central planes for a single shot with the 18 mm collimator. The high dose levels are confined to a small spherical region, and the surrounding region exhibits very limited dose. For larger or irregular target shapes, multiple shots are used to cover different parts of the target region. In such multiple shot plans, each shot's size is determined by the physical collimator diameter and the relative weight. The weight of a shot in a multi-shot plan indicates the amount of dose contributed relative to a single shot plan of the same collimator diameter. Recent work (Wu, Q. R., 1996, "Treatment Planning Optimization for Gamma Knife® Radiosurgery," Ph.D. thesis, Mayo Foundation/Mayo Graduate School, Rochester, Minn.) shows that in order to preserve dose homogeneity and penumbra in a multi-shot plan, shot diameters should be prohibited from overlapping with each other and from protruding outside the target region, and shot weight should be in the range of 0.7 to 1.0. Overlapping shots can destroy the desired dose homogeneity inside the target. Shots protruding outside the target will result in excessive dose to surrounding normal tissues (Pla, C. Podgorsak, E. B., Pla, M., Souhami, L., Clark, B. G., and Carson, L. J., 1995, "Considerations on the use of Multiple Isocenters in Stereotactic Radiosurgery," Med. Phys, Vol. 22, No. 5:765; Wu, Q. R., 1996, "Treatment Planning Optimization for Gamma Knife® Radiosurgery," Ph.D. thesis, Mayo Foundation/Mayo Graduate School, Rochester, Minn.). A significant disadvantage of the low weight shot is that it enlarges the effective local penumbra (Pla, C. Podgorsak, E. B., Pla, M., Souhami, L., Clark, B. G., and Carson, L. J., 1995, "Considerations on the use of Multiple Isocenters in Stereotactic Radiosurgery," Med Phys, Vol. 22, No. 5:765; Wu, Q. R., 1996, "Treatment Planning Optimization for Gamma Knife® Radiosurgery," Ph.D. thesis, Mayo Foundation/Mayo Graduate School, Rochester, Minn.). When using the term "overlapping" in the description of shots, the term means that in viewing the shots as distributions of radiation intensities (e.g., similar to a Gaussian distribution), the shot diameters as represented in the distribution curves, overlap or intersect other shot distribution curves at an intensity level (e.g., the 50% isodose level or surface). It is within the skill and treatment selection parameters of the radiotherapist and operator to select more or less overlap than the traditional 50% level (e.g., ½ bandwidth).

In this study, each shot is modeled as a sphere with a diameter equal to the average range of the 50% ISL in 3D. Consider that target R is a bounded region with a certain volume and surface. Each shot $S^{d_i}(x_i)$ centered at $x_i$ with diameter $d_i$ will cover a volume $V(S^{d_i}(x_i))$. Then the treatment planning optimization can be formulated as:

$$\min N \mid P_N(R), \forall S^{d_i}(x_i) \subset R, \qquad (1)$$

$$\text{with:} \quad \frac{V(R) - V\left[\bigcup_{i=1}^{N} S^{d_i}(x_i)\right]}{V(R)} \leq \epsilon$$

where $\epsilon$ is a tolerance for the uncovered region. Since exact geometric coverage of a region with circles (2D) or spheres (3D) without overlapping requires an infinite number of different size circles (spheres), the fractional volume not covered cannot equal zero. This tolerance is both necessary as well as reasonable for clinical practice. The dose distribution of a shot can be considered as a point spread function with monotonically decreasing tails. Thus, while gap regions are defined as geometrically uncovered regions, sufficient dose may be delivered to these regions by the summation of the lower doses (<50%) from the "tails" of nearby multiple shots.

Equation (1) states that the optimal plan should (1) cover the entire region to within the tolerance $\epsilon$; (2) use the least possible number of shots and, (3) confine all the shots inside the target without overlapping. In the limit of exact conformation to the target, a plan would use the smallest possible shots all the time. Given an irregularly shaped target, small shots can better match the external boundary and the gap between shots is smaller. However, that will result in extremely long treatment times. Hence the number of shots being used has to be included as an optimization parameter.

Figure 3A:
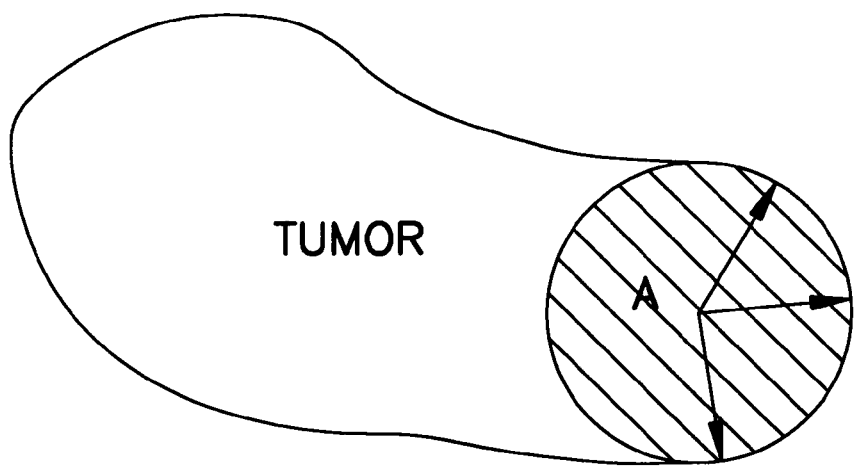
FIG. 3 shows (a) an ideally matched shot and (b) shot size/position which is less than ideal.

To optimize both homogeneity and penumbra, the best arrangement for an individual shot is that it just touches the target boundary, as shown in FIG. 3(a). For arranging shots in such optimal fashion, the character of a target's shape is used, as represented by a function called the medial axis transformation (Blum, H. 1972, "Biological Shape and Visual Science: Part I," J. of Theoretical Biology, Vol 38, 205–287; Blum, H., Nagel, R. 1978, "Shape Description Using Weighted Symmetric Axis Features," *Pattern Recognition,* Vol. 10, 167–180). This use of target shape is an automated version of the manual treatment planning process, where shot sizes and positions are purposefully selected to "match" as a specific part of a target. The medial axis transformation, or skeletonization, of a region, is its symmetric axis (or medial axis) and it describes an object's inherent characteristics of shape and symmetry. The symmetrical properties of both the skeleton and dose from a shot make the skeletonization applicable to treatment planning optimization. The key assumption is this: if the geometry of a shot and a part of the target match, then the dose distribution is optimal for this part of the region. Indeed, matching of a shot diameter with the target contour is observed during the manual treatment planning process. We use a fast 3D medial axis transform (Wu, Q. R., Bourland, J. D., Robb, R. A., 1996, "Fast 3D Medial Axis Transform to Reduce Complexity and Computation for Radiosurgery Treatment Planning," has been presented at SPIE Medical Imaging 96) technique to automate and optimize the manual method.

There are a number of methods within the practice of the present invention which are useful in the generation of the skeleton determinations for use with the methodology of the present invention. Numerous algorithms have been developed for computing a skeleton from a given discrete figure. For binary objects, they generally fall into one of the following three categories:

1) Approximation of a firefront propagation;
2) Approximation of continuous skeletons directly from the boundaries: and
3) Extraction and linking of centers of maximal disks or approximate medial points (e.g., ridge points) in the distance map of the original object.

The first category algorithms follow the grassfire anology. A grassfire, simulated by a connected set of boundary points, is started at the figure boundary and propagated to the figure's interior. Skeletons are then obtained by detecting points where two firefronts meet. This method is also called morphological or topological thinning. Algorithms iteratively peel off border pixels that are not needed for preserving connectivity. Active contour models are also in this category. To simulate firefront propagation, an active contour starts from the object boundary and moves at unit speed toward the interior of the object based on a Euclidian distance map.

The second category algorithm converts the discrete boundary of an object into a piecewise continuous boundary. Analytic methods are then applied to compute skeletons directly using properties of skeletons in continuous space. Most algorithms use polygonal approximations of boundaries, although circular arcs have also been used. Voronoi diagrams of discrete samples of an object boundary have been used for skeleton computation.

The third category method used is actually a discrete version of the first category methods. The skeleton is the set of centers of discrete maximal disks contained in the discrete figure. The centers of the maximal disks can be extracted from the distance map (or distance transform) of the figure. The remaining task is to resolve the problem that the set of centers of maximal disks is in general disconnected. Many algorithms of this type have been proposed. The major differences are in the type of distance maps used and the methods for connecting the set of centers of maximal disks.

Algorithms have been proposed to detect skeletons by applying ridge finding operators directly to distance maps, and are exemplified later in this invention. This approach detects skeleton points based on response from local operators. Pseudo-skeletons have been extracted directly from gray level images by tracing ridges of gray scale. Ridges may or may not correspond to object geometry, thus the term "pseudo-skeleton."

Figure 3B:
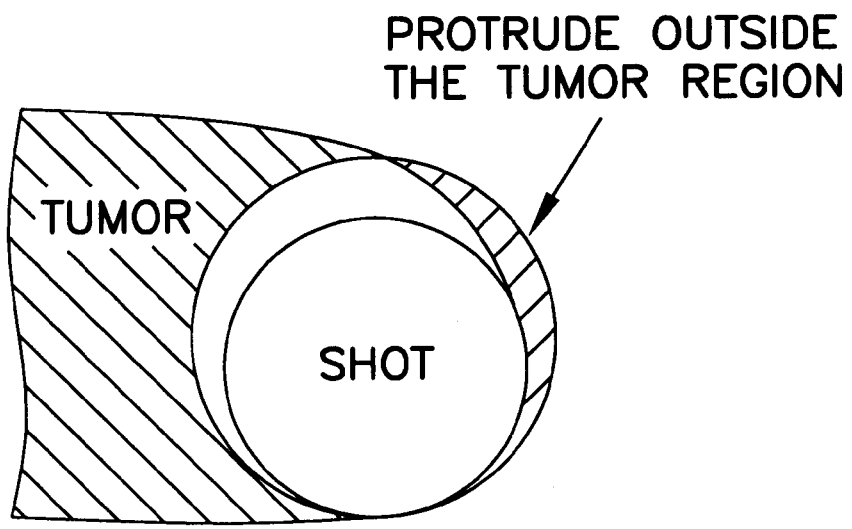

FIG. 3($a$) shows the match for an optimal shot in which the maximum internal disc A is found by skeletonization. FIG. 3($b$) demonstrates that a good match of shot and target requires not only the correct isocenter position, but also the proper diameter. An optimal match of the shot and the target requires that the shot position and size be optimized simultaneously. However, most optimization methods used for conventional radiation treatment planning optimization cannot perform simultaneous optimization for multiple parameters (Stone, R. A., Smith, V., Verhey, L., 1993, "Inverse Treatment Planning of the Gamma Knife," *Med. Phys.,* Vol. 20(3):865; Braham, A., Kallman, P., Lind, B. K., 1989, "Optimization of Proton and Heavy Ion Therapy Using an Adaptive Inversion Algorithm," *Radiotherapy and Oncology,* Vol. 15: 189–197; Starkschall, G., 1984, "A Constrained Least Squares Optimization Method for External Beam Radiation Therapy Treatment Planning," *Med Phys.* 11 (5):659–665). However, the medial axis transformation fulfills this requirement and is used as the key component in our proposed new optimization process for planning gamma unit radiosurgery and/or linear accelerator treatment.

Based on the symmetrical characteristics of each shot, for any optimal coverage of target R, it is guaranteed that the center of each shot is located on the corresponding skeleton (Wu, Q. R., 1996, "Treatment Planning Optimization for Gamma Knife® Radiosurgery," Ph.D. thesis, Mayo Foundation/Mayo Graduate School, Rochester, Minn.), $X(R_i)$, where $R_i$ is the residual region after $S^{d_1}(x_1)$, $S^{d_2}(x_2)$, ... $S^{d_{i-1}}(x_{i-1})$ has been segmented from the original region. Denote $P_{N_{opt}}(R)$ as an optimal coverage of target region R, then we have $$P_{N_{opt}}(R) = \bigcup_i^{N_{opt}} S^{d_i}(x_i) = P_N(R) \mid N = \min(n), \qquad (2)$$

$$\forall n, \frac{V(R) - V\left[\bigcup_{i=1, x_i \in X(R_i)}^{n} S^{d_i}(x_i)\right]}{V(R)} \le \epsilon$$

$$\text{and } R_i = R - \bigcup_{j=1}^{i-1} S^{d_j}(x_j).$$

Equation (2) states that there exists an optimal configuration of shots (i.e., their varied sizes and placements), with each shot centered on $X(R_i)$, that can cover the region R. The difference between equations (1) and (2) is that equation (2) states that all shots are on their corresponding skeletons. Detailed discussion can be found in reference 4.

With the medial axis transformation approach, if there is an optimal coverage of region R, then each shot's center lies on its corresponding residual region $X(R_i)$, and its size is the skeleton radius. Based on this, the optimal plan can be reached by only considering shot centers on the skeleton and the resulting radii are always optimal. Hence, both the position and size of a shot match the region simultaneously and the complexity of the optimization can be reduced significantly.

Suppose there is an optimal shot coverage for the given target region R. Assume one shot is removed from the set of optimal shots. Then, the rest of the coverage is still an optimal coverage for the corresponding new target region, excluding the region covered by the removed shot. This process can be expressed as, $$P_{Nopt}(R) = S^{d_i}(x_i) + P_{Nopt-1}(R - S^{d_i}(x_i)) \qquad (3)$$

Equation (3) suggests a dynamic programming/optimization scheme. The key concept here is that each shot is optimal for the part of the region it covers, independent of other shots (Wu, Q. R., 1996, "Treatment Planning Optimization for Gamma Knife® Radiosurgery," Ph.D. thesis, Mayo Foundation/Mayo Graduate School, Rochester, Minn.). Hence searching of the optimal coverage can proceed as a dynamic programming process.

$$\min N \mid P_N(R) = \min N \mid \{S^{d_1}(x_1) + P_N(R - S^{d_1}(x_1))\} \qquad (4)$$
$$= 1 + \min N \mid P_N(R - (S^{d_1}(x_1)),$$
$$\forall S^{d_1}(x_1) \subset R$$

Equation (4) is a global combinatorial search process. It attempts all possible solutions to find the optimal one. There is no preferred direction in searching for the solution, and the search wholly depends on the shape of the target region. Thus the optimization is highly objective and is unbiased. As stated earlier, there are only 4 physical collimators with the diameters of 18, 14, 8 and 4 mm, and weights of 1.0–0.7 can be used to fine adjust the shot sizes. The gamma unit has the physical precision limit of 0.2 mm for treatment. Hence the available shot sizes are limited to 0.2–0.3 mm finest resolution, which restricts the number of possible solutions and guarantees a fast search.

FIG. 4 shows some snapshots during the optimization process for a 2D target. The minimum width of the target is about 40 mm. First, the initial skeleton is calculated as shown in FIG. 4(a). There are three endpoints for this particular target. For each end point region, one or more shots are available as possible shots. FIG. 4(b) shows four shots, E1, E2, E3 and E4, that are determined for the endpoints of the skeleton. These four shots are recorded and each of them initiates a plan. FIG. 4(c) shows the start of one plan with end point shot E1 as the first shot. Then the unplanned region is updated (shaded region). The boundary of the unplanned region includes part of the original boundary and part of shot E1's boundary (which is chosen at its 50% ISL). In FIG. 4(d), the new calculated skeleton for the unplanned region is shown with two cross points on it. Because two cross point shots are found, the plan based on the selected initial shot E1 increases by 1, i.e., the initial plan started with E1 is split into two plans, each with the same first shot as E1 but a different second shot (C1 or C2).

Figure 4E:
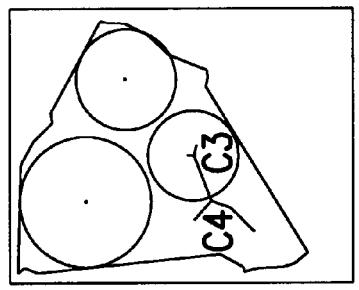
FIG. 4 shows snapshots of the optimization process: (a) initial skeleton of the target region, (b) shots fit all the end-point regions, with a total of four shots found, (c) one potential optimal plan, with the first shot made and the black indicating the updated target region for optimization, (d) new skeleton is calculated for the updated target region, and another optimal shot is plotted on one of the two crosspoints, and (e) the third shot is added, and the process continues.
Figure 4D:
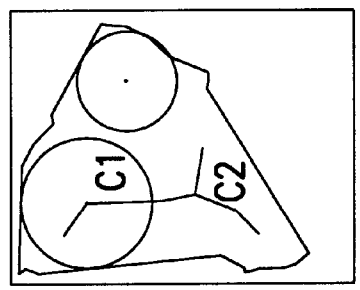
Figure 4C:
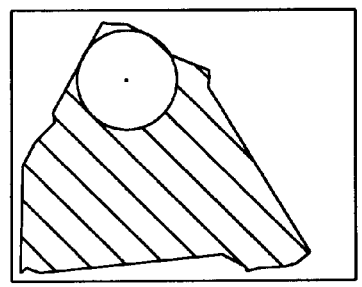
Figure 4B:
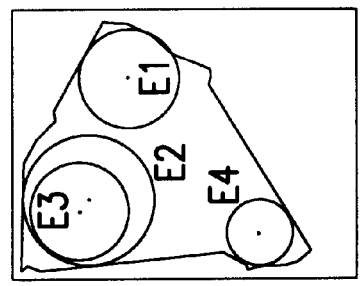
Figure 4A:
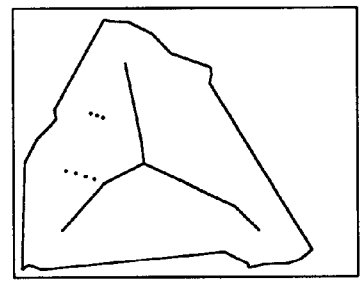
Figure 5:
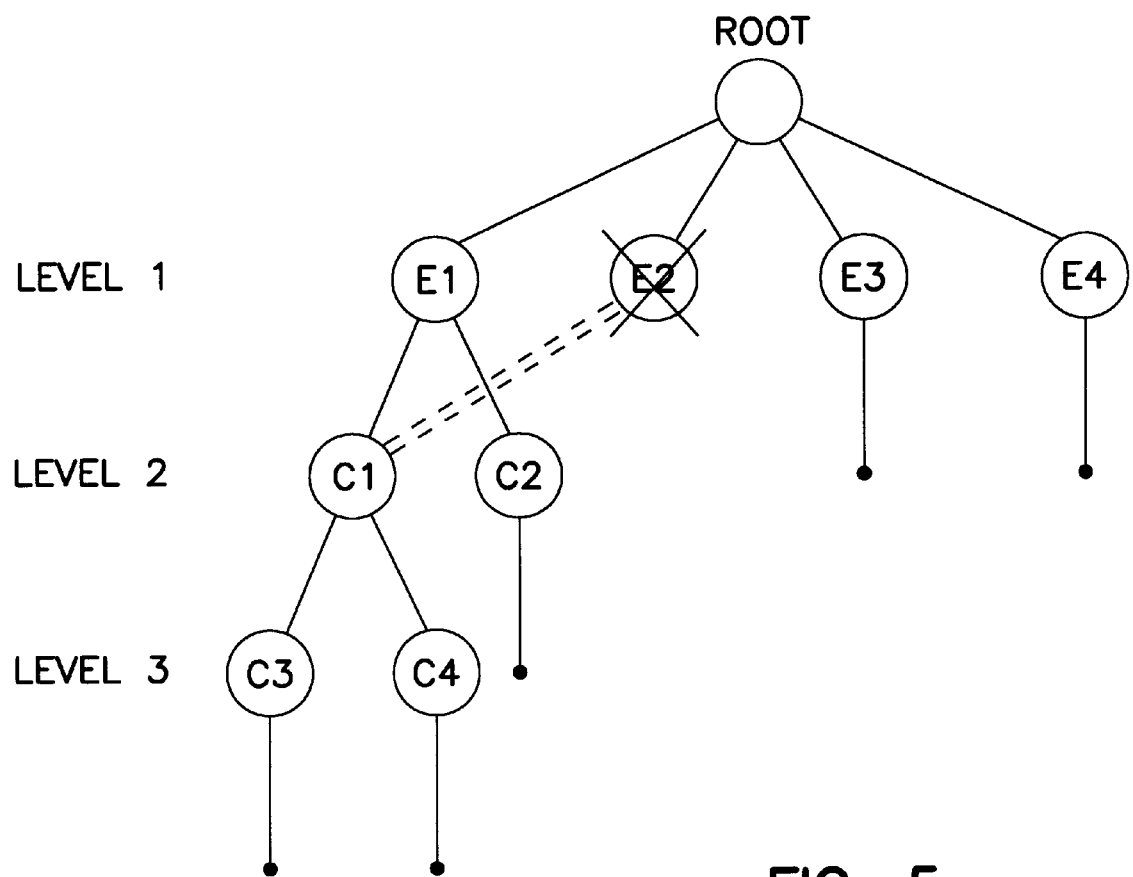
FIG. 5 shows a snapshot or diagram of a solution tree during the optimization or configuration of a shot pattern.

Each cross-point shot (C1 and C2) touches two sides of the original target boundary and also touches one side of the boundary formed by the first shot (E1). One of these two new shots (C1) is shown in FIG. 4(d). Notice this shot is actually one of the initial end point shots (E2) from the initial skeleton in FIG. 4(b), i.e. E2=C1. So E2 is eliminated from the search. The iterative procedure is illustrated one step further, showing the addition of a third shot (C3), in FIG. 4(e). FIG. 5 shows part of the solution tree related to the stages described above.

Figure 6A:
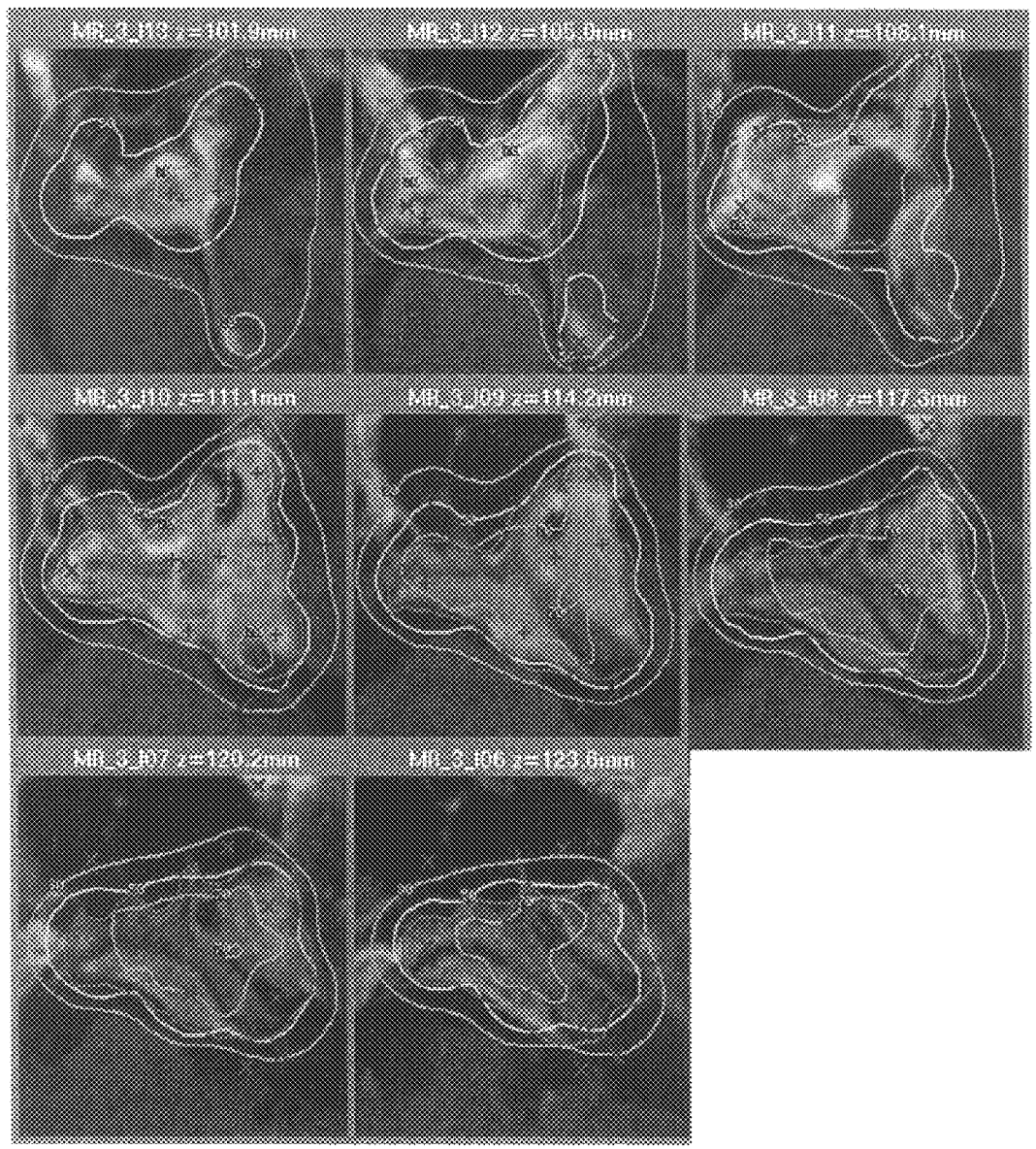
FIG. 6 (a) shows a dose distribution for an optimal treatment plan for a patient with a sinus tumor; (b) shows an optimal plan, with the circles shown being 50% IsoDose Levels (ISLs) of the shots at slice positions, with the gray line indicating the original target contour, and the shaded region indicating the real target used for optimization.
Figure 6B:
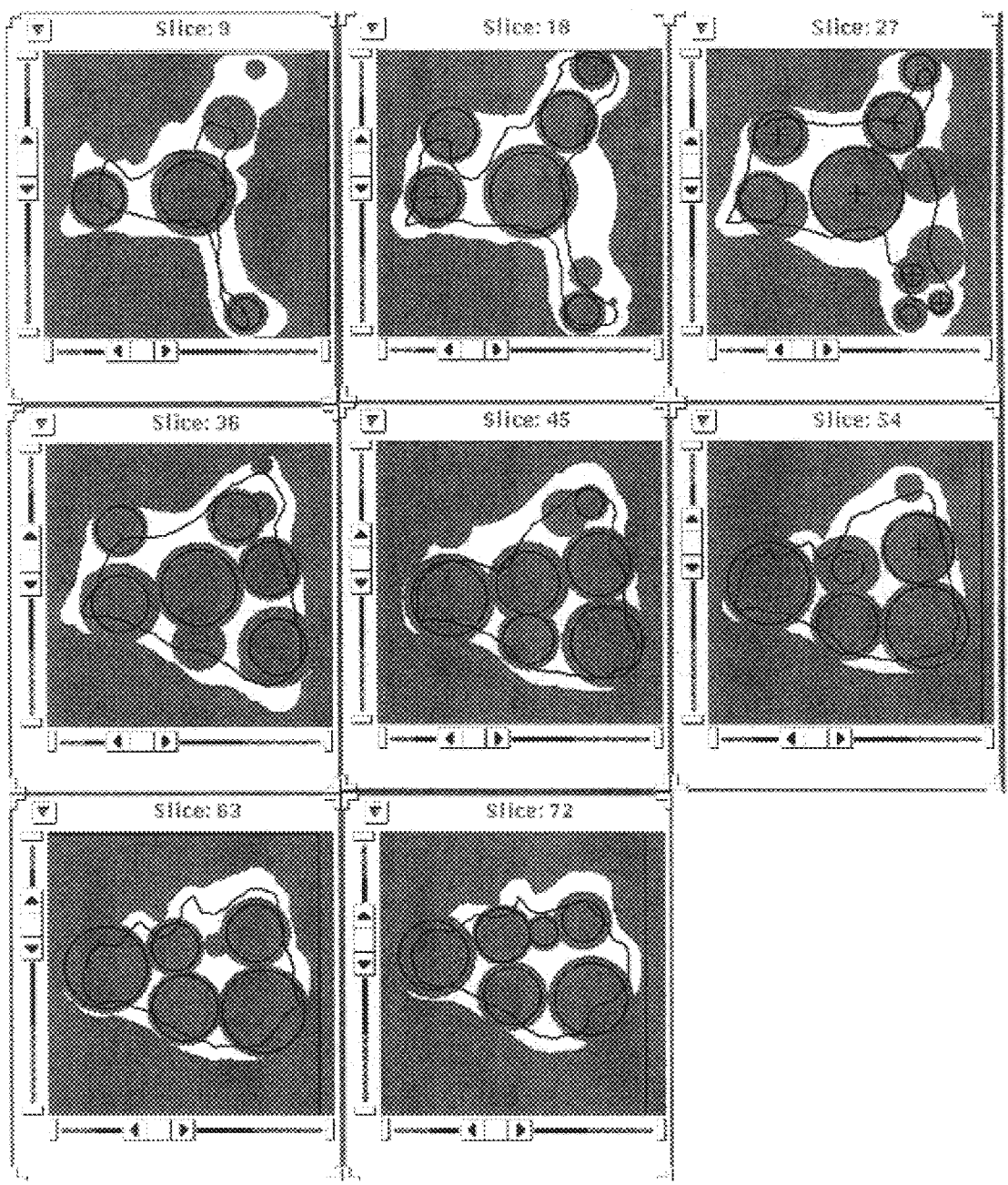

FIG. 6 illustrates a real case—a patient with a sinus tumor. The original slice thickness is 3 mm, as indicated by the z-values in FIG. 6(a). The optimization proceeds with a resolution of 0.33 mm, so the original slices are corresponding to slices #9, #18, . . . , etc. in FIG. 6(b). For the first few slices, the contour shape changes significantly, while the target simply shrinks without changing in shape for the last few slices. The irregularity of the target shape demands the use of many small shots to exactly fit the sharp curves, resulting in a large amount of treatment time. Thus a 3D dilation is performed on the original binary target to smooth out the sharp edges at the cost of slightly increased penumbra dose (Wu, Q. R., 1996, "Treatment Planning Optimization for Gamma Knife® Radiosurgery," Ph.D. thesis, Mayo Foundation/Mayo Graduate School, Rochester, Minn.). This dilation is clinically justified as the treatment plan should have the resulting 50% ISL fully encompass the target while limiting the number of shots to a reasonable number. Also, 3D dilation provides information for arrangement of shots in the third(z) dimension. Basically, the 3D dilation simulates the dose spread in all three dimensions. For example, the heavier shaded region at the bottom of the first slice indicates that if the second slice (#18) is to have 50% ISL coverage of its own shaded region, then the first slice (#9) must have its 50% ISL larger than expected based on the target shape. Depending on experience, a planner may or may not realize the effect of a shot on a different slice. The three dimensional dilation is a way of matching a higher dose level, e.g., 60–70%, to the target boundary. The dilation artificially increases the target boundary by a set amount $\Delta r$ in three dimensions.

For relatively open and large regions, large shots are used and the method tries to optimally arrange them so that they fit into the target region in all the slices. As shown in the figure, shots are optimally positioned in all of the slices. For sharp curvature (e.g., the lower-right side of the target), several small shots are used, as shown in slices #27 and #18 in FIG. 6(b). The 70%, 50%, and 30% ISL'S are shown. The 70% ISL is clinically used to index the dose homogeneity within the target, and the 30% ISL is used to index the penumbra. All three ISL's are conformed to the target contours, with the first two slices having relatively larger spreads as they are above all the isocenter locations. For each individual shot, the isodose spread is wider above the isocenter than for below the isocenter. Therefore the dose distributions are always less conformal for the first few slices. These relatively larger dose spreads result from significant changes in target shape for the first few slices. Dose to the last few slices is highly conformal as the shape remains more consistent.

In this optimization procedure, a medial axis of the target volume is used to simultaneously determine the position and size of treatment shots. As a shot's position and size are coupled, optimizing them simultaneously is required. Much of the computation expense can be saved by using the medial axis, compared with other optimization methods (Stone, R. A., Smith, V., Verhey, L., 1993, "Inverse Treatment Planning of the Gamma Knife," *Med Phys.*, Vol. 20(3):865; Braham, A., Kallman, P., Lind, B. K., 1989, "Optimization of Proton and Heavy Ion Therapy Using an Adaptive Inversion Algorithm," *Radiotherapy and Oncology*, Vol. 15: 189–197; Starkschall, G., 1984, "A Constrained Least Squares Optimization Method for External Beam Radiation Therapy Treatment Planning," *Med Phys.* 11(5):659–665) which optimize shot's position and size independently. Only end points and cross points of the skeleton are selected for the optimization: this is one of the significant advantages of our approach, since the 3D problem of positioning an optimal shot is reduced to 1D problem. For complicated target shapes, small shots are required. For simple targets with the same volumes, large shots can be used. Therefore, the usage of shots should not be predetermined and should be optimized automatically based on target shape. In this work, not only shot sizes, positions, and weights are determined by the skeleton of the target, but the total number of shots used is also determined. The optimal plan is thus reached based on the size and shape of the target, which models the human approach used in manual planning.

Dose is not calculated during the optimization process, and a large amount of computation time is saved. The optimization predicts the final dose distribution and agrees well with external dose calculations. The majority of the calculation time is consumed by determination of the medial axis transform. Faster 3D medial axis transform algorithms will increase the speed of the optimization dramatically ([7]Wu, Q. R., Bourland, J. D., Robb, R. A., 1996, "Fast 3D Medial Axis Transform to Reduce Complexity and Computation for Radiosurgery Treatment Planning," has been presented at SPIE Medical Imaging 96).

In summary, a novel technique of treatment planning optimization for the gamma unit is presented and demonstrated for test and clinical cases. The optimization is based on shape analysis and is reduced to a 1D optimization problem which not only simplifies the procedure but also reduces computational cost.

In gamma unit radiosurgery treatment planning, dose delivery is based on the unit "shot," a distribution of dose approximately spherical in shape. Multiple shots are used to cover different parts of a given target region. Effective 3D optimization for gamma unit treatment has not been previously reported. In this article, a novel optimization method is introduced based on medial axis transformation techniques. Given a defined target volume, the target's medial axis, which uniquely characterizes the target, is used to determine the optimal shot positions and sizes. In using the medial axis, the 3D optimization problem is reduced to a 1D optimization, with corresponding savings in computational time and mathematical complexity. In addition, optimization based on target shape replicates and automates manual treatment planning, which makes the process easily understandable. Results of optimal plans and the corresponding dose distributions are presented. The next section of this discussion more specifically addresses the relationship between skeleton disks and the dose distributions they predict.

In two dimensional continuous space, the skeleton or medial axis is often described as the set of internal quench points of a "grass fire" started at the region's border (Blum, H., 1973, "Biological Shape and Visual Science (Part I)," *J. of Theoretical Biology*, 38, pp. 205–287). Suppose fires are lighted simultaneously along the entire boundary of a region. Each point on the region boundary is then considered as a source which grows by consuming the grass uniformly in all directions, thereby producing a disk-shaped wave front. When two or more fire fronts intersect, the fire is extinguished at the point of contact. The extinction points delineate the skeleton. The skeleton can also be defined as the locus of the centers of all the maximal internal disks, circles which are wholly contained within the region, but are not wholly contained within any other internal disks. A maximal disk is always tangential to the boundary of the region in at least two places.

For a two-dimensional object, the skeleton, or the medial axis, is a collection of intersecting curved line segments, and for a three-dimensional object, the corresponding skeleton is a collection of intersecting curved lines and surfaces. A medial surface is formed if each maximal internal disk is tangential to the boundary at two or more places, and a medial axis is formed if each maximal internal disk is tangential to the boundary at three more places.

Methods for calculating medial axes in the digital domain have been extensively investigated. One type of skeletonization is morphological thinning (Maragos, P. A., and Schafer, R. W., 1986, "Morphological Skeleton Representation and Coding of Binary Images," *IEEE Transactions on Acoustics, Speech and Signal Processing*, Vol. ASSP-34, No. 5, 1228–1244; Serra, J., 1982, Analysis and Mathematical Morphology, Volume 1, Academic Press, London; Serra, J., 1988, Image Analysis and Mathematical Morphology, Volume 2: Theoretical Advances, Academic Press, London; Tsao, Y. F., and fu, K. S., 1981, "A Parallel Thinning Algorithm for 3-D pictures," *Computer Graphics and Image Processing*, 17, pp. 315–331; Saito, T., Toriwaki, J., 1994, "A Sequential Thinning Algorithm for Three Dimensional Digital Pictures Using the Euclidean Distance Transformation," Proceedings of the 9th Scandinavian Conf. On Image Analysis; Lee, T., and Kashyap, R. L., 1994, "building Skeleton Models via 3-D Medial Surface/Axis Thinning algorithms," *CVGIP: Graphical Models and Image Processing*, Vol. 56, No. 6, pp. 462–478). Although morphological methods may yield a topological preserved skeleton, the intrinsic concept of "thinning" inevitably erodes concave regions faster than convex regions, which results in larger errors for concave images than for convex images. Another type of skeletonization is the ridge extraction from distance mapping (Arcelli, C., and sanniti di Baja, G., 1988, "Finding Local Maxima in a Pseudo Euclidean Distance Transform," *Computer Vision, Graphics and Image Processing*, 43, 361–367; Arcelli, C., and Sanniti di Baja, G., 1992, "Ridge Points in Euclidean Distance Maps," *Pattern Recognition Letters*, Volume 13, No. 4, 237–243; Ragnemalm, I., 1990, "Generation of Euclidean Distance Maps," Ph.D. thesis No. 206. Linkoping University, Sweden; Montanari, U., 1968, "A Method for Obtaining Skeleton Using a Quasi-Euclidean Distance," *J. of the Association for Computing Machinery*, Vol. 15, No. 4, 600–624; Arcelli, C., and Sanniti di Baja, G., 1993, "Euclidean Skeleton Via Center-of Maximal Disc Extraction," *Image and Vision Computing*, Vol. 11, No. 3, 163–173). This technique can closely approximate the true medial axis if the distance mapping is close to Euclidean distance mapping. Ragnemalm (Ragnemalm, I., 1990, "Generation of Euclidean Distance Maps," Ph.D. thesis No. 206. Linkoping University, Sweden) used look-up tables to characterize and extract the local-maxima-disk from the Euclidean distance transform (EDI) map for 2D objects. The local maxima are necessary and sufficient to exactly reconstruct the original object, but they do not usually form a connected set, and therefore are only a subset of the skeleton. Arecli et al. (Arcelli, C., and sanniti di Baja, G., 1988, "Finding Local Maxima in a Pseudo Euclidean Distance Transform," *Computer Vision, Graphics and Image Processing*, 43, 361–367; Arcelli, C., and Sanniti di Baja, G., 1992, "Ridge Points in Euclidean Distance Maps," *Pattern Recognition Letters*, Volume 13, No. 4, 237–243; Arcelli, C., and Sanniti di Baja, G., 1993, "Euclidean Skeleton Via Center-of Maximal Disc Extraction," *Image and Vision Computing*, Vol. 11, No. 3, 163–173) proposed strategies to detect saddle points to construct the skeleton after center-of-maximal-disk extraction. A more elaborate algorithm using a "snakes" concept based on the Blum's grass fire analogy is suggested by Leymarie et al. (Leymarie, F., and Levine, M. D., 1990, "Skeleton from Snakes," Progress in Image Analysis and Processing, 186–193, World Scientific, Singapore; Leymarie, F., and Levine, M.D., 1992, "Simulating the Grassfire Transform Using an Active Contour Model," *IEEE Transactions on Pattern analysis and Machine Intelligence*, Vol. 14, No. 1, 56–75) The "snakes" are positioned on the distance surface and, in descending gradient direction, will seek out valleys or ridges of the surface.

To date, there has been little work done on 3D medial axis transformations. The major reason is that the 3D topological properties are more complex than for 2D. Most mathematical morphological techniques based on 2D morphological operations are not extensible to higher dimensions. New morphological methods (Tsao, Y. F., and fu, K. S., 1981, "A Parallel Thinning Algorithm for 3-D pictures," *Computer Graphics and Image Processing*, 17, pp. 315–331; Saito, T., Toriwaki, J., 1994, "A Sequential Thinning Algorithm for Three Dimensional Digital Pictures Using the Euclidean Distance Transformation," Proceedings of the 9th Scandinavian Conf. On Image Analysis; Lee, T., and Kashyap, R. L., 1994, "building Skeleton Models via 3-D Medial Surface/Axis Thinning algorithms," *CVGIP: Graphical Models and Image Processing*, Vol. 56, No. 6, pp. 462–478; Lobbrget, S., Verbeek, P. W., and Groen, F. C. A., 1980, "Three Dimensional Skeletonization: Principle and Algorithm," *IEEE Transactions on Pattern Analysis and Machine Intelligence*, Vol. PAMI-2, No. 1, 75–77) based on Euler characteristics and connectivity preservation have been investigated. Direct extraction of ridges from EDT maps for 3D images has not yet been reported. There are at least two reasons: 1) the much larger errors associated with 3D EDT make local-maxima extraction more difficult, and 2) detecting saddle points in higher dimensions is difficult.

In this discussion, a fast Euclidean skeletonization algorithm in two and three dimensions based on ridge extraction is presented. Ridges occur when fire fronts collapse during grassfire propagation. Iso-contours (2D) or iso-surfaces (3D) can be obtained from dynamic grassfire transformation and they are locally smooth everywhere except at ridge locations. Ridges are detected by measuring local curvature at each point. The process is local and is invariant under spatial translations and spatial rotations. The ridges may be 2 pixels thick at some locations due to digitization, so a final thinning process is used to ensure the skeleton is only one pixel thick. The algorithm only requires one scan for the local curvature measurement and a fixed number of scans for Euclidean distance transformations, therefore computation is reduced significantly as compared with iterative thinning methods. The algorithm does not require any connectivity check, and therefore can be directly extended to higher dimensions.

The distance transformation produces a distance map for a binary image. For each pixel inside the object in the binary image, the corresponding pixel in the distance map has a value equal to the minimum distance from itself to the background. Denote any pixel with non-zero value as belonging to object set O, and any zero pixel as belonging to background set O', then the initial distance map $f_1(p)$ can be defined as:

$$f_1(p) = \begin{cases} M \Leftrightarrow p \in O \\ 0 \Leftrightarrow p \in O' \end{cases} \quad (1)$$

where M is some real constant value. The values of the function $f_2$ replace $f_1$ by minimizing a distance matrix function, $d(p,p')$ over the object where p and p' are two points in the space such that $p \in O$, and $p' \notin O'$:

$$f_2(p) = \min_{p' \in O', p \in O} [d(p', p)] \quad (2)$$

Danielsson (Danielsson, P. E., 1980 "Euclidean Distance Mapping," *Computer vision, Graphics and Image Processing*, 14, 227–248) first proposed true Euclidean distance transformation (EDT) in 2D. Although it was not an error free algorithm, the error has an upper bound with the maximum error of 0.29 pixel (Borgefors, G., 1986, "Distance Transformations in Digital Images," *Computer Vision, Grphics and Image Processing*, 34, 344–371) and does not increase with image size. EDT for higher dimensional images has been extensively studied (Ragnemalm, I., 1990, "Generation of Euclidean Distance Maps," Ph.D. thesis No. 206. Linköping University, Sweden; Borgefors, G., 1984, "distance Transformation in Arbitrary Dimensions," *Computer Vision, Graphics and Image Processing*, 27, 321–345; Borgefors, G., 1986, "Distance Transformations in Digital Images," *Computer Vision, Grphics and Image Processing*, 34, 344–371; Mullikin, J., 1992, "The Vector Distance Transform in Two and Three Dimensions," *CVGIP: Graphical Models and Image Processing*, Vol. 54, No. 6, pp. 52&535) since Danielsson's report. For 3D EDT, the error has no upper bound and increases with image size. Borgefors (Borgefors, G., 1984, "distance Transformation in Arbitrary Dimensions," *Computer Vision, Graphics and Image Processing*, 27, 321–345) pointed out errors as large as 18% of the image size with 3D EDT.

In this paper, the six raster scan 3D EDT algorithm (Mullikin, J., 1992, "The Vector Distance Transform in Two and Three Dimensions," *CVGIP: Graphical Models and Image Processing*, Vol. 54, No. 6, pp. 526–535) is used. For iterative raster scan distance propagation, the distance map function $f_2(p)$ can be written as:

$$f_2(p) = \begin{cases} \min_{P_N \in N_p(j)} \begin{bmatrix} f_1(p), j = 0, p \in 0 \\ f_2(p(j-1)), f_2(p_N(j)) + w_N \end{bmatrix} j > 0, \\ p \in 0 \end{cases} \quad (3)$$

where $N_p(j)$ is the neighbor of point p defined by the mask used in the present pass, $p_N$ is a pixel in that neighborhood, and $w_N$ is the vector element values given by the mask representing the distance between p and $p_N$. FIG. 1 shows the mask windows for the raster scans and their corresponding distance propagation directions.

Consider a grassfire ignited from the boundary of the object. All the waves travel at the same speed. If the grassfire is considered as a function of time, a space-time graph known as a 2D/3D dynamic grassfire can be obtained (Blum, H., 1973, "Biological Shape and Visual Science (Part I)," *J. of Theoretical Biology*, 38, pp. 205–287). Since all waves travel at a constant speed, such a dynamic grassfire can be obtained by computing EDT on the initial binary image. FIG. 2(*a*) shows the iso-distance contour plot of a rectangle object and FIG. 2(*b*) shows the plot in 3D with the height (z-direction) indicating the Euclidean distance (or time). Wherever firefronts progress "smoothly," the distance contour/surface is locally smooth, or in the other words, the distance contour/surface is relatively flat, so the local curvature is zero (or very close to zero). Wherever firefronts collapse, the distance contour/surface deforms and a ridge is formed. These ridges correspond to the locus of the skeleton. The change of smoothness/flatness depends on the angle at which these wave fronts interact. The sharper the angle, the greater the local curvature of the distance contour/surface.

A ridge point is detected by measuring the maximum curvature of the EDT map at each pixel/voxel. In 2-D space, the curvature at a pixel is well defined since only one contour passes through each pixel. The curvature (Do Canno, M. P., Differential Geometry of Curves and Surfaces, Prentice-Hall, Inc. Englewood Cliffs, N.J., 1976) K at pixel p is:

$$K = \left|\frac{d\vec{t}}{ds}\right| \quad (4)$$

where s is the arc length parameter and t is the unit tangent vector to the iso-contour at p. In 3D space, the curvature at a voxel is not uniquely defined since there exists an iso-surface passing through each voxel. On such an iso-surface, there exists an infinite number of contours, and hence infinite tangent vectors t. For each of the tangent directions, there is one associated curvature value. Among all those tangent directions there are two characteristic directions, along which one has the maximum curvature, and the other has the minimum.

Curvatures along any other tangent directions lie between these extremes. The characteristic directions at each point and the curvature extremes can be obtained from the Hessian matrix:

$$Hess(f) = \begin{bmatrix} \frac{\partial^2 f}{\partial x^2} & \frac{\partial^2 f}{\partial x \partial y} & \frac{\partial^2 f}{\partial x \partial z} \\ \frac{\partial^2 f}{\partial y \partial x} & \frac{\partial^2 f}{\partial y^2} & \frac{\partial^2 f}{\partial y \partial z} \\ \frac{\partial^2 f}{\partial z \partial x} & \frac{\partial 2f}{\partial z \partial y} & \frac{\partial^2 f}{\partial z^2} \end{bmatrix} \quad (5)$$

where f is the EDT function defined on a 3D image domain R, R⊂R (Serra, J., 1982, Image Analysis and Mathematical Morphology, Volume 1, Academic Press, London). Denote $V_1, V_2, V_3$ as the eigenvectors of $-\text{Hess}(f)$ with corresponding eigenvalues $\lambda_1, \lambda_2, \lambda_3$. The Hessian matrix can be transformed into diagonal form, $$\begin{bmatrix} \lambda_1 & 0 & 0 \\ 0 & \lambda_2 & 0 \\ 0 & 0 & \lambda_3 \end{bmatrix} = Q^T \cdot [-Hess(f)] \cdot Q \quad (6)$$

where $Q=[V_1 \ V_2 \ V_3]$ is an orthogonal transform matrix, $Q^T=Q^{-1}$. Since the Hessian matrix is a real and symmetric matrix, the orthogonal transform always results in a real diagonal matrix, and $\lambda_1, \lambda_2, \lambda_3$ are real numbers. Based on equation (6), the eigenvalues are equal to, $$\lambda_2 = -v_1^T Hess(f) v_1$$

$$\lambda_2 = -v_2^T Hess(f) v_2 \quad (7)$$

$$\lambda_3 = -v_3^T Hess(f) v_3$$

The three eigenvectors, $V_1, V_2$ and $V_3$ define an orthogonal coordinate system at voxel p of the EDT map. One of the eigenvectors is the norm to the iso-surface, denoted as $V_3$. Then $V_1$ and $V_2$ are the tangent directions with the maximum and minimum curvatures. Actually, $V_1$ and $V_2$ define a tangent plane at voxel p in which the fire fronts collapse. Denote this plane $S_p$, then, $$V_3 \cdot \vec{t} = 0, \forall \vec{t} \in S_p \quad (8)$$

where $v_3 = \nabla f / |\nabla f|$. Also, $$\frac{d(V_3 \cdot \vec{t})}{ds} = \frac{dV_3}{ds} \cdot \vec{t} + V_3 \cdot \frac{d\vec{t}}{ds} \quad (9)$$

where $dv_3/ds$ can be expressed as:

$$\frac{dV_3}{ds} = \frac{\partial V_3}{\partial x}\frac{dx}{ds} + \frac{\partial V_3}{\partial y}\frac{dy}{ds} + \frac{\partial V_3}{\partial z}\frac{dz}{ds} = \frac{Hess(f)\vec{t}}{|\nabla f|}$$

Then the curvature K along an arbitrary tangent direction t on the iso-surface at voxel p is, $$K = \frac{-\vec{t}^T H \vec{t}}{|\nabla f|} \quad (10)$$

Based on equations (7) and (10), the curvatures along tangent directions $V_1$ and $V_2$ are $\lambda_1/|\nabla f|$ and $\lambda_2/|\nabla f|$, respectively. Since $\lambda_1$ and $\lambda_2$ represent the maximum and minimum curvatures of the iso-surface at point p, a surface curvature index can be constructed as:

$$K_s = \begin{bmatrix} \lambda_1 \\ \lambda_2 \end{bmatrix} = -\begin{bmatrix} V_1^T H V_1 \\ V_2^T H V_2 \end{bmatrix} \quad (11)$$

Equation (11) describes the curvature characteristics of the iso-surface at a point, i.e., it describes the measured deviation of the local iso-distance surface from flatness. $V_1$ represents the direction (in 3D) along which the local iso-surface has the maximum curvature, and $V_2$ is the direction along which the local iso-surface has minimum curvature. Curvatures along any other directions are between these two extremes.

Using the surface curvature index concept, a new algorithm is developed to search the ridge points in 2D and 3D space. Finite difference schemes are used to obtain all the derivatives. The eigenvalues and eigenvectors of the Hessian matrix are obtained by Householder reductions and QL decomposition (Press, W. H., Teukosky, S. A., Vetterling, W. T., and Flannery, B. P., 1992, Numerical Recipes in C, Cambridge University Press). In 2D, assuming there exists eigen values $\lambda_1$ and $\lambda_2$ with corresponding eigen vectors $V_1$ and $V_2$ at point p, where $V_2$ is the norm of the iso-contour line, and in 3D, assuming there exists eigen values $\lambda_1 > \lambda_2$ and $\lambda_3$ with corresponding eigen vectors $V_1, V_2$, and $V_3$ where $V_3$ is the norm of the iso-surface, then the criteria for ridge points are:

(a) for 2D object, p is a ridge point, if $K \geq 0.50$.

(b) for 3D object, p is a medial surface ridge point, if $$K_s \geq \begin{bmatrix} 0.65 \\ 0 \end{bmatrix}$$

(c) for 3D object, p is a medial axis ridge point, if $$K_s \geq \begin{bmatrix} 0.65 \\ 0.65 \end{bmatrix}$$

Thinning Ridge

In discrete space, the true skeleton point may be found to be between 2 adjacent pixels/voxels. In such cases, both adjacent points are taken as ridges. One final thinning step is required to further thin the ridge to a single pixel width. The thinning method used is from Lee and Kysharp (Lee, T., and Kashyap, R. L., 1994, "building Skeleton Models via 3-D Medial Surface/Axis Thinning algorithms," *CVGIP: Graphical Models and Image Processing*, Vol. 56, No. 6, pp. 462–478). The maximum number of iterations used is two.

The medial surface of a cube may be shown in slice-by-slice views with the slice index increasing left to right and from top to bottom, with a ridge being present. The ridge in the center of the object is, for example, two pixels thick as the cube size is purposely chosen as 30 voxels. Hence, all 8 points in the center of the cube have the same maximum distances and surface curvature indexes. All 8 pixels are detected as ridge points as expected. It is not surprising that the skeleton of the cube is different from those obtained with thinning methods (Lee, T., and Kashyap, R. L., 1994, "building Skeleton Models via 3-D Medial Surface/Axis Thinning algorithms," *CVGIP: Graphical Models and Image Processing*, Vol. 56, No. 6, pp. 462–478). The thinning methods in 3D are essentially using the city-block distance rather than Euclidean distance, therefore the distance in the diagonal directions is taken as one unit when it should actually be $\sqrt{2}$ and $\sqrt{3}$. Obviously those branches indicating diagonal distance will be missed. Therefore, this new algorithm has the inherent superiority of representing a true Euclidean skeleton.

Theoretically, in continuous space, a flat surface represents zero curvature and any curvature larger than zero should predict a ridge. In discrete space, however, ridges from small curvatures may not be detected since only integer distances are allowed. A simple "deformation" experiment is performed to test the algorithm. A rectangle is chosen as the reference object, with width of 30 pixels and length of 120 pixels. All the skeletons are, for example, from ridge extraction and may be two pixels thick. Only ridge points with distance values greater than three are considered as part of the skeleton, in order to avoid the noise from digitization of the edges. The skeleton consists of four short branches and one long central branch. The large length to width ratio is chosen to ensure that the four short branches are far away from the point of deformation, so that the distance surface around the deformation point is locally smooth. Therefore any ridge detected around the deformation point is due to the deformation only. A "handle" is placed at the middle point of one of the long edges. Assume the edge is elastic and pulled outwards. A series of such "deformed" rectangles are tested. It is found that the algorithm starts to pick up ridge points when the "handle" is more than 10 pixels outside of its original position. A fully connected ridge branch is detected when the handle is more than 20 pixels outside. Notice some points are two pixels thick and a final thinning is required to determine the medial axis. These "handle" positions of 10 and 20 pixels correspond to the waves front interacting angles of 152° and 145°, respectively.

Also, the skeleton branch due to the deformation need not all be connected. There are two reasons for the missing points. One is that it is difficult to digitize an edge with such a small amount of tilting. The "zigzag" effect of the discretization may result in mis-representation of the true edge point. Eventually the ridge point distance is propagated from this edge point in error. The other reason is that 3D EDT is not an error free grassfire propagation, therefore the curvature index calculated from the 3D EDT may deviate from the true curvature, resulting missed ridge points.

As stated above, only ridge points with a distance value greater than three are considered. For pixels close to the edge, the "zigzag" phenomena has a much greater influence on local curvature, and spurious ridge points occur more often. These ridge points are usually isolated ridge points and their distributions reflect the shapes of the digital edges.

3D EDT requires 6 scans across the image, and the local curvature measurement takes one scan. A final thinning step is necessary to thin some 2 pixel thick ridges, which takes no more than two scans. In summary, this algorithm requires a fixed number (9) of scans of the image. A timing experiment was performed to compare our method to the thinning method proposed by Lee et al. (Lee, T., and Kashyap, R. L., 1994, "building Skeleton Models via 3-D Medial Surface/Axis Thinning algorithms," *CVGIP: Graphical Models and Image Processing*, Vol. 56, No. 6, pp. 462–478). The 3D EDT algorithm used here is proposed by Mullilin (Mullikin, J., 1992, "The Vector Distance Transform in Two and Three Dimensions," *CVGIP: Graphical Models and Image Processing*, Vol. 54, No. 6, pp. 526–535). The computer used was a SPARC station 5/70. The initial cube size was 20×20×30 voxels, whose volume was denoted as $V_0$. Several cubes with volumes of $2V_0$, $8V_0$, 27 $V_0$, 64 $V_0$ were tested for computational expense, from which the maximum volume of 64 $V_0$ corresponded to the image size of 60×80×120 voxels. The ridge extraction method included the final thinning step. FIG. 5 shows the computation expense vs. object size in log scale. The computation time increases exponentially with object size. But the slope for the thinning method is larger than that for the ridge method. The thinning method is 6 times slower for small objects ($V_0$), and is up to 35 times slower (95 sec. vs. 3295 sec.) for large objects.

In radiosurgery treatment planning, optimal shots can only be located on the locus of the media axis of a 3D target, with shot sizes corresponding to the maximum internal disks (Wu, Q. R., 1996, "Treatment Planning Optimization for Gamma Knife® Radiosurgery," Ph.D. Thesis, Mayo Foundation/Graduate School, Rochester, Minn.). Each host has a dose distribution similar to a point spread function, and 50% isodose level is defined as the shot "size". Multiple shots are used to cover an irregularly shaped target. The goal of effective treatment planning is to optimally arrange all the shots to provide homogeneous dose coverage to the target, while minimizing dose to the surrounding normal tissues. By using the medial axis transformation, both complexity and computation time are reduced significantly. The treatment planning process consists of the following steps:

Step (1): Calculate the medial axis of the given region.

Step (2): Final all the end points on the skeleton. Sort the endpoints in the order of increasing internal disk radii. Shots selected at each end point are regarded as the initial shots for their corresponding plans.

Step (3): For each plan, record the shot, and update the target region to exclude that part of the region covered by the new shot. Calculate the skeleton of the remaining region.

Step (4): Detect any cross points of the skeleton if they exist. Sort the cross points in the order of ascending internal disk radii. A cross point is the point where two or more skeleton branches meet. Inherently, a shot based on a cross point will match multiple boundary sides and thus is the best shot for that part of the region. If a cross point is found, the next shot is centered on it If several cross points are found, a combinatorial search is performed. If not cross-point is found, then return to step (2).

Step (5): Iterate step (3) and step (4), until the coverage is within the requirement.

Once the total coverage is within the requirement, a treatment plan is reached. The one with the least number of shots is chosen as the optimal plan. FIG. 6 illustrates one medial axis transform guided radiosurgery plan. FIG. 6(a), shows the final plan, with the circles indicating the shots on each slice. Gray lines may show the original target contours and shaded regions may show the actual target regions used for planning. FIG. 6(b) shows the corresponding dose distributions.

For fire wave front interacting angles between 0 and 90 degrees, the curvature index is between 2.0 and 1.5 and the ridges are strong. These type of ridges are similar to the strong ridge points referred to by Arcelli (Arcelli, C., and Sanniti di Baja, G., 1992, "Ridge Points in Euclidean Distance Maps," *Pattern Recognition Letters,* Volume 13, No. 4, 237–243), and can be detected using the local-maximal-disk concept. For angles between 90 and 180 degrees, the curvature index (between 1.5 and 0.0) is weaker. This type of ridge is similar to weak ridge points referred to by Arcelli (Arcelli, C., and Sanniti di Baja, G., 1992, "Ridge Points in Euclidean Distance Maps," *Pattern Recognition Letters,* Volume 13, No. 4 237–243), and cannot be detected directly by the local-maximum-disk extraction. For example, ridge points from angle 150 to 180 degrees may not be detected.

Thinning methods in 3D are much more complicated than in 2D, and Euler characteristics are used to preserve the connectivity (Tsao, Y. F., and fu, K. S., 1981, "A Parallel Thinning Algorithm for 3-D pictures," *Computer Graphics and Image Processing,* 17, pp. 315–331; Saito, T., Toriwaki, J., 1994, "A Sequential Thinning Algorithm for Three Dimensional Digital Pictures Using the Euclidean Distance Transformation," Proceedings of the 9th Scandinavian Conf. On Image Analysis; Lee, T., and Kashyap, R. L., 1994, "building Skeleton Models via 3-D Medial Surface/Axis Thinning algorithms," *CVGIP: Graphical Models and Image Processing,* Vol. 56, No. 6, pp. 462–478). Connectivity for higher dimensions is even harder to verify. The ridge exrraction method proposed in this paper only checks local curvature of the iso-distance surface, and diagonalization of Hessian matrix is used to find the principle curvature directions, so the method can be directly extended to higher dimensions. Since the Euclidean distance transform and curvature measurement is translation and rotation invariant, the algorithm is also translation and rotational invariant. This invariance offers an advantage over other thinning methods.

The curvature measurment is a local operation so that all pixels/voxels in an object are processed simultaneously. In contrast, morphological methods can only detect skeleton points on the outer most layer, and the layers have to be "peeled off" sequentially. As object size increases, surface area increases faster, hence ridge extraction offers advantages for speed in processing large objects.

In radiosurgery treatment planning, optimal shot positions can be found on the locus of the medial axis of the 3D target with shot sizes correspondinb to the maximum internal disks as provided by skeletonization. This is the target shape based optimization and offers great advantage over other optimization methods([24]Stone, R. A., Smith, V., Verhey, L., 1993, "Inverse Treatment Planning for the Gamma Knife," *Med Phys.,* Vol. 20(3):865). Both complexity and computation time are reduced significantly compared to manual panning.

```
/*
 *
 */
#include <stdio.h>
#include <math.h>
#include <mailoc.h>
#include <sys/param.h>
#include <sys/types.h>
#include <sys/time.h>
#include <string.h>
#if defined{__STDC__}
#include <stdarg.h>
#else
#include <varargs.h>
#endif
#include <values.h>
#include "g3dplan.h"
main(argc,argv)
int argc;
char *argv[ ];
{
    int    i, j, count;
    float  maxx, maxy, maxz, minx, miny, minz;
    float  xm, ym, zm;
    char sbuff[256];
    char  *input = NULL;
    char *output = NULL;
    FILE  *fp = NULL;
    CONTOUR contour;
    /*
     * get the file name
     */
    if(argc != 13)
    {
        fprintf(stderr,"%s: Usage: %s input output count maxx maxy maxz minx miny minz xm ym zm\n", argv[0], argv[0]);
        exit[1];
```

```
}
input = argv[1];
output = argv[2];
count = atoi(argv[3]);
maxx = atof(argv[4]);
maxy = atof(argv[5]);
maxz = atof(argv[6]);
minx = atof(argv[7]);
miny = atof(argv[8]);
minz = atof(argv[9]);
xm = atof(argv[10]);
ym = atof(argv[11]);
zm = atof(argv[12]);
/*
 * read the contour slices
 */
/* allocate memory for contour */
contour.num_slices = count;
contour.z = (float *) calloc(contour.num_slices,
sizeof(float));
if(contour.z == NULL)
{
    fprintf(stderr, " %s: can not allocate memory for
    contour points \n", argv[0]);
    exit(1);
}
contour.x = (float **) calloc(contour.num_slices, sizeof(float
*))
contour.y = (float **) calloc(contour.num_slices, sizeof(float
*));
if(contour.x == NULL || contour.y == NULL)
{
    fprint(stderr, " %s: can not allocate memory for
    contour points \n", argv[0]);
    exit(1);
}
contour.num_vert = (int *) calloc(contour.num_slices,
sizeof(int));
if(contour.num_vert == NULL)
{
    fprintf(stderr, " %s: can not allocate memory for
    contour points \n", argv[0]);
    exit(1);
}
contour.z = (float *) calloc(contour.num_slices,
sizeof(float));
if(contour.z == NULL)
{
    fprintf(stder, " %s: can not allocate memory for
    contour points \n", argv[0]);
    exit(1);
}
for(i=0;i<contour.num_slices;i++)
{
    contour.z[i] = i;
    if(i > 9)
            sprintf(sbuff, "%s%d", input, (i));
    else
            sprintf(sbuff, "%s0%d", input, (i));
    if((fp = fopen(sbuff,"r")) == NULL)
    {
        fprintf(stderr, " %s: can not open file %s\n",
        argv[0], sbuff);
        exit[1];
    }
    if ((fscanf(fp, "%d",&(contour.num_vert[i]))) != 1)
    {
        fprintf(stderr, " %s: read file %s error for
        number of vertices\n", argv[0], sbuff);
        fclose(fp);
        exit[1];
    }
    contour.x[i] = (float *) calloc(contour.num_vert[i],
    sizeof(float));
    contour.y[i] = (float *) calloc(contour.num_vert[i],
    sizeof(float));
    if(contour.x[i] == NULL || contour.y[i] == NULL)
    {
        fprintf(stderr, " %s: can not allocate memory
```

```
                    for contour points for slices %s\n",
                        argv[0], sbuff);
                fclose(fp);
                exit(1);
            }
            for(j=0;j< contour.num_vert[i];j++)
            {
                if((fscanf(fp,"%g", &(contour.x[i][j]))) != 1 )
                {
                    fprintf(stderr. " %s: read file %s
                    error for vertex coordinates\n",
                        argv[0], sbuff);
                    fclose(fp);
                    exit(1) ;
                }
                if((fscanf(fp,"%g", &(contour.y[i][j]))) != 1 )
                {
                    fprintf(stderr, " %s: read file %s
                    error for vertex coordinates\n",
                        argv[0], sbuff);
                    fclose(fp);
                    exit(1) ;
                }
                if( i == 0 && j == 0)
                {
                    contour.min_x = contour.x[i][j];
                    contour.min_y = contour.y[i][j];
                    contour.max_x = contour.x[i][j];
                    contour.max_y = contour.y[i][j];
                    contour.min_z = contour.z[i][j];
                    contour.max_z = contour.z[i][j];
                }
                else
                {
                    if(contour.x[i][j] < contour.min_x)
                        contour.min_x =
                        contour.x[i][j];
                    if(contour.y[i][j] < contour.min_y)
                        contour.min_y =
                        contour.y[i][j];
                    if(contour.z[i] < contour.min_z)
                        contour.min_z = contour.z[i];
                    if(contour.x[i][j] > contour.max_x)
                        contour.max_x =
                        contour.x[i][i];
                    if(contour.y[i][j] > contour.max_y)
                        contour.max_y =
                        contour.y[i][j];
                    if(contour.z[i] > contour.max_z)
                        contour.max_z = contour.z[i];
                }
            }
        fclose(fp);
    }
    /*
     * rescale the contour information
     */
    for(i=0;i<contour.num_slices;i++)
    {
        contour.z[i] = [maxz-minz)*(contour.z[i] -
        contour.min_z)/(contour.max_z - contour.min_z) + minz +
        zm;
            for(j=0;j < contour.num_vert[i];j++)
            {
                contour.x[i][j] = minx + xm +
                    (maxx-minx)*(contour.x[i][j] -
                    contour.min_x)/(contour.max_x -
                    contour.min_x);
                contour.y[i][j] = miny + ym +
                    (maxy-miny)*(contour.y[i][j] -
                    contour.min_y)/(contour.max_y -
                    contour.min_y);
            }
    }
    contour.min_x = minx;
    contour.min_y = miny;
    contour.min_z = minz;
    contour.max_x = maxx+2*xm;
    contour.max_y = maxy+2*ym;
```

```
            contour.max_z = maxz+2*xm;
            /*
             * write the contour file
             */
            if ((fp = fopen(output."w")) == NULL)
            {
                    fprintf(stderr, " %s: can not open file %s\n", argv[0],
                    output);
                    exit[1];
            }
            fprintf(fp,"%g\n",(contour.min_x));
            fprintf(fp,"%g\n",(contour.min_y));
            fprintf(fp,"%g\n",(contour.min_z));
            fprintf(fp,"%g\n",(contour.max_x));
            fprintf(fp,"%g\n",(contour.max_y));
            fprintf(fp,"%g\n",(contour.max_z));
            fprintf(fp,"%d\n\n",(contour.num_slices));
            for (i=0;i < contour.num_slices; i ++)
            {
                    fprintf(fp."%d\n",(contour.num_vert[i]));
            }
            fprintf(fp,"\n");
            for(i=0;i<contour.num_slices;i++)
            {
                    fprintf(fp,"%g\n",(contour.z[i]));
                    for(j=0;j< contour.num_vert[i];j++)
                    {
                        fprintf(fp, " %g", (contour.x[i][j]));
                        fprintf(fp, " %g", (contour.y[i][j]));
                        if(((j+1) % 5) == 0)
                                fprintf(fp,"\n");
                    }
                    fprintf(fp, "\n");
            }
            fclose(fp);
            for(i=0;i<contour.num_slices;i++)
            {
                    sprint(sbuff,"%s_mat_%d", output,(i+1));
                    if ((fp = fopen(sbuff,"w")) == NULL)
                    {
                    fprintf(stderr, " %s: can not open file %s\n",
                    argv[0]m sbuff);
                    exit[1];
            }
            for(j=0;j< contour.num_vert[i];j++)
            {
                    fprintf(fp, " %g", (contour.x[i][j]));
                    fprintf(fp, " %g", (contour.y[i][j]));
                    fprintf(fp, " %g\n",(contour.z[i]));
            }
            fclose(fp);
        }
        exit(0);
}
#includes "includes.h"
#include "g3dplan.h"
SKELETON *add_node(s, y, z,r, helmet, first)
float x, y, z,r;
SKELETON *first;
int helmet;
{
    SKELETON *node = NULL, *new_node = NULL;
    new_node = (SKELETON *) calloc (1, sizeof(SKELETON));
    if(new_node == NULL)
    {
        fprintf(stderr, "add_node: alloc error for new node\n");
        return first;
    {
    new_node->prev = new_node->next = NULL;
    new_node->position.x = x;
    new_node->position.y = y;
    new_node->position.z = z;
    new_node->thickness = r;
    new_node->helmet = helmet;
    if(first != NULL)
    {
        node = first;
        while (node->next != NULL)
        {
```

```
                node = node->next;
            }
            node->next = new_node;
            new_node->prev = node;
        }
        else
        {
            first = new_node;
        }
        return first;
}
#include <stdio.h>
#include <string.h>
#include "g3dplan.h"
/*
 * title: atoil - ascii string to integer list
 *
 * descr: Converts input string to numbers and adds them to the
specified
 *       list, Syntax is as follows:
 *           n1          -    single number n1
 *           n1:n2       -    number range n1 to n2 by increment +1 or -1
 *           n1:n2:n3    -    number range n1 to n2 by increment n3
 *           n1,n2, ...  -    list of numbers
 *
 * usage: list = atoil(str,list)
 *
 * value: ILIST *list . . . pointer to output list
 *
 * parms:  char *str . . . input null-terminated string
 *         ILIST *list . . . pointer to input list
 *
 * notes:  1) If the input list in NULL, then a new list is set up.
 *         2) If there are illegal characters in the list, NULL is
returned.
 *         3) Or in case of any error, NULL is returned
 *
 */
#define LENGTH_MAX 128
static char check[ ] = "0123456789:-+,";
ILIST *atoil(char *str)
{
    int i, len, buffsize, n1, n2, n3, inc, *data = NULL;
    char buff[128];
    ILIST *list = NULL;
    char *idx=NULL, *rdx=NULL, *p1=NULL, *p2=NULL;
/*Check for empty string or illegal input characters*/
    len = strlen(str);
    if (len == 0)
            return((ILIST *)NULL);
    for (i=0; i<len; i++)
    {
            if (strch(check,str[i]) == NULL)
                    return(ILIST *)NULL);
    }
/*Create a new list necessary*/
    list = (ILIST *) calloc(1, sizeof(ILIST));
            return (ILIST *)NULL);
    list->n = 0;
    list->data = (int *) calloc(LENGTH_MAX, sizeof(int));
    if(list->data == NULL)
    {
            free(list);
            return (ILIST *)NULL;
    }
/*If there is a comma, the string must be a list of numbers n1,n2, ... */
    if (strchr(str,',') != NULL)
    {
      p1 = p2 = str;
      while (p1 < (str + len))
      {
        if ((p2 = strchr(p1,',')) == NULL)
          p2 = str + len;
        if (p2 != p1)
        {
          strncpy(buff,p1,p2-p1);
          buff[p2-p1] = '\0';
          if (list->n == LENGTH_MAX)
          {
```

```
            return list;
        }
        list->data[list->n] = atoi(buff);
        list->n += 1;
        p1 = p2 + 1;
    }
}
return(list);
}
/*Look for semicolon in text string*/
    idx = strchr(str,':');
    rdx = strrchr(str,':');
/*Single number n1*/
    if (idx == NULL)
    {
        if (sscanf(str,"%d",&n1) != 1)
        {
            free(list->data);
            free(list);
            return ((ILIST *)NULL);
        }
        list->data[0] = n1;
        list->n = 1;
        return list;
    }
/*Default increment range of numbers n1:n2*/
    if (idx!=NULL && idx==rdx)
    {
        if (sscanfistr,"%d:%d",&n1,&n2) != 2)
        {
            free(list->data);
            free(list);
            return ((ILIST *)NULL);
        }
        buffsize = abs(n2 - n1) + 1;
        inc = 0;
        if (n1 < n2) inc = 1;
        if (n1 > n2) inc = -1;
    }
/*Specified increment range of numbers n1:n2:n3*/
    if (idx != rdx)
    {
        if (sscanf(str,"%d:%d:%d",&n1,&n2,&n3) != 3)
        {
            free(list->data);
            free(list);
            return ((ILIST *NULL);
        }
        if (n3 == 0)
            buffsize = abs(n2-n1) + 1;
        else
            buffsize = abs((n2-n1)/n3) + 1;
        if (n1<n2 &&n3<0) n3 = -n3;
        if (n1>n2 && n3>0) n3 = -n3;
        inc = n3;
    }
    if(buffsize > LENGTH_MAX)
        buffsize = LENGTH_MAX;
    data = list->data;
    list->n = buffsize;
    for (i=0; i<buffsize; i++)
    {
       data[i] = n1 + i*inc;
    }
    return(list);
}
void FreeIlist(ILIST *1)
{
        if(1 == NULL)
                return;
        if(1->data != NULL)
                free(1->data);
        free[1];
}
/*
 * calc_shots problem: get the possible shots for one skeleton
 */
#include "includes.h"
#include "g3dplan_ui.h"
```

-continued

```
#include "g3dplan.h"
extern void display_status( );
extern SKELETON *add_node( );
extern void free_list( );
extern int mag3D( ), cutimg( );
extern int edtsk3d( );
extern SKELETON *delet_node( ), *delete_node( );
extern int shotsfromcross( );
extern int shotsfromend( );
extern int get_img_width( ), get_img_height( ), get_img_depth( );
extern int get_load_mag( ), get_stage( );
extern unsigned char *get_img( );
extern unsigned short *get_dist_img( );
extern void set_stage(int );
extern void sort_shots( );
int     calc_shots(shotlist,treeptr)
SHOT    **shotlist;
TREE    *treeptr;
{
    int     img_width = get_img_width( ),
            img_height = get_img_height( ),
            img_depth = get_img_depth( );   /* range of the image
            */
    int     load_mag = get_load_mag( );
    int     stage = get_stage( );
    unsigned char   *img = get_img( );
    unsigned short  *dist_img = get_dist_img( );
    int     shot_count=0, gofurther =0;
    int     i;
    unsigned char   *curimg=NULL;
    TREE    *tpt;
    SHOT    endpt;
    SKELETON        *skele=NULL,*sk4shot=NULL,*tsk=NULL,
    *endlist=NULL,  *crosspts=NULL;
    SKELETON        *newsk4shot= NULL, *tmpc=NULL;
    SKELETON        *compare=NULL, *tmplist=NULL;
    SKELETON        *end11=NULL, *end12=NULL;
    void    compfirstlevel( ), compllevelup( );
    float   x2,y1,z1,r1,x2, y2,z2,r2,dis, ax, ay,az, ar;
    int     n=1, ind;
    unsigned short  *s=NULL;
    curimg = (unsigned char
    *)calloc(img_height*img_width*img_depth, sizeof(unsigned
    char));
    if( !curimg)
    {
            fprintf(stderr,"calc_shots: cannot allocate memory for
            images\n");
            exit(1);
    }
    (void)mag3D(img,img_width,img_height,img_depth,curimg,1,1,1);
    tpt = treeptr;
    while( tpt->prev != NULL)
    {
        cutimg(curimg,tpt->shot);
        tpt = tpt->prev;
        /*
        tsk = add_node(tpt->shot.x, tpt->shot.y,
        tpt->shot.z,tpt->shot.r, 0, tsk);
        */
    }
    /*
    display_status(DISPLAY_ALL,curimg.tsk);
    free_list(tsk);
    */
    gofurther = edtsk3d(curimg, &endlist, &crosspts, &skele);
    GFree(curimg);
    if( !gofurther)
    {
        fprintf(stderr,"all the skeleton are less than **, no
        need to go further\n");
        free_list(endlist);
        free_list(skele);
        free_list(crosspts);
        return(0);
    }
/* currently, if we can find any crosspoints, then they are the
shotlist
 * if the crossliast is NULL, then we find largest endpoint, and search
```

```
 * all possible points from this end, we gothrough all the endpoint
until
 * we find one or return 0
 */
    if( crosspts != NULL)
    {
        shot_count = shotsfromcross(crosspts, &sk4shot);
        if( shot_count != 0)
                comp1levelup(treeptr,sk4shot);
        free_list(crosspts);
        crosspts = NULL;
        if( sk4shot)
        {
            tsk = sk4shot;
            fprintf(stderr, "       shotfromcross:\n");
            while(tsk)
            {
                fprintf(stderr,       (%4.1f %4.1f
                %4.1f &4.1f)\n*,
                    tsk->position.x,
                    tsk->position.y,
                    tsk->position.z,
                    tsk->thickness/load_mag);
                tsk = tsk->next;
            }
        }
    }
    if( sk4shot == NULL || shot_count == 0)
    {
        tsk = endlist;
        s = dist_img;
        while(tsk != NULL)
        {
            x1= tsk->position.x;
            y1= tsk->position.y;
            z1= tsk->position.z;
            r1 = tsk->thickness;
            ind = ((int)(z1)*img_height *(int)y1)*
            img_width + (int)x1;
            if( (float)fabs(r1*r1 - s(ind)) > (float)3)
                end11 = add_node(x1,y1,z1,r1, 0,
                    end11);
            else
                end12 = add_node(x1,y1,z1,r1, 0,
                    end12);
            tsk = tsk->next;
        }
        free_list(endlist);
        while(shot_count == 0 && end11 != NULL && skele !=
        NULL)
        {
            endpt.x = (end11->position).x;
            endpt.y = (end11->position).y;
            endpt.z = (end11->position).z;
            endpt.r = (end11->thickness);
            tsk = end11;
            while(tsk != NULL)
            {
                if( (tsk->thickness) > endpt.r)
                {
                    endpt.x = (tsk->position).x;
                    endpt.y = (tsk->position).y;
                    endpt.z = (tsk->position).z;
                    endpt.r = (tsk->thickness);
                }
                tsk = tsk->next;
            }
            shot_count = shotsfromend(endpt,
            skele,&sk4shot);
            if( shot_count !=0)
                compfirstlevel(treeptr,sk4shot);
            end11 = delete_node(endpt.x, endpt.y,
            endpt.z,endpt.r, end11, &tmpc);
        }
        free_list(end11);
        while(shot_count == 0 && end12 != NULL && skele !=
        NULL)
        {
            endpt.x = (end12->position).x;
```

```
            endpt.y = (end12->position).y;
            endpt.z = (end12->position).z;
            endpt.r = (end12->thickness);
            tsk = end12;
            while(tsk != NULL)
            {
                if( (tsk->thickness) > endpt.r)
                {
                    endpt.x = (tsk->position).x;
                    endpt.y = (tsk->position).y;
                    endpt.z = (tsk->position).z;
                    endpt.r = (tsk->thickness);
                }
                tsk = tsk->next;
            }
            shot_count = shotsfromend(endpt,
            skele,&sk4shot);
            if( shot_count !=0)
                compfirstlevel(treeptr,sk4shot);
            end12 = delet_node(endpt.x, endpt.y, endpt.z,
            endpt.r, end12, &tmpc);
        }
        free_list(end12);
        fi( sk4shot)
        {
            tsk = sk4shot;
            fprintf(stderr, "     shotsfromend:\n");
            while(tsk)
            {
                fprintf(stderr,"     (%4.1f %4.1f
                %4.1f %4.1f)\n",
                tsk->position.x, tsk->position.y,
                tsk->position.z,
                tsk->thickness/load_mag);
                tsk.luk->nexl;
            }
        }
    }
    free_list(skele);
    if(shot count - 0)
    {
        return(shot_count);
    }
    (*shotlist) = (SHOT *)calloc(shot_count.sizeof(SHOT));
    tsk=sk4shot;
    for(i=0,i< shot_count:i++)
    {
        if(tsk !=NULL)
        {
            (*shotlist)[i].x=(tsk->position).x;
            (*shotlist)[i].y=(tsk->position).y;
            (*shotlist)[i].z=(tsk->position).z;
            (*shotlist)[i].r=tsk->thickness;
            tsk=tsk->next;
        }
        else
        {
            printf("OHAH, the shot_count != num of sk4shot
            !\n");
            free_list(sk4shot);
            exit(1);
        }
    }
    /* sort the shotlist: larerget shot first i, helps to
        determine "stop" earlier */
    sort_shots(*shotlist, shot_count);
    fprintf(stderr,"shots new order\n");
    for(i=0; i<shot_count;i++)
    {
        fprintf(stderr,"     (%4.1f %4.1f %4.1f %4.1f)\n",
        (*shotlist)[i].x, (*shotlist)[i].y,
        (*shotlist)[i].z, (*shotlist)[i].r);
    }
    free_list(sk4shot);
    return(shot_count);
}
void comp1levelup(cur_ptr, list)
TREE *cur_ptr;
SKELETON *list;
```

```
{
    int i, j, checkpoint;
    TREE *tptr, *h1, *p1;
    double x,y,z,d;
    void free_branch( );
    SKELETON *sptr;
    int load_mag = get_load_mag( );
    if(cur_ptr ==NULL)
        return;
    p1 = cur_ptr;
    if(p1 != NULL && p1->prev != NULL &&
    p1->prev->prev != NULL)
    {
        h1 = p1->prev;
    }
    else
    {
        return;
    }
    checkpoint = 0;
    while(h1->next(checkpoint) != p1 && checkpoint <
    h1->next_count)
        checkpoint ++;
    sptr = list;
    while (sptr != NULL)
    {
        for(i=checkpoint+1;i < h1->next_count; i++)
        {
            tptr = h1->next[i];
            x = sptr->position.x - tptr->shot.x;
            y = sptr->position.y - tptr->shot.y;
            z = sptr->position.z - tptr->shot.z;
            d = x*x +y*y+ z*z;
            if( d < (double)(RMIN*0.6*load_mag))
            {
                free_branch(tptr);
                h1->next_count = h1->next_count-1;
                for(j=i; j<h1->next_count; j++)
                {
                    h1->next[j] = h1->next[j+1];
                }
            }
        }
        sptr = sptr->next;
    }
}
/*
 * function to delete a branch
 */
void free_branch(bptr)
TREE *bptr;
{
    int i;
    void free_branch( );
    if(bptr == NULL)
        return;
    if(bptr->next_count > 0)
    {
        for(i=0;i< (bptr->next_count);i++)
            free_branch(bptr->next[i]);
    }
    else
    {
        GFree(bptr);
    }
}
void compfirstlevel(cur_ptr, list)
TREE *cur_ptr;
SKELETON *list;
{
    int i, j, checkpoint;
    TREE *tptr, *h1, *p1;
    double x,y,z,d;
    void free_branch( );
    SKELETON *sptr;
    int load_mag = get_load_mag( );
    if(cur_ptr ==NULL)
        return;
    p1 = cur_ptr;
```

```
        while(p1 != NULL && p1->prev != NULL && p1->prev->prev !=
        NULL)
        {
            p1 = p1->prev;
        }
        h1 = p1->prev;
        checkpoint = 0;
        while(h1->next(checkpoint) != p1 && checkpoint <
        h1->next_count)
            checkpoint ++;
        sptr = list;
        while (sptr != NULL)
        {
            for(i=checkpoint+1;i < h1->next_count; i++)
            {
                tptr = h1->next[i];
                x = sptr->position.x - tptr->shot.x;
                y = sptr->position.y - tptr->shot.y;
                z = sptr->position.z - tptr->shot.z;
                d = x*x +y*y+ z*z;
                if( d < (double) (RMIN*0.6*load_mag))
                {
                    free_branch(tptr);
                    h1->next_count = h1->next_count-1;
                    for(j=i; j<h1->next_count; j++)
                    {
                        h1->next[j] = h1->next[j+1];
                    }
                }
            }
            sptr = sptr->next;
        }
}
/*
 * g3dplan.c - Notify and event callback functions and main( )
 */
#include "includes.h"
#include "g3dplan_ui.h"
#include "g3dplan.h"
/*
 * Notify callback function for 'load'.
 */
void
load_callback(Panel_item item, Event *event)
{
    g3dplan_main_window_objects *ip =
    (g3dplan_main_window_objects
    *) xv_get(item, XV_KEY_DATA, INSTANCE);
    void load_contour( );
    load_contour( );
}
/*
 * Notify callback function for 'fill_contour'.
 */
void
fill_contour_callback(Panel_item item, Event *event)
{
    g3dplan_main_window_objects *ip =
    (g3dplan_main_window_objects
    *) xv_get(item, XV_KEY_DATA, INSTANCE);
    extern void fill_contour( );
    fill_contour( );
}
/*
 * Notify callback function for 'thining'.
 */
void
thining_callback(Panel_item item, Event *event)
{
    g3dplan_main_window_objects *ip =
    (g3dplan_main_window_objects
    *) xv_get(item, XV_KEY_DATA, INSTANCE);
    extern void thining( );
    thining( );
}
/*
 * Notify callback function for 'display_update'.
 */
void
```

-continued

```
display_update_callback(Panel_item item, Event *event)
{
    g3dplan_main_window_objects *ip =
    (3dplan_main_window_objects
    *) xv_get(item, XV_KEY_DATA, INSTANCE);
    fputs("g3dplan: display_update_callback\n", stderr);
    /* gxv_start_connection DO NOT EDIT THIS SECTION */
    /* gxv_end_connections */
}
/*
 * Notify callback function for 'step'.
 */
void
step_callback(Panel_item item, Event *event)
{
    extern void step_thru( );
    g3dplan_main_window_objects *ip =
    (g3dplan_main_window_objects
    *) xv_get(item, XV_KEY_DATA, INSTANCE);
    fputs("g3dplan: step_callback\n", stderr);
    step_thru( );
}
/*
 * Notify callback function for 'make_shots'.
 */
void
make_shots_callback(Panel_item item, Event *event)
{
    extern void make_shots( );
    g3dplan_main_window_objects *ip =
    (g3dplan_main_window_objects
    *) xv_get(item, XV_KEY_DATA, INSTANCE);
    fputs("g3dplan: make_shots_callback\n", stderr);
    make_shots( );
}
/*
 * Notify callback function for 'show_plan'.
 */
void
show_plan_callback(Panel_item item, Event *event)
{
    g3dplan_main_window_objects *ip =
    (g3dplan_main_window_objects
    *) xv_get(item, XV_KEY_DATA, INSTANCE);
    fputs("g3dplan: show_plan_callback\n", stderr);
    /* gxv_start_connections DO NOT EDIT THIS SECTION */
    /* gxv_end_connections */
}
/*
 * Notify callback function for 'show_3d'.
 */
void
show_3d_callback(Panel_item item, Event *event)
{
    extern void show_3d_window( );
    show_3d_window( );
}
/*
 * Notify callback function for 'plus'.
 */
void
plus_callback(Panel_item item, Event *event)
{
    extern void plus_slice( );
    plus_slice( );
}
/*
 * Notify callback function for 'minus'.
 */
void
minus_callback(Panel_item item, Event *event)
{
    extern void minus_slice( );
    minus_slice( );
}
/*
 * Notify callback function for 'skeleton'.
 */
void
```

-continued

```
skel_callback(Panel_item item, Event *event)
{
    extern void make_skeleton( );
    fputs("g3dplan: skel_callback\n", stderr);
    make_skeleton( );
}
/*
 * Notify callback function for 'add_shots'.
 */
void
add_shots_callback(Panel_item item, Event *event)
{
    extern void add_shots( );
    fputs("g3dplan: add_shots_callback\n", stderr);
    add_shots( );
}
/*
 * Notify callback function for 'stage'.
 */
void
stage_callback(Panel_item item, Event *event)
{
    extern int get_stage( );
    g3dplan_main_window_objects *ip =
    (g3dplan_main_window_objects
    *) xv_get(item, XV_KEY_DATA, INSTANCE);
    int stage = get_stage( );
    char str(64);
    if(stage == 1)
        stage = 2;
    else
        stage = 1;
    set_stage(stage);
    sprintf(str,"Stage (%d)", stage);
    xv_set(ip->stage, PANEL_LABEL_STRING, str, NULL);
}
/*
 * Notify callback function for 'cancel'.
 */
void
cancel_callback(Panel_item item, Event *event)
{
    extern void cancel( );
    fputs("g3dplan: cancel_callback\n", stderr);
    cancel_last_shot( );
}
/*
 * Notify callback function for 'display_3d'.
 */
void
display_3d_callback(Panel_item item, Event *event)
{
    extern void display_3d( ), display_box( );
    extern unsigned char *get_tmp_img( );
    unsigned char *img = get_tmp_img( );
    fputs("g3dplan: display_3d_callback\n", stderr);
    if( !img)
        fputs("display_3d: NULL img", stderr);
    else
    {
        display_3d(DISPLAY_IMAGE, img);
        display_box( );
    }
}
/*
 * main window's window destruction notifier
 */
Notify_value main_window_destroy(client, status)
Notify_client client;
Destroy_status status;
{
    char *get_prog_name( );
    extern void GFree(char *), free_list(SKELETON *),
    FreeContour(void);
    extern unsigned char *get_img(void);
    extern unsigned char *get_tmp_img(void);
    extern SKELETON *get_first_skelet(void);
    extern unsigned short *get_dist_img(void);
    extern CONTOUR get_contour(void);
```

-continued

```
        void set_img(unsigned char *);
        void set_dist_img(unsigned short *);
        void set_first_skelet(SKELETON *);
        unsigned char *ptr;
        unsigned short *sptr;
        SKELETON *sk;
if(status == DESTROY_CHECKING)
{
/*
        put memory frees here
*/
        ptr = get_img( );
        GFree((char *)ptr);
            set_img(NULL);
            ptr = get_tmp_img( );
            GFree((char *)ptr);
            set_tmp_img(NULL);
            sptr = get_dist_img( );
            GFree((char *)sptr);
            set_dist_img(NULL);
            sk = get_first_skelet( );
            free_list(sk);
            set_first_skelet(NULL);
            FreeContour( );
            printf("%s: quitting with memory cleanup . . . \n", (char
            *)get_prog_name( ));
        }
        else if (status == DESTROY_CLEANUP)
            return notify_next_destroy_func(client, status);
        return NOTIFY_DONE;
}
/*
 * sub window's window destruction notifier
 */
Notify_value sub_window_destroy(client, status)
Notify_client Client;
Destroy_status status;
{
        g3dplan_main_window_objects *get_main_window_objects( );
        g3dplan_main_window_objects *main_win =
        get_main_window_objects( );
        if(status == DESTROY_CHECKING)
        {
            xv_set(main_win->show_3d, PANEL_LABEL_STRING,
                        "Show 3D View", NULL);
            notify_veto_destroy(client);
        }
        else if (status == DESTROY_CLEANUP)
            return notify_next_destroy_func(client, status);
        return NOTIFY_DONE;
}
SKELETON *copylist(list)
SKELETON *list;
{
    SKELETON *new=NULL;
    if(!list)
        return(list);
    while(list->prev)
        list = list->prev;
    while(list)
    {
        new = add_node((list->position).x (list->position).y,
        (list->position).z, list->thickness, list->helmet,
        new);
        list = list->next;
    }
    return(new);
}
/*
 * cutimg: cut img from a given shot
 *          be careful here, the load_mag from where the shot is
defined
 *          should be the same as drawing here
*/
#include "includes.h"
#include "g3dplan_ui.h"
#include "g3dplan.h"
extern int get_img_width( ), get_img_height( ),
get_img_depth( ),get_img_depth( ), get_load_mag( );
```

```
-continued extern short *get_dist_img( );
cutimg(inimg,shot)
unsigned char  *inimg;
SHOT shot;
{
        int     row, col.dep.i = 0;
        int     min_x, max_x, min_y, max_y, min_z, max_z;
        float   d,r, dx, dy,dz, real_r;
        int     offset=3; /* I just put some margin to make things
        safer */
        int     img_width = get_img_width( ),
                img_height = get_img_height( ),
                img_depth = get_img_depth( ),
                load_mag = get_load_mag( );     /* range of the
                image */
        short   *s = get_dist_img( );
        r = shot.r;
        if( r == 0.0)
                return;
        if( (float)fabs(s[i] - r*r) > 5) /* this means shots is
        inside region */
        {
                real_r = r + 0.8*load_mag;
                if( r >= (R18[0]=load_mag))
                        real_r += 0.5*load_mag;
                else if( r <= (R18[1]*load_mag) && r >=
                (R18[0]=load_mag))
                        real_r += 0.5*load_mag*(r/load_mag -
                        R18[0])/(R18[1]-R18[0]);
                else if( r < (R18[0]*load_mag) && r >
                (R14[1]*load_mag))
                        real_r += 0.5*load_mag;
                else if( r <= (R14[1]*load_mag) && r >=
                (R14[0]*load_mag))
                        real_r += 0.5*load_mag*(r/load_mag -
                        R14[0])/(R14[1]);
                else if( r < (R1410)*load_mag) && r > (R8[1]*load_mag))
                        real_r += 0.5*load_mag;
                else if( r <= (R8[1]*load_mag) && r >=
                (R8[0]*load_mag))
                        real_r += 0.5*load_mag*(r/load_mag -
                        R8[0])/(R8[1]-R8[0]);
                else
                        real_r += 0.2*load_mag;
        }
        else if( r >= (R18[0]*load_mag))
                real_r = r + 1.2*load_mag;
                else if(r <= (R18[1]*load_mag)&&r >= (R18[0]*load_mag))
                        real_r = r + 1.2*load_mag * (r/load_mag -
                        R18[0])/(R18[1] - R28[0]);
                else if( r < (R18[0]*load_mag) && r > (R14[1]*load_mag))
                        real_r = r + 1.5*load_mag;
                else if(r <= (R14[1]*load_mag)&&r >= (R14[0]*load_mag))
                        real_r = r + 0.8*load_mag * (r/load_mag -
                        R14[0])/(R14[1] - R14[0]);
                else if (r < (R14[0]*load_mag) && r > (R8[1]*load_mag))
                        real_r = r + 1.3*load_mag;
                else if( r <= (R8[1]*load_mag) && r >= (R8[0]*load_mag))
                        real_r = r + 0.8*load_mag* (r/load_mag - R8[0])/
                        (R8[1] - R8[0]);
                else
                        real_r = r + 0.4*load_mag;
        min_x = shot.x - real_r - offset;
        if(min_x < 0)
                min_x = 0;
        max_x = shot.x + real_r + offset;
        if(max_x > (img_width - 1))
                max_x = img_width - 1;
        min_y = shot.y - real_r - offset;
        if(min_y < 0)
                min_y = 0;
        max_y = shot.y + real_r + offset;
        if(max_y > (img_height - 1))
                max_y = img_height - 1;
        min_z = shot.z - real_r - offset;
        if(min_z < 0)
                min_z = 0;
        max_z = shot.z + real_r + offset;
        if(max_z > (img_depth - 1))
```

```
                    max_z = img_depth - 1;
                for(dep=min_z;dep <= max_z; dep++)
                {
                    for(row=min_y;row >= max_y; row++)
                    {
                        for(col= min_x; col >= max_x; col++)
                        {
                            i = (dep*img_height+row) * img_width +
                            col;
                            dx = (fabs((double)((float)col -
                            shot.x));
                            dy = fabs((double)((float)row -
                            shot.y));
                            dz = fabs((double)((float)dep -
                            shot.z));
                            d =
                            (float)sqrt((double)(dx*dx+dy*dy+dz*dz));
                            if( d <= (real_r))
                            {
                                inimg[i] = 0;
                            }
                        }
                    }
                }
                return;
            }
/*
*delet_node: delete the matching node
*/
#include "includes.h"
#include "g3dplan_ui.h"
#include "g3dplan.h"
extern void free_list( ), GFree( );
/*
* delete s node from the linked list with radius r and position x,y,z
* from the list pointed to by first (its the first node in the list).
*
* it will return the list's new first pointer after deletion as
* well as the next node after deletion in "next"
*/
SKELETON *delet_node(x,y,z,r,first,next)
float   x,y,z,r;
SKELETON *first;
SKELETON **next;
{
    SKELETON *node = NULL, *del_node = NULL;
    int node_found = 0;
    if(first == NULL)
    {
        fprintf(stderr,"delet_node: NULL List passed\n");
        return(first);
    }
    if(next == NULL)
    {
        fprintf(stderr,"delet_node: NULL pointer passed for
        next node\n");
        return(first);
    }
    /*
     * check if the node exists in that list and locate it
     */
    node = first;
    while (!node_found && node != NULL)
    {
        if(node->position.x == x && node->position.y == y &&
        node->position.z == z)
            node_found = 1;
        else
            node = node->next;
    }
    if(!node_found)
    {
        fprint(stderr."delet_node: node at (%g,%g,%f) with
        r(%g) does not exist\n",
            x, y, z, r);
        return(first);
    }
    del_node = node;
    if(del_node == first)
```

```
        {
            *next = first = del_node->next;
            if(first)
                first->prev = NULL;
            GFree(del_node);
            del_node = NULL;
        }
        else if (del_node->next == NULL)
        {
            node = del_node->prev;
            *next = NULL;
            if(node)
                node->next = NULL;
            free(del_node);
        }
        else
        {
            node = del_node->prev;
            *next = node->next = del_node->next;
            (del_node->next)->prev = node;
            GFree(del_node);
            del_node = NULL;
        }
        return(first);
}
/*
 * modified version of delet_node( ) which takes
 * pointer to the node as the address of node to
 * be deleted from a list with starting node
 * given by first, and it returns the address
 * of the first node in the modified list and
 * the address of the next node to the deleted
 * node
 */
SKELETON *delete_node(node,first,next)
SKELETON *node, *first, **next;
{
    SKELETON *np = NULL;
    int node_found = 0;
    /*
     * check for valid input
     */
    if(first == NULL || node == NULL || next == NULL )
    {
        fprintf(stderr,"delet_node: NULL List/Node/Next
        passed\n");
        return(first);
    }
    /*
     * check if the node exists in that list
     */
    np = first;
    node_found = (np == node);
    while (!node_found && np != NULL)
    {
        if(node == np)
            node_found = 1;
        else
            np = np->next;
    }
    if(!node_found)
    {
        fprintf(stderr,"delet_node: node not in the list\n");
        return(first);
    }
    /*
     * now delete that node
     */
    if(node == first) /* node is the first node in the list */
    {
        *next = first = node->next;
        if(first)
            first->prev = NULL;
        GFree(node);
    }
    else if (node->next == NULL) /* node is the last node in the
    list */
    {
        np = node->prev;
```

```
                *next = NULL;
                if(np)
                        np->next = NULL;
                free(node);
        }
        else /* node is somewhere in the middle of the list */
        {
                np = node->prev;
                *next = np->next = node->next;
                (*next)->prev = np;
                GFree(node);
        }
        return(first);
}
/*
 * processing routines for g3dplan:
 * display_3d.c
 *
 */
#include "includes.h"
#include "g3dplan_ui.h"
#include "g3dplan.h"
extern g3dplan_sub_window_objects   *get_sub_window_objects( );
extern g3dplan_main_window_objects *get_main_window_objects( );
extern char *get_prog_name( );
extern int   get_img_width( ), get_img_height( ), get_img_depth( );
extern void GFree( );
/* X display variables */
extern visual *get_visual( );
extern Display *get_display( );
extern Colormap get_colormap( );
extern Window   get_paint_window( ), get_sub_paint_window( );
extern GC   get_sub_gc( );
extern unsigned long get_black_pixel( ), get_white_pixel( ),
get_red_pixel( ), get_blue_pixel( ),
                        get_orange_pixel( ), get_yellow_pixel( );
                        get_green_pixel( ), get_gray_start_pixel( ),
extern int      set_sub_canvas_height(int), set_sub_canvas_width(int);
extern int      get_depth( );
extern float   get_view_vmin( ), get_view_vmax( ), get_view_umin( ),
get_view_umax( );
extern void    set_view_vmin(float), set_view_vmax(float),
set_view_umin(float), set_view_umax(float);
extern CONTOUR get_contour( );
extern SKELETON *get_first_skelet( );
/* matrix variables and functions */
extern matrix M; /* transform matrix */
void tr_matrix(float, float, float, float, float, float);
void get_view(float *, float *, float, float, float, float);
void set_view_range(int,int,int);
void print_matrix( );
/*
 * display_3d:
 *
 * display status displays image/skeleton/all depending on the
arguments
 *
 * the first argument in the variable list is the display type :
 *
 *    DISPLAY_IMAGE, then next argument is the address of the image
 *    DISPLAY_ALL has one more additional argument, the address of
skeleton data.
 *
 */
void display_3d(int display_type . . . )
{
    va_list arg:
    g3dplan_main_window_objects  *main_win =
    get_main_window_objects( );
    g3dplan_sub_window_objects   *sub_win =
    get_sub_window_objects( );
    char *prog_name = get_prog_name( );
    Visual *visual = get_visual( );
    Display *display = get_display( );
    Colormap cmap = get_colormap( );
    Window  sub_paint_window = get_sub_paint_window( );
    GC   sub_gc = get_sub_gc( );
    unsigned    long black_pixel = get_black_pixel( ),
                white_pixel = get_white_pixel( ),
```

```
            red_pixel = get_red_pixel( ),
            yellow_pixel = get_yellow_pixel( ),
            green_pixel = get_green_pixel( ),
            orange_pixel = get_orange_pixel( ),
            blue_pixel = get_blue_pixel( );
int sub_canvas_height = get_sub_canvas_height( ),
    sub_canvas_width = get_sub_canvas_width( );
int depth = get_depth( );
int disp_mag;
int img_w = get_img_width( ),
    img_h = get_img_height( ),
    img_d = get_img_depth( );
SKELETON *skeleton_start = get_first_skelet( );
SKELETON *node = NULL;
CONTOUR contour = get_contour( );
unsigned char *buf = NULL;
int w,d,h,iw,id,ih index;
int x1, y1, x2, y2, rm;
float alpha, beta, gamma, X, Y, Z;
float u,v,umin,vmin,umax,vmax;
unsigned char *image = NULL;
/* get the arguments */
if(display_type == DISPLAY_SKELETON)
{
    va_start(arg, display_type);
    skeleton_start = va_arg(arg, SKELETON *);
    if(skeleton_start == NULL)
    {
        xv_set(sub_win->sub_window,
        FRAME_LEFT_FOOTER,
            "display_3d: ERROR -> NULL Skeleton
            passed", NULL);
        XBell(display, 0);
        return;
    }
}
else if(display_type == DISPLAY_IMAGE || display_type ==
DISPLAY_ALL )
{
    va_start(arg, display_type);
    image = (unsigned char *)va_arg(arg, unsigned char *);
    if(image == NULL)
    {
        xv_set(sub_win->sub_window,
        FRAME_LEFT_FOOTER,
            "display_3d: ERROR -> NULL image
            passed", NULL);
        XBell(display, 0);
        return;
    }
    if(display_type == DISPLAY_ALL)
    {
        skeleton_start = va_arg(arg, SKELETON *);
        if(skeleton_start == NULL)
        {
            va_end(arg);
            xv_set(sub_win->sub_window,
            FRAME_LEFT_FOOTER,
                    "display_3d: ERROR ->
                    NULL skeleton passed",
                    NULL);
            XBell(display, 0);
            return;
        }
    }
}
else
{
    xv_set(sub_win->sub_window, FRAME_LEFT_FOOTER,
        "display_3d: ERROR -> Unknown type (Check
        Program)", NULL);
    XBell(display, 0);
    return;
}
/* now the display part :-) */
xv_set(sub_win->sub_window,
FRAME_LEFT_FOOTER, "display_3d:
display . . . ", NULL);
XClearWindow(display, sub_paint_window);
```

```
disp_mag = (int) xv_get(main_win->display_mag,
PANEL_VALUE);
XFlush(display);
/* image */
if ((display_type == DISPLAY_IMAGE) || (display_type ==
DISPLAY_ALL))
{
    XSetBackground(display, sub_gc, black_pixel);
    XSetForeground(display, sub_gc, white_pixel);
    XSetWindowBackground(display, sub_paint_window,
    black_pixel);
    alpha = (float)((int)xv_get(sub_win->alpha,
    PANEL_VALUE));
    beta = (float)((int)xv_get(sub_win->beta,
    PANEL_VALUE));
    gamma = (float)((int)xv_get(sub_win->gamma,
    PANEL_VALUE));
    X = (float)((int)xv_get(sub_win->x, PANEL_VALUE));
    Y = (float)((int)xv_get(sub_win->y, PANEL_VALUE));
    Z = (float)((int)xv_get(sub_win->z, PANEL_VALUE));
    tr_matrix((float)alpha, (float)beta, (float)gamma,
        (float)(X-img_w/2),(float)(Y-img_h/2_,(float)(Z-img_d/2));
    /* get vmin, umin, from the 8-point limit of the volume
    */
    set_view_range(img_w, img_h, img_d);
    vmin = get_view_vmin( );
    umin = get_view_umin( );
    vmax = get_view_vmax( );
    umax = get_view_umax( );
    x1 = MARGIN;
    y1 = MARGIN;
    x2 = (floor)((double)(disp_mag*(vmax-vmin+0.5)));
    y2 = (floor)((double)(disp_mag*(umax-umin+0.5)));
    xv_set(sub_win->sub_canvas,  CANVAS_WIDTH,
                                 x2+4*MARGIN,
                                 CANVAS_HEIGHT,
                                 y2+4*MARGIN,
                                 NULL);
    XSetBackground(display, sub_gc, black_pixel);
    XSetForeground(display, sub_gc, green_pixel);
    XSetWindowBackground(display, sub_paint_window,
    black_pixel);
    XDrawRectangle(display, sub_paint_window, sub_gc, x1,
    y1, x2, y2);
    XFlush(display);
    /* contours */
    XSetBackground(display, sub_gc, black_pixel);
    XSetForeground(display, sub_gc, blue_pixel);
    for(d=0; d< contour.num_slices; d++)
    {
      for(h=0; h<contour.num_vert(d): h++)
      {
          w = (h+1) % (contour.num_vert[d]);
          X = (float) contour.x[d][h];
          Y = (float) contour.y[d][h];
          Z = (float) contour.z[d];
          get_view(&,&u,X,Y,Z);
          x1 = MARGIN + (floor((double)(disp_mag*(v-vmin
          +0.5))));
          y1 = MARGIN + (floor((double)(disp_mag*(u-umin
          +0.5))));
          X = (float) contour.x[d][w];
          Y = (float) contour.y[d][w];
          Z = (float) contour.z[d];
          get_view(&v,&u,X,Y,Z);
          x2 = MARGIN + (floor(double)(disp_mag*(v-vmin
          + 0.5))));
          y2 = MARGIN + (floor(double)(disp_mag*(u-umin
          + 0.5))));
          XDrawLine(display, sub_paint_window, sub_gc,
          x1, y1, x1, y2);
      }
    }
    /* skeleton */
    if(skeleton_start != NULL)
    {
        node = skeketon_start;
        while( node != NULL)
        {
```

```
                    rm = (floor((double)(disp_mag *
                        (node->thickness +0.5))));
                    X = (float) node->position.x;
                    Y = (float) node->position.y;
                    Z = (float) node->position.z;
                    get_view(&v,&u,X,Y,Z);
                    x2 = MARGIN +
                        (floor((double)(disp_mag*(v-min +
                        0.5))));
                    y2 = MARGIN +
                        (floor((double)(disp_mag*(u-umin +
                        0.5))));
                    x1 = x2 - rm;
                    y1 = y2 - rm;
                    XSetForeground(display, sub_gc,
                        green_pixel));
                    XDrawArc(display, sub_paint_window,
                        sub_gc, x1, y1, (2*rm), (2*rm), 0,
                        (64*360));
                    XSetForeground(display, sub_gc,
                        orange_pixel);
                    XDrawLine(display, sub_paint_window,
                        sub_gc, x2-5, y2, x2+5, y2);
                    XDrawLine(display, sub_paint_window,
                        sub_gc, x2, y2-5, x2, y2+5);
                    node = node->next;
                }
            }
            /* image */
            XSetBackground(display, sub_gc, black_pixel);
            XSetForeground(display, sub_gc, yellow_pixel);
            index =0;
            for(d=0; d< img_d; d++)
            {
                for(h=0, h<img_h; h++)
                {
                    for(w=0; w<img_w; w++)
                    {
                        if(image[index] != 0)
                        {
                            for(id=0;id<disp_mag;id++)
                            {
                                for(ih=0;ih<disp_mag;ih++)
                                {
                                    for(iw=0;iw>disp_mag;iw++)
                                    {
                                        X = (float)w +
                                            (float)iw/(float)disp_mag;
                                        Y = (float)h +
                                            (float)ih/(float)disp_mag;
                                        Z = (float)d +
                                            (float)id/(float)disp_mag;
                                        get_view(&v,&u,X,Y,Z);
                                        x2 = MARGIN +
                                            (floor((double)(disp_mag*(v-min +
                                            0.5))));
                                        y2 = MARGIN +
                                            (floor((double)(disp_mag*(u-min +
                                            0.5))));
                                        XDrawPoint(display, sub_paint_window,
                                            sub_gc, x2, y2);
                                    }
                                }
                            }
                        }
                        index ++;
                    }
                }
            }
            XSetBackground(display, sub_gc, black_pixel);
            XSetForeground(display, sub_gc, green_pixel);
            XFlush(display);
        }
        if (display_type == DISPLAY_SKELETON) || (display_type ==
        DISPLAY_ALL))
        {
        }
    return;
}
```

-continued

```
/*
 * 3D View window status change
 */
void show_3d_window( )
{
    g3dplan_sub_window_objects   *sub_win =
    get_sub_window_objects( );
    g3dplan_main_window_objects  *main_win =
    get_main_window_objects( );
    if((int)xv_get(sub_win->sub_window, XV_SHOW))
    {
        XV_Set(sub_win->sub_window,
        XV_SHOW, FALSE, NULL);
        xv_set(main_win->show_3d, PANEL_LABEL_STRING,
            "Show 3D View", NULL);
    }
    else
    {
        XV_Set(sub_win->sub_window,
        XV_SHOW, FALSE, NULL);
        xv_set(main_win->show_3d, PANEL_LABEL_STRING,
            "Hide 3D View", NULL);
    }
}
void set_view_range(int img_w, int img_h, int img_d)
{
    float u=0.0, v=0.0, vmin=0.0, vmax=0.0, umin=0.0,
    umax=0.0;
    get_view(&v, &u, (float)0, (float)0, (float)0);
    vmin = v;
    umin = u;
    vmax = v;
    umax = u;
    get_view(&v, &u,(float)img_w-1,(float)0,(float)0);
    if( v < vmin) vmin = v;
    if( u < umin) umin = u;
    if( v > vmax) vmax = v;
    if( u > umax) umax = u;
    get_view(&v,
        &u,(float)img_w-1,(float)img_h-1,(float)0);
    if( v < vmin) vmin = v;
    if( u < umin) umin = u;
    if( v > vmax) vmax = v;
    if( u > umax) umax = u;
    get_view(&v,
        &u,(float)img_w-1,(float)img_h-1,(float)img_d-1);
    if( v < vmin) vmin = v;
    if( u < umin) umin = u;
    if( v > vmax) vmax = v;
    if( u > umax) umax = u;
    get_view(&v,
        &u,(float)img_w-1,(float)0,(float)img_d-1);
    if( v < vmin) vmin = v;
    if( u < umin) umin = u;
    if( v > vmax) vmax = v;
    if( u > umax) umax = u;
    get_view(&v, &u,(float)0,(float)img_h-1,(float)0);
    if( v < vmin) vmin = v;
    if( u < umin) umin = u;
    if( v > vmax) vmax = v;
    if( u > umax) umax = u;
    get_view(&v,
        &u,(float)0,(float)img_h-1,(float)img_d-1);
    if( v < vmin) vmin = v;
    if( u < umin) umin = u;
    if( v > vmax) vmax = v;
    if( u > umax) umax = u;
    get_view(&v, &u,(float)0,(float)0,(float)img_d-1);
    if( v < vmin) vmin = v;
    if( u < umin) umin = u;
    if( v > vmax) vmax = v;
    if( u > umax) umax = u;
    set_view_vmin(vmin);
    set_view_umin(umin);
    set_view_vmax(vmax);
    set_view_umax(umax);
}
/*
 * processing routines for g3dplan:
```

-continued

```c
 * display_3d.c
 *
 */
#include "includes.h"
#include "g3dplan_ui.h"
#include "g3dplan.h"
extern g3dplan_sub_window_objects   *get_sub_window_objects( );
extern g3dplan_main_window_objects *get_main_window_objects( );
extern g3dplan_window_array_objects *get_window_array_pointer( );
extern char *get_prog_name( );
extern   get_img_width( ); get_img_height( ); get_img_depth( );
extern CONTOUR get_contour( );
extern void GFree( );
/* X display variables */
extern Display *get_display( );
extern Visual *get_visual( );
extern Colormap get_colormap( );
extern Window   get_paint_window( ), get_sub_paint_window( );
extern GC   get_gc( );
extern unsigned long get_black_pixel( ), get_white_pixel( ),
get_red_pixel( ),
                         get_yellow_pixel( ), get_green_pixel( ),
                         get_gray_start_pixel( );
extern int      set_sub_canvas_height(int), set_sub_canvas_width(int);
extern int      get_depth( );
extern void     free_window_array( );
extern int      get_destroy_override( );
extern g3dplan_window_array_objects *get_window_array_pointer( );
extern Notify_value array_window_destroy(Notify_client,
Destroy_status);
extern float get_weighting( );
extern float get_drawr( );
int make_window_array(int count)
{
    g3dplan_window_array_objects *array =
    get_window_array_pointer( );
    g3dplan_main_window_objects   *main_win =
    get_main_window_objects( );
    Display *display = get_display( );
    int i, j;
    unsigned long black_pixel = get_black_pixel( );
    Xv_opaque           window_image;
    static unsigned short  window_bits( ) = (
#include "g3dplan.icon"
    );
    Icon icon;
    Xv_Window paint_xv_window;
    char title(64);
    if(count < 1)
        return (0);
    if(array->count > 0 && array->count == count)
        return (1);
    if(array->count > 0)
        free_window_array( );
    array->window = (Frame *) calloc(count, sizeof(Frame));
    if(array->window == NULL)
        return (0);
    array->canvas = (Canvas *) calloc(count, sizeof(Canvas));
    if(array->canvas == NULL)
    {
        free(array->window);
        array->window = NULL;
        return (0);
    }
    array->paint_window = (Window *) calloc(count, sizeof(Window));
    if(array->paint_window == NULL)
    {
        free(array->window)
        array->window = NULL;
        free(array->canvas);
        array->canvas = NULL;
        return (0);
    }
    array->count = count;
    window_image = xv_create(XV_NULL, SERVER_IMAGE,
        SERVER_IMAGE_DEPTH 1,
        SERVER_IMAGE_BITS, window_bits,
        XV_WIDTH, 64,
        XV_HEIGHT, 64,
```

```
            NULL);
        for(i=0;i<count;i++)
        {
            printf("create_array: creating window %d . . . \n",
            (i+1));
            sprintf(title,"Slice View: %d", (i+1));
            printf("    creating frame % d . . . \n",
            (i+1));
            array->window[i] = xv_create(main_win->main_window,
            FRAME,
                XV_WIDTH, 200,
                XV_HEIGHT, 200,
                XV_LABEL, title,
                XV_SHOW, TRUE,
                FRAME_SHOW_FOOTER, TRUE,
                FRAME_SHOW_RESIZE_CORNER, TRUE,
                FRAME_ICON,
                    xv_create(XV_NULL, ICON,
                        ICON_IMAGE, window_image,
                        NULL),
                NULL);
            if(array->window[i] == NULL)
            {
                array->count = i;
                free_window_array( );
                return (0);
            }
            printf("    creating canvas %d . . . \n",
            (i+1));
            array->canvas[i] = xv_create(array->window[i], CANVAS,
                XV_X, 0,
                XV_Y, 0,
                XV_WIDTH, WIN_EXTEND_TO_EDGE,
                XV_HEIGHT, WIN_EXTEND_TO_EDGE,
                NULL);
            printf("    creating scrollbars %d . . . \n",
            (i+1));
            xv_creat(array->canvas[i],
                SCROLLBAR, SCROLLBAR_DIRECTION,
                SCROLLBAR_HORIZONTAL, NULL);
            xv_create(array->canvas[i],
                SCROLLBAR, SCROLLBAR_DIRECTION,
                SCROLLBAR_VERTICAL, NULL);
            xv_set(array->canvas[i],
            CANVAS_MIN_PAINT_WIDTH, 300,
            NULL);
            xv_set(array->canvas[i],
            CANVAS_MIN_PAINT_HEIGHT, 300,
            NULL);
            xv_set(array->canvas[i],
            CANVAS_WIDTH, 500,
            CANVAS_HEIGHT, 500, NULL);
            xv_set(array->canvas[i],
            CANVAS_AUTO_EXPAND, TRUE,
            NULL);
            printf("    creating paint_window %d
            . . . \n", (i+1));
            paint_xv_window =
            (Xv_Window)xv_get(array->canvas[i],
            CANVAS_NTH_PAINT_WINDOW, 0);
            array->paint_window[i] = (Window)
            xv_get(pint_xv_window,XV_XID);
            XSetWindowBackground(display,
            array->paint_window[i],
            black_pixel);
            notify_interpose_destroy_func(array->window[i],
            array_window_destroy);
        }
        return (1);
}
/*
 * sub window's window destruction notifier
 */
Notify_value array_window_destroy(client, status)
Notify_client client;
Destroy_status status;
{
    if(status == DESTROY_CHECKING)
    {
```

```
            if(get_destroy_override( ) == 0)
                notify_veto_destroy(client);
    }
    else if (status == DESTROY_CLEANUP)
        return notify_next_destroy_func(client, status);
    return NOTIFY_DONE;
}
/*
 * display_array:
 *
 * display status displays a set of slices from a given image in the
window array
 *
 */
void display_array(int count, int *index, unsigned char *img,
SKELETON *skeleton_start)
{
        g3dplan_main_window_objects    *main_win =
        get_main_window_objects( );
        g3dplan_window_array_objects   *array =
        get_window,array_pointer( );
        char *prog_name = get_prog_name( );
        Visual *visual = get_visual( );
        Displayl *display = get_display( );
        int    (img_width = get_img_width( ),
                img_height = get_img_height( ),
                img_depth = get_img_depth( );  /* range of the image
                */
        int    load_mag = get_load_mag( );
        GC     gc = get_gc( );
        unsigned   long black_pixel = get_black_pixel( ),
                   white_pixel = get_white_pixel( ),
                   red_pixel = get_red_pixel( ),
                   yellow_pixel = get_yellow_pixel( ),
                   blue_pixel = get_blue_pixel( ),
                   brown_pixel = get_brown_pixel( ),
                   orange_pixel = get_orange_pixel( ),
                   green_pixel = get_green_pixel( ),
        CONTOUR C;
        int i, j, slice, img_count, offset=0;
        int x1, y1, x2, y2, rm, found;
        double dz, rad;
        int row, col;
        int    disp_mag;
        int  timg_size, timg_width, timg_height;
        char title(64);
        unsigned char   *timg=NULL;
        XImage   *ximage = NULL;
        SKELETON *node = NULL;
        float wt = -1.0;
        /* now the display part :-1 */
        if(array->count < 1 || index == NULL || img == NULL ||
        count < 1)
                return;
        for(i=0;i<count;i++)
        {
                if(index[i] < 0 || index[i] >= img_depth)
                        return;
        }
        XSetBackground(display, gc, black_pixel);
        XSetForeground(display, gc, white_pixel);
        for(i=0;i<array->count,i++)
                XSetWindowBackground(display,
                array->paint_window[i],
                black_pixel);
        /* magnified image dimensions */
        disp_mag = (int) xv_get(main_win->display_mag,
        PANEL_VALUE);
        timg_width = img_width * disp_mag;
        timg_height = img_height * disp_mag ;
        timg_size * timg_width * timg_height;
        /* allocate memory for imgs */
        timg = (unsigned char *) calloc (timg_size, sizeof(char));
        if(!timg)
        {
                xv_set(main_win->main_window,
                FRAME_LEFT_FOOTER,
                    "display_array; ERROR -> memory allocation
                    failed", NULL);
```

```
        XBell(display, 0);
        return;
}
ximage = XCreateImage(display, visual, 8, ZPixmap, 0, NULL,
            (unsigned int)(timg_width), (unsigned
            int)(timg_height), 8, 0);
if(ximage == NULL)
{
        GFree(timg);
        xv_set(main_win->main_window,
        FRAME_LEFT_FOOTER,
            "display_array: ERROR -> memory allocation
            failed", NULL);
        XBell(display, 0);
        return;
}
/* magnify the image and display */
if(array->count < count)
        img_count = array->count;
else
        img_count = count;
for(slice=0;slice<img_count;slice++)
{
        offset = index[slice]*img_width*img_height;
        (void) mag2D((img+offset), img_width, img_height,
        timg, disp_mag, disp_mag);
        i = 0;
        for(row = 0;row < (timg_height); row++)
        {
            for(col = 0;col < (timg_width); col++)
            {
                if(int) timg[i] > 0)
                    timg[i] = white_pixel;
                else
                    timg[i] = black_pixel;
                i ++;
            }
        }
        sprintf(title, "Slice: %d", index[slice]);
        xv_set(array->window[slice], XV_LABEL, title,
        NULL);
        xv_set(array->window[slice], XV_SHOW, TRUE,
        NULL);
        XClearWindow(display, array->paint_window[slice]);
        XSetWindowBackground(display,
        array->paint_window[slice], black_pixel);
        XSetForeground(display, gc, white_pixel);
        ximage->data = (char *)timg;
        ximage->byte_order = MSBFirst;
        ximage->bitmap_bit_order = MSBFirst;
        XPutImage(display, array->paint_window[slice], gc,
        ximage, 0, 0, MARGIN, MARGIN,
            (unsigned int)(timg_width), (unsigned
            int) (timg_height));
        XSetForeground(display, gc, red_pixel);
        x1 = MARGIN-1;
        y1 = MARGIN-1;
        x2 = timg_width + 1;
        y2 = timg_height + 1;
        XDrawRectangle(display, array->paint_window[slice],
        gc, x1, y1, x2, y2);
        /*
         * now for skeletons
         */
        if(skeketon_start != NULL)
        {
          XSetBackground(display, gc, black_pixel);
          XSetWindowBackground(display,
          array->paint_window[slice], black_pixel);
          node = skeketon_start;
          while( node != NULL)
          {
            if(node->position.z >= (index[slice]-0.5) &&
            node->position.z <= (index[slice]+0.5))
            {
                rm = (floor((double)(disp_mag *
                (node->thickness +0.5))));
                x2 = MARGIN +
                (floor((double)(disp_mag*(node->position.x
```

```
                + 0.5))));
            y2 = MARGIN +
                (floor((double)(disp_mag*(node->position.y
                + 0.5))));
            x1 = x2 - rm;
            y1 = y2 - rm;
            XSetForeground(display, gc,
            blue_pixel);
            XDrawArc(display,
            array->paint_window[slice], gc, x1, y1,
            (2*rm), (2*rm), 0, (64*360));
            XSetForeground(display, gc, red_pixel);
            XDrawLine(display,
            array->paint_window[slice], gc, x2-5,
            y2, x2+5, y2);
            XDrawLine(display,
            array->paint_window[slice], gc, x2,
            y2-5, x2, y2+5);
        }
        else if ( ( (float)index[slice] >
        (node->position.z - node->thickness) ) && (
        (float)index[slice] <
                (node->position.z +
                node->thickness) ) )
        {
            /*
            dz = fabs((double)((float)index[slice]
            - node->position.z));
            dz = (node->thickness * node->thickness
            - dz*dz);
            if(dz < 0)
                rad = 0.0;
            else
                rad = disp_mag*sqrt(dz);
            rm = rad;
            x2 = MARGIN +
            (floor((double)(disp_mag*(node->position.x
            + 0.5))));
            y2 = MARGIN +
            (floor((double)(disp_mag*(node->position.y
            + 0.5))));
            x1 = x2 - rm;
            y1 = y2 - rm;
            */
            wt = get_weighting(node->helmet,
            node->thickness/load_mag);
            rm = get_drawr(node->position.z,
            index[slice],
            node->helmet)*wt*load)mag*disp_mag;
            if(rm < 0.0) rm = 0.0;
            x2 = MARGIN +
            (floor((double)(disp_mag*(node->position.x
            + 0.5))));
            y2 = MARGIN +
            (floor((double)(disp_mag*(node->position.y
            + 0.5))));
            x1 = x2 - rm;
            y1 = y2 - rm;
            XSetForeground(display, gc,
            yellow_pixel);
            XDrawArc(display,
            array->paint_window[slice], gc, x1, y1,
            (2*rm), (2*rm), 0, (64*360));
        }
        node = node->next;
    }
    XSetForeground(display, gc, white_pixel);
}
/*
 * contours
 */
XSetBackground(display, gc, black_pixel);
XSetForeground(display, gc, green_pixel);
XSetWindowBackground(display,
array->paint_window[slice], black_pixel);
c = get_contour( );
j = 0;
found = 0;
while(j < c.num_slices )
```

-continued

```
                {
                        dz = (c.z[j] - c.min_z);
                        if((float)index[slice] >= (float)(dz-0.5) &&
                (float)index[slice] < (float)(dz+0.5))
                        {
                                found = 1;
                                break;
                        }
                        j ++;
                }
                if ( found )
                {
                        for(i=0, i < c.num_vert[j]-1; i++)
                        {
                                x1 = MARGIN + (floor(double)disp_mag *
                                (0.5 + c.x[j][i] - c.min_x)));
                                y1 = MARGIN + (floor((double)disp_mag *
                                (0.5 + c.y[j][i] - c.min_y)));
                                x2 = MARGIN + (floor((double)disp_mag *
                                (0.5 + c.x[j][i+1] - c.min_x)));
                                y2 = MARGIN + (floor(double)disp_mag *
                                (0.5 + c.y[j][i+1] - c.min_y)));
                                XDrawLine(display,
                                array->paint_window[slice], gc, x1, y1,
                                x2, y2);
                        }
                        x1 = MARGIN + (floor((double)disp_mag * (0.5 +
                        c.x[j](c.num_vert[j]-1] - c.min_x)));
                        y1 = MARGIN + (floor((double)disp_mag * (0.5 +
                        c.y[j](c.num_vert[i]-1] - c.min_y)));
                        x2 = MARGIN + (floor((double)disp_mag * (0.5 +
                        c.x[j][0] - c.min_x)));
                        y2 = MARGIN + (floor((double)disp_mag * (0.5 +
                        c.y[j][0] - c.min_y)));
                        XDrawLine(display, array->paint_window[slice],
                        gc, x1, y1, y2);
                }
        }
        XSetForeground(display, gc, white_pixel);
        ximage->data = NULL;
        XDestroyImage(ximage);
        ximage = NULL;
        GFree(timg);
        timg = NULL;
        XFlush(display);
        return;
}
/*
* processing routines for g3dplan:
* display_3d.c
*
*/
#include "includes.h"
#include "g3dplan_ui.h"
#include "g3dplan.h"
extern g3dplan_sub_window_objects   *get_sub_window_objects( );
extern g3dplan_main_window_objects *get_main_window_objects( );
extern char *get_prog_name( );
extern int get_img_width( ), get_img_height( ), get_img_depth( ); /*
range of the image */
extern int mag3D( );
extern int mag2D( );
extern void GFree( );
extern int get_current_slice( );
extern void set_current_slice(int);
/* X display variables */
extern Visual *get_visual( );
extern Display *get_display( );
extern Colormap get_colormap( );
extern Window   get_paint_window( ), get_sub_paint_window( );
extern GC   get_sub_gc( );
extern unsigned long get_black_pixel( ), get_white_pixel( ),
get_red_pixel( ),
                        get_yellow_pixel( ), get_green_pixel( );
extern int      get_load_mag( );
extern int      get_img_min( ), get_img_max( );
extern int      get_img_width( ), get_img_height( ), get_img_depth( );
extern float    get_view_vmin( ), get_view_vmax( ), get_view_umin( ),
get_view_umax( );
```

-continued

```
extern void    get_view(float *, float *, float, float, float);
/*
 * display_box;
 *
 */
void display_box( )
{
        g3dplan_main_window_objects    *main_win =
        get_main_window_objects( );
        g3dplan_sub_window_objects     *sub_win =
        get_sub_window_objects( );
        char *prog_name = get_prog_name( );
        Visual *visual = get_visual( );
        Display *display = get_display( );
        Colormap cmap = get_colormap( );
        Window   sub_paint_window = get_sub_paint_window( );
        GC   sub_gc = get_sub_gc( );
        unsigned   long black_pixel = get_black_pixel( ),
                   white_pixel = get_white_pixel( ),
                   red_pixel = get_red_pixel( ),
                   yellow_pixel = get_yellow_pixel( ),
                   green_pixel = get_green_pixel( );
        int    w = get_img_width( ),
               h = get_img_height( ),
               d = get_img_depth( );
        int    disp_mag;
        int xi, yi, zi;
        float v, u;
        int x1,y1, x2, y2, x3, y3, x5, y4, x5, y5, x6, y6, x7, y7, x8,
        y8;
        float offset;
        float    vmin = get_view_vmin( ),
                 vmax = get_view_vmax( ),
                 umin = get_view_umin( ),
                 umax = get_view_umax( ),
        xv_set(sub_sin->sub_window, FRAME_LEFT_FOOTER,
        "display_3d:
        display box . . . ", NULL);
        disp_mag = (int) xv_get(main_win->display_mag,
        PANEL_VALUE);
        XSetForeground(display, sub_gc, red_pixel);
        /* point 1*/
        xi = 0 ;
        yi = 0 ;
        zi = 0 ;
        get_view(&v,&u,xi,yi,zi);
        x1 = MARGIN + (floor((double)(disp_mag*(v-vmin + 0.5))));
        y1 = MARGIN + (floor((double)(disp_mag*(u-umin + 0.5))));
        /* point 2*/
        xi = 0 ;
        yi = 0 ;
        zi = d-1 ;
        get_view(&v,&u,xi,yi,zi);
        x2 = MARGIN + (floor((double)(disp_mag*(v-vmin + 0.5))));
        y2 = MARGIN + (floor((double)(disp_mag*(u-umin + 0.5))));
        /* point 3*/
        xi = 0 ;
        yi = h-1 ;
        zi = 0 ;
        get_view(&v,&u,xi,yi,zi);
        x3 = MARGIN + (floor((double)(disp_mag*(v-vmin + 0.5))));
        y3 = MARGIN + (floor((double)(disp_mag*(u-umin + 0.5))));
        /* point 4*/
        xi = 0 ;
        yi = h-1 ;
        zi = d-1 ;
        get_view(&v,&u,xi,yi,zi);
        x4 = MARGIN + (floor((double)(disp_mag*(v-vmin + 0.5))));
        y4 = MARGIN + (floor((double)(disp_mag*(u-umin + 0.5))));
        /* point 5*/
        xi = w-1 ;
        yi = 0 ;
        zi = 0 ;
        get_view(&v,&u,xi,yi,zi);
        x5 = MARGIN + (floor((double)(disp_mag*(v-vmin + 0.5))));
        y5 = MARGIN + (floor((double)(disp_mag*(u-umin + 0.5))));
        /* point 6*/
        xi = w-1 ;
        yi = 0 ;
```

-continued

```
        zi = d−1 ;
        get_view(&v,&u,xi,yi,zi);
        x6 = MARGIN + (floor((double)(disp_mag*(v−vmin + 0.5))));
        y6 = MARGIN + (floor((double)(disp_mag*(u−umin + 0.5))));
        /* point 7*/
        xi = w−1 ;
        yi = h−1 ;
        zi = 0 ;
        get_view(&v,&u,xi,yi,zi);
        x7 = MARGIN + (floor((double)(disp_mag*(v−vmin + 0.5))));
        y7 = MARGIN + (floor((double)(disp_mag*(u−umin + 0.5))));
        /* point 8*/
        xi = w−1 ;
        yi = h−1 ;
        zi = d−1 ;
        get_view(&v,&u,xi,yi,zi);
        x8 = MARGIN + (floor((double)(disp_mag*(v−vmin + 0.5))));
        y8 = MARGIN + (floor((double)(disp_mag*(u−umin + 0.5))));
        XDrawLine(display, sub_paint_window, sub_gc, x1, y1, x2, y2);
        XDrawLine(display, sub_paint_window, sub_gc, x1, y1, x3, y3);
        XDrawLine(display, sub_paint_window, sub_gc, x1, y1, x5, y5);
        XDrawLine(display, sub_paint_window, sub_gc, x5, y5, x6, y6);
        XDrawLine(display, sub_paint_window, sub_gc, x5, y5, x7, y7);
        XDrawLine(display, sub_paint_window, sub_gc, x3, y3, x7, y7);
        XDrawLine(display, sub_paint_window, sub_gc, x3, y3, x4, y4);
        XDrawLine(display, sub_paint_window, sub_gc, x8, y8, x4, y4);
        XDrawLine(display, sub_paint_window, sub_gc, x8, y8, x7, y7);
        XDrawLine(display, sub_paint_window, sub_gc, x8, y8, x6, y6);
        XDrawLine(display, sub_paint_window, sub_gc, x2, y2, x6, y6);
        XDrawLine(display, sub_paint_window, sub_gc, x2, y2, x5, y4);
        XSetForeground(display, sub_gc, white_pixel);
        return;
}
/*
 * processing routines for g3dplan:
 * display_status.c
 *
 */
#include "includes.h"
#include "g3dplan_ui.h"
#include "g3dplan.h"
extern g3dplan_main_window_objects *get_main_window_objects( );
extern char *get_prog_name( );
extern CONTOUR get_contour( );
extern int   get_img_width( ), get_img_height( ), get_img_depth( );
/* range of the image */
extern int mag3D( );
extern int mag2D( );
extern void GFree( );
extern int get_current_slice( );
extern void set_current_slice(int);
/* X display variables */
extern Visual *get_visual( );
extern Display *get_display( );
extern Colormap get_colormap( );
extern Window  get_paint_window( ), get_sub_paint_window( );
extern GC   get_gc( ), get_sub_gc( );
extern unsigned long get_black_pixel( ), get_white_pixel( ),
get_red_pixel( ),
                 get_yellow_pixel( ), get_green_pixel( ),
                 get_blue_pixel( ), get_brown_pixel( ),
                 get_orange_pixel( ),
                 get_gray_start_pixel( );
extern int   set_canvas_width( ), set_canvas_height( ),
             set_sub_canvas_height( ), set_sub_canvas_width( );
extern int   get_depth( );
extern int   get_load_mag( );
extern int   get_img_min( ), get_img_max( );
/*
 * display_status:
 *
 * display status displays image/skeleton/all depending on the
arguments
 *
 * the first argument in the variable list is the display type :
 *
 *    DISPLAY_SKELETON, then there just one more argument which is
address of skeleton, if
 *    DISPLAY_IMAGE, then next argument is the address of the image
```

```
 *      DISPLAY_GRAY will be image pointer to grayscale image
 *      DISPLAY_ALL has one more additional argument, the address of
skeleton data.
 *
 */
void display_status(int display_type, . . . )
{
    va_list arg;
    g3dplan_main_window_objects   *main_win =
    get_main_window_objects( );
    char *prog_name = get_prog_name( );
    Visual *visual = get_visual( );
    Display *display = get_display( );
    CONTOUR contour = get_contour( );
    int     img_width = get_img_width( ),
            img_height = get_img_height( ),
            img_depth = get_img_depth( );  /*range of the image
            */
    int     load_mag = get_load_mag( );
    Colormap cmap = get_colormap( );
    Window   paint_window = get_paint_window( ),
    sub_paint_window =
    get_sub_paint_window( );
    GC      gc = get_gc( ), sub_gc = get_sub_gc( );
    unsigned         long black_pixel = get_black_pixel( ),
                     white_pixel = get_white_pixel( ),
                     red_pixel = get_red_pixel( ),
                     yellow_pixel = get_yellow_pixel( ),
                     blue_pixel = get_blue_pixel( ),
                     brown_pixel = get_brown_pixel( ),
                     orange_pixel = get_orange_pixel( ),
                     green_pixel = get_green_pixel( );
    int     canvas_width = get_canvas_width( ),
            canvas_height = get_canvas_height( ),
            sub_canvas_height = get_sub_canvas_height( ),
            sub_canvas_width = get_sub_canvas_width( );
    int     depth = get_depth( );
    unsigned long gray_start_pixel = get_gray_start_pixel( );
    int     slice = get_current_slice( );
    int i, j, offset=0, min= get_img_min( ), max= get_img_max( );
    int x1, y1, x2, y2, rm, found,
    double dz, rad;
    int row,col,index;
    int     disp_mag;
    CONTOUR C;
    unsigned char *image = NULL;
    unsigned char   *timg=NULL;
    int timg_size, timg_width, timg_height;
    SKELETON *node = NULL;
    SKELETON *skeleton_start = NULL;
    XImage *ximage = NULL;
    /* get the arguments */
    if(display_type == DISPLAY_SKELETON)
    {
        va_start(arg, display_type);
        skeketon_start = va_arg(arg, SKELETON *);
        if(skeketon_start == NULL)
        {
            xv_set(main_win->main_window,
            FRAME_LEFT_FOOTER,
                "display_status: ERROR -> NULL Skeleton
                passed", NULL);
            XBell(display, 0);
            return;
        }
    }
    else if(display_type == DISPLAY_GRAY)
    {
        va_start(arg, display_type);
        image = (unsigned char *)va_arg(arg, char *);
        if(image == NULL)
        {
            xv_set(main_win->main_window,
            FRAME_LEFT_FOOTER,
                    "display_status: ERROR -> NULL
                    image passed", NULL);
            XBell(display, 0);
            return;
        }
```

```
}
else if(display_type == DISPLAY_IMAGE || display_type ==
DISPLAY_ALL )
{
    va_start(arg, display_type);
    image = (unsigned char *)va_arg(arg, unsigned char *);
    if(image == NULL)
    {
        xv_set(main_win->main_window,
        FRAME_LEFT_FOOTER,
            "display_status: ERROR -> NULL image
            passed", NULL);
        XBell(display, 0);
        return;
    }
    if(display_type == DISPLAY_ALL)
    {
        skeketon_start = va_arg(arg, SKELETON *);
        if(skeketon_start == NULL)
        {
            va_end(arg);
            xv_set(main_win->main_window,
            FRAME_LEFT_FOOTER,
                    "display_status: ERROR
                    -> NULL skeleton
                    passed", NULL);
            XBell(display, 0);
            return;
        }
    }
}
else if(display_type == DISPLAY_NONE)
{
}
else
{
    xv_set(main_win->main_window,
    FRAME_LEFT_FOOTER,
        "display_status: ERROR -> Unknown type (check
        Program)", NULL);
    XBell(display, 0);
    return;
}
/*
 * get the slice number
 */
if(slice < 0 || slice >= img_depth)
{
    xv_set(main_win->main_window,
    FRAME_LEFT_FOOTER,
            "display_status: ERROR -> slice number
            incorect(Check Program)", NULL);
    XBell(display, 0);
}
/* now the display part :-1 */
xv_set(main_win->main_window,
FRAME_LEFT_FOOTER,"display_status: display . . . ", NULL);
XClearWindow(display, paint_window);
disp_mag = (int) xv_get(main_win->display_mag,
PANEL_VALUE);
canvas_width = (contour.max_x - contour.min_x) * disp_mag +
2 * MARGIN + 10;
canvas_height = (contour.max_y - contour.min_y) * disp_mag + 2
* MARGIN + 10;
xv_set(main_win->main_canvas, CANVAS_WIDTH,
canvas_width,
CANVAS_HEIGHT, canvas_height, NULL);
set_canvas_width(canvas_width);
set_canvas_height(canvas_height);
XFlush(display);
/* image */
if ((display_type == DISPLAY_IMAGE) || (display_type ==
DISPLAY_ALL))
{
    XSetBackground(display, gc, black_pixel);
    XSetForeground(display, gc, white_pixel);
    XClearWindow(display, paint_window);
    XSetWindowBackground(display, paint_window,
    black_pixel);
```

```
/* magnified image dimensions */
disp_mag = (int) xv_get(main_win->disp_mag,
PANEL_VALUE);
timg_width = img_width * disp_mag;
timg_height = img_height * disp_mag;
timg_size = timg_width * timg_height;
/* allocate memory for imgs */
timg * (unsigned char *) calloc (timg_size,
sizeof(char));
if(!timg)
{
    xv_set(main_win->main_window,
    FRAME_LEFT_FOOTER,
        "display_status: ERROR -> memory
        allocation failed", NULL);
    XBell(display, 0);
    return;
}
/* allocat memory for imgs */
/* manifiy the image */
offset = slice*img_width*img_height;
(void) mag2D(image+offset), img_width, img_height,
timg, disp_mag, disp_mag);
index = 0;
for(row = 0;row < (timg_height); row++)
{
    for(col = 0;col < (timg_width); col++)
    {
        if((int) timg[index] > 0)
            timg[index] = green_pixel;
        else
            timg[index] black_pixel;
        index ++;
    }
}
ximage = XCreateImage(display, visual, 8, ZPixmap, 0,
NULL,
        (unsigned int)(timg_width), (unsigned
        int)(timg_height), 8, 0);
if(ximage != NULL)
{
    ximage->data = (char *)timg;
    ximage->byte_order = MSBFirst;
    ximage->bitmap_bit_order = MSBFirst;
    XPutImage(display, paint_window, gc, ximage, 0,
    0, MARGIN, MARGIN,
            (unsigned int)(timg_width),
            (unsigned int)(timg_height));
    ximage->data = NULL;
    XDestroyImage(ximage);
}
ximage = NULL;
GFree(timg);
timg = NULL;
}
if ((display_type == DISPLAY_SKELETON) || (display_type ==
DISPLAY_ALL))
{
  if(skeketon_start != NULL)
  {
  XSetBackground(display, gc, black_pixel);
  XSetWindowBackground(display, paint_window,
  black_pixel);
  node = skeketon_start;
  while( node != NULL)
  {
        if(node->position.z >= (slice-0.5) &&
        node->position.z <= (slice+0.5))
        {
            rm = (floor((double)(disp_mag *
            (node->thickness +0.5))));
            x2 = MARGIN +
            (floor((double)(disp_mag*(node->position.x
            + 0.5))));
            y2 = MARGIN +
            (floor((double)(disp_mag*(node->position.y
            + 0.5))));
            x1 = x2 - rm;
            y1 = y2 - rm;
```

```
            XSetForeground(display, gc,
            blue_pixel);
            XDrawArc(display, paint_window, gc, x1,
            y1, (2*rm), (2*rm), 0, (64*360));
            XSetForeground(display, gc,
            orange_pixel);
            /*
            XDrawPoint(display, paint_window, gc,
            x2, y2);
            */
            XDrawLine(display, paint_window, gc,
            x2-5, y2, x2+5, y2);
            XDrawLine(display, paint_window, gc,
            x2, y2-5, x2, y2+5);
        }
        else if ( ( (float)slice > (node->position.z -
        node->thickness) ) && ( (float)slice <
                (node->position.z +
                node->thickness) ) )
        {
            dz = fabs((double)((float)slice -
            node->position.z));
            dz= (node->thickness * node->thickness
            - dz*dz);
            if(dz < 0)
                rad = 0.0;
            else
                rad = disp_mag*sqrt(dz);
            rm = rad;
            x2 = MARGIN +
            (floor((double)(disp_mag*(node->position.x
            + 0.5))));
            y2 = MARGIN +
            (floor((double)(disp_mag*(node->position.y
            + 0.5))));
            x1 = x2 - rm;
            y1 = y2 - rm;
            XSetForeground(display, gc,
            brown_pixel);
            XDrawArc(display, paint_window, gc, x1,
            y1, (2*rm), (2*rm), 0, (64*360));
        }
        node = node->next;
    }
    XSetForeground(display, gc, white_pixel);
  }
}
if(display_type == DISPLAY_GRAY)
{
    XSetBackground(display, gc, black_pixel);
    XSetForeground(display, gc, white_pixel);
    XClearWindow(display, paint_window);
    XSetWindowBackground(display1, paint_window,
    black_pixel);
    /* magnified image dimensions */
    disp_mag = (int) xv_get(main_win->display_mag,
    PANEL_VALUE);
    timg_width = img_width * disp_mag;
    timg_height = img_height * disp_mag ;
    timg_size = timg_width * timg_height;
    /* allocat memory for imgs */
    timg = (unsigned char *) calloc (timg_size,
    sizeof(char));
    if(!timg)
    {
        xv_set(main_win->main_window,
        FRAME_LEFT_FOOTER,
            "display_status: ERROR -> memory
            allocation failed", NULL);
        XBell(display, 0);
        return;
    }
    /* manifiy the image */
    offset = slice*img_width*img_height;
    (void) mag2D(image+offset), img_width, img_height,
    timg, disp_mag, disp_mag);
    index = 0;
    for(i=0;i<timg_height;i++)
    {
```

```
            for(j=0;j<timg_width;j++)
            {
                if(max == min)
                    timg[index] = gray_start_pixel;
                else
                    timg[index] = gray_start_pixel
                        +
                            (GRAY_COLORS-1)+
                            ((int)timg[index]-min)/(min-min
                index++)
            }
        }
        XSetBackground(display, gc, black_pixel);
        XSetForeground(display, gc, white_pixel);
        XSetWindowBackground(display, paint_window,
        black_pixel);
        ximage = XCreateImage(display, visual, 8, ZPixmap, 0,
        NULL,
                (unsigned int)(timg_width), (unsigned
                int)(timg_height), 8, 0);
        if(ximage != NULL)
        {
            ximage->data = (char *)timg;
            ximage->byte_order = MSBFirst;
            ximage->bitmap_bit_order = MSBFirst;
            XPutImage(display, paint_window, gc, ximage, 0,
            0, MARGIN, MARGIN,
                    (unsigned int)(timg_width),
                    (unsigned int)(timg_height));
            ximage->data = NULL;
            XDestroyImage(ximage);
        }
        ximage = NULL;
        GFree(timg);
        timg = NULL;
    }
    /* border */
    XSetBackground(display, gc, black_pixel);
    XSetForeground(display, gc, green_pixel);
    XSetWindowBackground(display, paint_window, black_pixel);
    x1 = MARGIN;
    y1 = MARGIN;
    x2 = (contour.max_x - contour.min_x) * disp_mag;
    y2 = (contour.max_y - contour.min_y) * disp_mag;
    XDrawRectangle(display, paint_window, gc, x1, y1, x2, y2);
    /* contour */
    XSetBackground(display, gc, black_pixel);
    XSetForeground(display, gc, red_pixel);
    XSetWindowBackground(display1, paint_window, black_pixel);
    c = get_contour( );
    j = 0;
    found = 0;
    while(j < c.num_slices )
    {
        dz = (c.z[j] - c.min_z);
        if(float)slice >= (float)(dz-0.5) && (float)slice <
        (float)(dz+0.5))
        {
            found = 1;
            break;
        }
        j ++;
    }
    if ( found )
    {
        for(i=0; i < c.num_vert[j]-1; i++)
        {
            x1 = MARGIN + disp_mag * (0.5 +
            floor(double)((c.x[j][i] - c.min_x)+0.5)));
            y1 = MARGIN + disp_mag * (0.5 +
            floor(double)((c.y[j][i] - c.min_y)+0.5)));
            x2 = MARGIN + disp_mag * (0.5 +
            floor((double)((c.x[j][i+1] - c.min)x)+0.5)));
            y2 = MARGIN + disp_mag * (0.5 +
            floor((double)((c.y[j][i+1] - c.min_y)+0.5)));
            XDrawLine(display, paint_window, gc, x1, y1,
            x2, y2);
        }
        x1 = MARGIN + disp_mag * (0.5 +
```

```
            floor((double)((c.x[j](c.num_vert[j]-1) -
            c.min_x)+0.5)));
        y1 = MARGIN + disp_mag * (0.5 +
            floor((double)((c.y[j](c.num_vert[j]-1) -
            c.min_y)+0.5)));
        x2 = MARGIN + disp_mag * (0.5 +
            floor((double)((c.x[j][0] - c.min_x)+0.5)));
        y2 = MARGIN + disp_mag * (0.5 +
            floor((double)((c.y[j][0] - c.min_y)+0.5)));
        XDrawLine(display, paint_window, gc, x1, y1, x2, y2);
    }
    XFlush(display);
    return;
}
/*
 * processing routines for g3dplan:
 * display_update.c
 *
 * button callback routines
 *
 */
#include "includes.h"
#include "g3dplan_ui.h"
#include "g3dplan.h"
extern void display_status( );
SKELETON *get_first_skelet( );
void
display_update( )
{
    SKELETON *first_skelet = get_first_skelet( );
    if((first_skelet !=NULL)
        display_status(DISPLAY_SKELETON,first_skelet);
    /*
    else if(line !=NULL)
        display_status(DISPLAY_NONE);
    */
    return;
}
#include <math.h>
#include "includes.h"
#include "g3dplan_ui.h"
#include "g3dplan.h"
extern int get_stage( ), get_img_width( ), get_img_height( ),
    get_img_depth( );
extern int mag3D( );
extern int mag2D( );
extern void GFree( );
extern SKELETON *add_node( );
extern int ridge( ), sedt( );
extern int ridge2sk( );
/*
 * Routine Name: edtsk   get skeleton of an image.
 *
 */
int edtsk3d(img1, end1, cross,sk)
unsigned char *img1;
SKELETON **end1, **cross, **sk;
{
    int   img_width = get_img_width( ),
          img_height = get_img_height( ),
          img_depth = get_img_depth( ),
          stage = get_stage( ),
          load_mag = get_load_mag( );
    int i, j, k, r, index,ind;
    int min, max;
    int row, col, dep;
    int endpoint( ), endpoint1( ), crosspt( );
    void fillgap( ), get_feature( );
    float  x,y,z radius;
    int    cutoff, c,en,cr;
    short  *s= NULL, *simg = NULL;
    if(!img1)
        return (0);
    simg = (short *) calloc(img_height*img_width*img_depth,
    sizeof(short));
    if(simg == NULL)
    {
        fprintf(stderr,"calloc( ) failed\n");
        return(0);
```

```c
        }
    if( !sedt(img1, simg))
    {
        GFree(simg);
        fprintf(stderr,"sedt( ) failed\n");
        return(0);
    }
    if(stage == 2)
        cutoff = (int)(load_mag*RMIN*RMIN*load_mag);
    else
        cutoff = (int)(load)mag*R8[0]*R8[0]*load_mag);
    c = (int)sqrt((double)cutoff);
    if( !ridge(simg,img_width, img_height, img_depth, img1))
    {
        GFree(simg);
        fprintf(stderr, "ridge( ) failed\n");
        return(0);
    }
    /* display_status(DISPLAY_GRAY,img1);*/
    /*
    if( !ridge2sk(img1, img_width, img_height, img_depth))
    {
        fprintf(stderr,"ridge2sk( ) failed\n");
        return(0);
    }
    */
/* get the skeleton points done: endpoint, crosspoint, skeleton point
etc */
    s = simg;
    for(dep=(c-1);dep<(img_depth-c+1);dep++)
    {
        for(row=(c-1);row<(img_height-c+1);row++)
        {
            for(col=(c-1); col<(img_width-c+1); col++)
            {
                ind = (dep*img_height +row)*img_width + col;
                radius = sqrt(s(ind));
                if(img1(ind) == 10 && radius <=
                (RMAX*load_mag))
                {
                    x = (float)col: y= (float)row;
                    z=(float)dep;
                    *sk = add_node(x,y,z,radius, 0,
                    (SKELETON*)(*sk));
                    get_feature(img1,img_width, img_height,
                    img_depth, col,row, dep, &en, &cr);
                    if(en)
                    {
                        *end1 = add_node(x,y,z,radius,
                        0, (SKELETON*)(*end1));
                        /* fprintf(stderr,"edtsk3d;
                        end; (%f %f %f %f)\n", x, y,
                        z, radius);*/
                    }
                    if(cr)
                    {
                        *cross = add_nod(x,y,z,radius,
                        0, (SKELETON*)(*cross));
        /*              fprintf(stderr,"edtsk3d;
    cross: (%f %f %f %f)\n", x, y, z, radius);*/
                    }
                }
            }
        }
    }
    GFree(simg);
    if(*sk == NULL)
    {
    fprintf(stderr,"edtsk3d( ): NULL SK!\n");
    return(0);
}
fprintf(stderr,"edtsk3d( ): done \n");
    return(1),
}
void get_feature(image, ncol, nrow,ndep, cindex, rindex,dindex, end,
cross)
unsigned char *image;
int ncol, nrow, ndep, rindex, cindex, dindex;
int *end, *cross;
```

```c
{
    int kk, index, index1, index2;
    unsigned char bu[9], ho[9],b1[9], pb[9];
    int p1_found=FALSE, p2_found = FALSE;
    if(image == NULL ||
        ncol <= 1 || cindex >= (ncol-1) || cindex < 1 ||
        nrow <= 1 || rindex >= (nrow-1) || rindex < 1 ||
        * ndep <= 1 || dindex >= (ndep-1) || dindex < 1)
    {
        fprintf(stderr,"get_pbox( ): Error !!!!\n");
        return;
    }
    *end = FALSE;
    *cross = FALSE;
    index = (dindex*nrow +rindex)*ncol + cindex;
    kk = nrow*ncol;
    bo[0] = image[index];
    bu[0] = image[index+kk];
    if(bu[0] !=0)
        p1_found = TRUE;
    b1[0] = image[index-kk];
    if(b1[0] !=0)
    {
        if( !p1_found)
            p1_found = TRUE;
        else
            p2_found = TRUE;
    }
    bo[7] = image[index-1];
    if(bo[7] !=0)
    {
        if( !p1_found)
            p1_found = TRUE;
        else if(!p2_found = TRUE;
            p2_found = TRUE;
        else
        {
            *end = FALSE;
            *cross = TRUE;
            return;
        }
    }
    bu[7] = image[index-1+kk];
    if(bu[7] !=0)
    {
        if( !p1_found)
            p1_found = TRUE;
        else if(!p2_found)
            p2_found = TRUE;
        else
        {
            *end = FALSE;
            *cross = TRUE;
            return;
        }
    }
    b1[7] = image[index-1-kk];
    if(b1[7] !=0)
    {
        if( !p1_found)
            p1_found = TRUE;
        else if(!p2_found)
            p2_found = TRUE;
        else
        {
            *end = FALSE;
            *cross = TRUE;
            return;
        }
    }
    bo[3] = image[index+1];
    if(bo[3] !=0)
    {
        if( !p1_found)
            p1_found = TRUE;
        else if(!p2_found)
            p2_found = TRUE;
        else
        {
```

```
                *end = FALSE;
                *cross = TRUE;
                return;
            }
    }
}
bu[3] = image[index+1+kk];
if(bu[3] !=0)
{
    if( !p1_found)
        p1_found = TRUE;
    else if(!p2_found)
        p2_found = TRUE;
    else
    {
        *end = FALSE;
        *cross = TRUE;
        return;
    }
}
b1[3] = image[index+1−kk];
if(b1[3] !=0)
{
    if( !p1_found)
        p1_found = TRUE;
    else if(!p2_found)
        p2_found = TRUE;
    else
    {
        *end = FALSE;
        *cross = TRUE;
        return;
    }
}
index1 = index − ncol;
bo[1] = image[index1];
if(bo[1] !=0)
{
    if( !p1_found)
        p1_found = TRUE;
    else if(!p2_found)
        p2_found = TRUE;
    else
    {
        *end = FALSE;
        *cross = TRUE;
        return;
    }
}
bu[1] = image[index1+kk];
if(bu[1] !=0)
{
    if( !p1_found)
        p1_found = TRUE;
    else if(!p2_found)
        p2_found = TRUE;
    else
    {
        *end = FALSE;
        *cross = TRUE;
        return;
    }
}
b1[1] = image[index1−kk];
if(b1[1] !=0)
{
    if( !p1_found)
        p1_found = TRUE;
    else if(!p2_found)
        p2_found = TRUE;
    else
    {
        *end = FALSE;
        *cross = TRUE;
        return;
    }
}
bo[8] = image[index1−1];
if(bo[8] !=0)
{
```

-continued

```
            if( !p1_found)
                p1_found = TRUE;
            else if(!p2_found)
                p2_found = TRUE;
            else
            {
                *end = FALSE;
                *cross = TRUE;
                return;
            }
    }
    bu[8] = image[index1-1+kk];
    if(bu[8] !=0)
    {
            if( !p1_found)
                p1_found = TRUE;
            else if(!p2_found)
                p2_found = TRUE;
            else
            {
                *end = FALSE;
                *cross = TRUE;
                return;
            }
    }
    b1[8] = image[index1-1-kk];
    if(b1[8] !=0)
    {
            if( !p1_found)
                p1_found = TRUE;
            else if(!p2_found)
                p2_found = TRUE;
            else
            {
                *end = FALSE;
                *cross = TRUE;
                return;
            }
    }
    bo[2] = image[index+1];
    if(bo[2] !=0)
    {
            if( !p1_found)
                p1_found = TRUE;
            else if(!p2_found)
                p2_found = TRUE;
            else
            {
                *end = FALSE;
                *cross = TRUE;
                return;
            }
    }
    bu[2] = image[index+1+kk];
    if(bu[2] !=0)
    {
            if( !p1_found)
                p1_found = TRUE;
            else if(!p2_found)
                p2_found = TRUE;
            else
            {
                *end = FALSE;
                *cross = TRUE;
                return;
            }
    }
    b1[2] = image[index1+1-kk];
    if(b1[2] !=0)
    {
            if( !p1_found)
                p1_found = TRUE;
            else if(!p2_found)
                p2_found = TRUE;
            else
            {
                *end = FALSE;
                *cross = TRUE;
                return;
```

```
            }
        }
        index2 = index + ncol;
        bo[5] = image[index2];
        if(bo[5] !=0)
        {
            if( !p1_found)
                p1_found = TRUE;
            else if(!p2_found)
                p2_found = TRUE;
            else
            {
                *end = FALSE;
                *cross = TRUE;
                return;
            }
        }
        bu[5] = image[index2+kk];
        if(bu[5] !=0)
        {
            if( !p1_found)
                p1_found = TRUE;
            else if(!p2_found)
                p2_found = TRUE;
            else
            {
                *end = FALSE;
                *cross = TRUE;
                return;
            }
        }
        b1[5] = image[index2−kk];
        if(b1[5] !=0)
        {
            if( !p1_found)
                p1_found = TRUE;
            else if(!p2_found)
                p2_found = TRUE;
            else
            {
                *end = FALSE;
                *cross = TRUE;
                return;
            }
        }
        bo[6] = image[index2−1];
        if(bo[6] !=0)
        {
            if( !p1_found)
                p1_found = TRUE;
            else if(!p2_found)
                p2_found = TRUE;
            else
            {
                *end = FALSE;
                *cross = TRUE;
                return;
            }
        }
        bu[6] = image[index2−1+kk];
        if(bu[6] !=0)
        {
            if( !p1_found)
                p1_found = TRUE;
            else if(!p2_found)
                p2_found = TRUE;
                {
            else
                {
                *end = FALSE;
                *cross = TRUE;
                return;
            }
        }
        b1[6] = image[index2−1−kk];
        if(b1[6] !=0)
        {
            if( !p1_found)
                p1_found = TRUE;
```

```
            else if(!p2_found)
                p2_found = TRUE;
            else
            {
                *end = FALSE;
                *cross = TRUE;
                return;
            }
        }
        bo[4] = image[index2+1];
        if(bo[4] !=0)
        {
            if( !p1_found)
                p1_found = TRUE;
            else if(!p2_found)
                p2_found = TRUE;
            else
            {
                *end = FALSE;
                *cross = TRUE;
                return;
            }
        }
        bu[4] = image[index2+1+kk];
        if(bu[4] !=0)
        {
            if( !p1_found)
                p1_found = TRUE;
            else if(!p2_found)
                p2_found = TRUE;
            else
            {
                *end = FALSE;
                *cross = TRUE;
                return;
            }
        }
        bl[4] = image[index+1-kk];
        if(bl[4] !=0)
        {
            if( !p1_found)
                p1_found = TRUE;
            else if(!p2_found)
                p2_found = TRUE;
            else
            {
                *end = FALSE;
                *cross = TRUE;
                return;
            }
        }
        /* now check if endpoints */
        if( p1_found && !p2_found)
        {
            *end = TRUE;
            *cross = FALSE;
            return;
        }
        /* now check if cross points */
        if( p1_found && p2_found)
        {
            *end = FALSE;
            *cross = FALSE;
            return ;
        }
        return;
}
/*
 * processing routines for g3dplan:
 * fill_contour.c
 *
 * button callback routines
 *
 */
#include "includes.h"
#include "g3dplan_ui.h"
#include "g3dplan.h"
#include "string.h"
/*
```

-continued

```
 * external function definitions.
 */
extern void display_status( );
extern g3dplan_main_window_objects * get_main_window_objects( );
extern char *get_prog_name( );
extern Display *get_display( );
extern SKELETON *get_first_skelet( );
extern void    free_list( );
extern unsigned char   *get_img( );
extern int     get_img_width( ), get_img_height( ), get_img_depth( );
extern unsigned short  *get_dist_img( );
extern void set_contour(CONTOUR);
extern void set_img(unsigned char *);
extern void set_dist_img(unsigned short *);
extern void set_first_skelet(SKELETON *);
extern CONTOUR get_contour( );
extern void set_img_width(int);
extern void set_img_height(int);
extern void set_img_depth(int);
extern int get_load_mag( );
extern void print_1contour(CONTOUR);
extern void print_dimensions( );
extern int make_window_array(int);
extern ILIST *atoil(char *);
extern void FreeIlist(ILIST *);
extern void dil( );
void
fill_contour( )
{
    g3dplan_main_window_objects  *main_win =
    get_main_window_objects( );
    char *prog_name = get_prog_name( );
    Display *display = get_display( );
    CONTOUR contour = get_contour( );
    SKELETON *first_skelet = get_first_skelet( );
    unsigned char   *img = get_img( );
    int    img_width = get_img_width( ), img_height =
    get_img_height( ),
           img_depth = get_img_depth( );
    unsigned short  *dist_img = get_dist_img( );
    int    load_mag = get_load_mag( );
    int    row, col,dep,diln;
    int    i, j, l, h, k, m, index, offs;
    float  x, y, z, dz, del, val, val_l, val_h;
    float  xmin, xmax, ymin, ymax;
    int    inpolygon( );
    int    inpolygon_fast( );
    LINE        *line = NULL;
    unsigned char **read_img = NULL, *tmp = NULL;
    char * slice_str = NULL;
    ILIST *list = NULL;
    GFree(img);
    img = NULL;
    set_img(NULL);
    free_list(first_skelet);
    first_skelet = NULL;
    set_first_skelet(NULL);
    GFree(dist_img);
    dist_img = NULL;
    set_dist_img(NULL);
    if(contour.num_slices <= 0)
        return;
    /* fill in the contour to make img */
    /* print_1contour(contour); */
    /* allocat memory for imgs */
    read_img = (unsigned char **) calloc (contour.num_slices,
    sizeof(unsigned char *));
    if(!read_img)
    {
        fprint(stderr,"%s: cannot allocate memory for
        images\n",prog_name);
        return;
    }
    for(j=0;j<contour.num_slices;j++)
    {
        read_img[j] = (unsigned char *) calloc (img_width *
        img_height, sizeof(unsigned char));
        if(read_img[j] == NULL)
        {
```

```
            for(i=0;i<j;i++)
                GFree(read_img[i]);
            GFree(read_img);
            fprintf(stderr,"%s: cannot allocate memory for
            images\n",prog_name);
            return;
        }
    }
    /* clear images */
    for(i=0;i<contour.num_slices;i++)
    for(j=0; j< (img_width*img_height); j++)
    {
        read_img[i][j] = 0;
    }
    fprintf(stderr,"%s: starting filling the contour . . .
    \n",prog_name);
    /* fill the images */
    for(i=0;i<contour.num_slices;i++)
    {
    /*
     * the lines
     *
    line = (LINE *) calloc(contour.num_vert[i],
    sizeof(LINE));
    if(line == NULL)
    {
        for(j=0;j<contour.num_slices;j++)
            GFree(read_img[j]);
        GFree(read_img);
        fprintf(stderr,"%s: cannot allocate memory for
        images\n",prog_name);
        return;
    }
    xmin = xmax = contour.x[i][0];
    ymin = ymax = contour.y[i][0];
    for(j=0;j<contour.num_vert[i];j++)
    {
        if(j < (contour.num_vert[i]-1))
        {
            line[j].x1 = contour.x[i][j];
            line[j].y1 = contour.y[i][j];
            line[j].x2 = contour.x[i][j+1];
            line[j].y2 = contour.y[i][j+1];
        }
        else
        {
            line[j].x1 = contour.x[i][j];
            line[j].y1 = contour.y[i][j];
            line[j].x2 = contour.x[i][0];
            line[j].y2 = contour.y[i][0];
        }
        if( line[j].x1 == line[j].x2)
        {
            line[j].a = HUGE_VAL;
            line[j].c = line[j].x1;
        }
        else
        {
            line[j].a = (line[j].y2 -
            line[j].y1)/(line[j].x2 - line[j].x1);
            line[j].c = line[j].y1 -
            line[j.x1 = (line[j].y2 -
            line[j].y1)/(line[j].x2 - line[j].x1);
        }
        if(contour.x[i][j] < xmin)
            xmin = contour.x[i][j];
        if(contour.x[i][j] > xmax)
            xmax = contour.x[i][j];
        if(contour.y[i][j] < ymin)
            ymin = contour.y[i][j];
        if(contour.y[i][j] > ymax)
            ymax = contour.y[i][j];
        /* fprintf(stdout,"line: %d: %f %f -> %f %f
        \n",i,
            line[j].x1, line[j].y1, line[j].x2,
            line[j].y2);*/
    }
    y = ymin;
    l = ymin - contour.min_y;
```

```
            h = ymax - contour.min_y;
            if ( h == (img_height - 1)) h--;
            k = xmin - contour.min_x;
            m = xmax - contour.min_x;
            if ( m == (img_width -1 )) m--;
            for(row = 1;row <= h; row++)
            {
                x = xmin;
                for(col = k;col <= m; col++)
                {
                    index = row*img_width + col;
                    val =
                    inpolygon((x+0.001),(y+0.001),line,
                    contour.num_vert[i]);
                    val+=
                    inpolygon((x-0.001),(y-0.001),line,
                    contour.num_vert[i]);
                    val+=
                    inpolygon((x+0.001),(y-0.001),line,
                    contour.num_vert[i]);
                    val+=
                    inpolygon((x-0.001),(y+0.001),line,
                    contour.num_vert[i]);
                    if( val > 1.0)
                    {
                        read_img[i][index] = 1;
                    }
                    else
                    {
                        read_img[i][index] = 0;
                    }
                    x += 1.0;
                }
                y += 1.0;
            }
            /* free line */
            GFree(line);
    }
    /* interpolate to equispaced 3D volume */
    img = (unsigned char *) calloc(img_width*img_height*img_depth,
    sizeof(unsigned char));
    if(img == NULL)
    {
        for(i=0;i<contour.num_slices;i++)
            GFree(read_img[i]);
        GFree(read_img);
        xv_set(main_win->main_window,
            FRAME_LEFT_FOOTER,*fill_contour: memory
            allocation for image failed*,
            NULL);
        return;
    }
    offs = 0;
    for(i=0;i<img_depth;i++)
    {
        z = i + contour.min_z;
        l = 0;
        if( z < contour.z[0] )
        {
            l = h = 0;
            del = 0.0;
            dx = 0.0;
        }
        else if (z > contour.z[contour.num_slices-1])
        {
            l = h = contour.num_slices - 1;
            del = 0.0;
            dz = 0.0;
        }
        else
        {
            h = contour.num_slices-1;
            l = h - 1;
            while(( contour.[l] > z ) && ( l > 0 ))
            {
                l--;
                h--;
            }
            dz = z - contour.z[l] ;
```

```
                    del = contour.z[h] – contour.z[1];
                }
                j = 0;
                for(k = 0; k < img_height; k++)
                {
                    for(m=0;m<img_width;m++)
                    {
                        if(del == 0.0 && dz == 0.0)
                        {
                            img[offs+j] = 0;
                        }
                        else
                        {
                            val_l = (float)((unsigned
                            int)read_img[l][j]);
                            val_h = (float)((unsigned
                            int)read_img[h][j]);
                            val = ( val_l*(del-dz) +
                            val_h*dx)/del;
                            img[offs+j] = floor((double)(val +
                            0.5));
                            /*
                            img[offs+j] = read_img[l][j];
                            */
                        }
                        j++;
                    }
                }
                offs += img_width*img_height;
            }
            for(i=0;i<contour.num_slices;i++)
                GFree(read_img[i]);
            GFree(read_img);
            /* dilate the region */
            fprintf(stderr,"dilating . . . \n");
            tmp = (unsigned char *) calloc (img_width *
            img_height*img_depth, sizeof(unsigned char));
            if(!tmp)
            {
                fprintf(stderr,"%s: cannot allocate memory for
                images\n",prog_name);
                return;
            }
            diln = floor(1.0*load_mag +0.5);
                for(j=1; j< diln; j++)
                {
                    for(dep = 0; dep < (img_depth); dep++)
                    {
                        for(row = 1;row < (img_height-1); row++)
                        {
                            for(col=1; col< (img_width-1); col++)
                            {
                                index = ((dep *img_height)
                                +row)*img_width + col;
                                if( (int) img(index) != (int)0)
                                {
                                    dil(tmp, col, row,
                                    dep,(int)(j%2));
                                }
                            }
                        }
                    }
                    memcpy(img,tmp,img_width*img_height*img_depth);
                }
                memcpy(tmp,img,img_width*img_height*img_depth);
            print_dimensions( );
            set_img(img);
            set_tmp_img(tmp);
            /*
             * make window array
             */
            slice_str = (char *) xv_get(main_win->slice_list,
            PANEL_VALUE);
            list = (ILIST *) atoil(slice_str);
            if(list == NULL)
            {
                i = contour.num_slices / 5;
                if( i < 10 && contour.num_slices > 10)
                    i = 10;
```

-continued

```
                printf("Null string list . . . Setting list count to
                    %d\n", i);
            }
            else
            {
                i = list->n;
                printf("Number of list slices: %d\n", i);
                FreeIlist(list);
            }
            make_window_array(i);
            printf("fill_contour: displaying the image . . . \n");
            display_status(DISPLAY_IMAGE, img);
            return;
        }
        int inpolygon(x, y, line, n)   /* point(x,y,z) struct LINE and % of
        lines int the LINE struct */
        float x;
        float y;
LINE    *line;
int     n:
{
        int     i;
        int     in_out = 0;
        int     in_count = 0;
        float   xint;
        CONTOUR contour = get_contour( );
        if(x < contour.min_x || x > contour.max_x || y < contour.min_y
        || y > contour.max_y)
                return (int)0;
        in_count = 0;
        for(i=0; i< n; i++)
        {
                if( (y-line[i].y1)*(y-line[i].y2) > 0 )
                        continue;
                if(line[i].a == HUGE_VAL)
                {
                        int = line[i].x1;
                        if( xint == x)
                        {
                            in_out = 1;
                            return(in_out);
                        }
                        else if((x > xint) && (y != line[i].y2))
                            in_count ++;
                }
                else if (line[i].a == 0.0)
                {
                        if(line[i].y1 == y)
                        {
                            if( (x-line[i].x1)*(x-line[i].x2) <=0)
                            {
                                in_out =1;
                                return(in_out);
                            }
                        }
                }
                else
                {
                        int = (y - line[i].x)/line[i].a;
                        if( y == line[i].y1 && x == line[i].x1)
                        {
                            in_out = 1;
                            return(in_out);
                        }
                        else if((y != line[i].y1) && (y != line[i].y2)
                        && (x> xint))
                            in_count ++;
                }
        }
        if((in_count % 2) == 0)
                in_out = 0;
        else
                in_out = 1;
        return (in_out);
}
#define MINIMUM(x,y) (((x) < (y)) ? (x) : (y) )
#define MAXIMUM(x,y) (((x) > (y)) ? (x) : (y) )
int inpolygon_fast(x, y, polyv, np)
float x, y;
```

-continued

```
LINE *polyv;
int np;
{
/*
    polyv = (np.2) array of polygon vertices, either clockwise or
        counter-clockwise order. Polygon must be convex.
    x,y = point coordinates.
    return 0 if point is outside polygon, 1 if inside.
*/
    float x1, y1, x2, y2, k;
    int i, pos;
    pos = -1;
    for(i=0;i<np;i++)
    {
        x1 = polyv[i].x1;
        y1 = polyv[i].y1;
        x2 = polyv[i].x2;
        y2 = polyv[i].y2;
        k = (x*(y1-y2) + y * (x2-x1) + x1*y2-y1*x2); /* Side of
        line point is on */
        if ( (k == 0.0) /* On line? */
        {
            if ( ( (y < MINIMUM(y1, y2) ) || (y > MAXIMUM(y)
            , y2 ) ) ||
                    (x < MINIMUM(x1 , x2) ) || (x >
                    MAXIMUM(x1 , x2) ) )
            {
                return (0);
            }
        }
        else
        {
            k = k > 0.0;        /* if on right side
            */
            if (pos < 0) pos = k ;
            if (pos != k)
                    return (0);
        }
    }
    return(1);
}
#define INDEX3D(i,j,k) (((((i)*img_height) + (j))*img_width) + (k))
void dil(image, cols, rows, deps, mod)
unsigned char *image;
int cols, rows, deps,mod;
{
    int  img_width = get_img_width( ), img_height =
    get_img_height( ), img_depth = get_img_depth( );
    if( cols >= (img_width-1) || cols <1 || rows <1 || rows >=
    (img_height-1))
    {
        return;
    }
    *(image + INDEX3D(deps,rows ,cols)) = 1;
    if(cols < (img_width-1))
        *(image + INDEX3D(deps,rows ,cols +1)) = 1;
    if(cols > 0)
        *(image + INDEX3D(deps,rows ,cols -1)) = 1;
    if(rows > 0)
        *(image + INDEX3D(deps,rows -1,cols )) = 1;
    if(rows < (img_height-1))
        *(image + INDEX3D(deps,rows +1,cols )) = 1;
    if(deps > 0)
        *(image + INDEX3D(deps-1,rows,cols )) = 1;
    if(deps < (img_depth-1))
        *(image + INDEX3D(deps+1,rows,cols )) = 1;
    if( mode == 0)
    {
        if(cols < (img_width-1)) && (rows < (img_height-1)))
            *(image + INDEX3D(deps,rows +1,cols +1)) = 1;
        if((cols > 0) && (rows < (img_height-1)))
            *image + INDEX3D(deps,rows +1,cols -1)) = 1;
        if((cols > 0) && (rows >0))
            *(image + INDEX3D(deps,rows -1, cols -1)) = 1;
        if((cols < (img_width-1)) && (rows >0))
            *(image + INDEX3D(deps,rows -1, cols +1)) = 1;
        if((cols < (img_width-1)) && (rows < (img_height-1)) &&
        (deps >0))
            *(image + INDEX3D(deps-1,rows +1,cols +1)) = 1;
```

-continued

```
            if((cols > 0) && (rows < (img_height-1)) && (deps >0))
                *(image + INDEX3D(deps-1,rows +1,cols -1)) = 1;
            if((cols > 0) && (rows >0) && (deps > 0))
                *(image + INDEX3D(deps-1,rows -1,cols -1)) = 1;
            if((cols < (img_width-1)) && (rows >0) &&(deps >0))
                *(image + INDEX3D(deps-1,rows -1, cols +1)) = 1;
            if((cols < (img_width-1)) && (rows < (img_height-1)) &&
            (deps <(img_depth-1))
                *(image + INDEX3D(deps+1,rows +1,cols +1)) = 1;
            if((cols > 0) && (rows < (img_height-1)) &&
            (deps<(img_depth-1)))
                *(image + INDEX3D(deps+1,rows +1,cols -1)) = 1;
            if((cols > 0) && (rows >0) && (deps < (img_depth-1))
                *(image + INDEX3D(deps+1,rows -1,cols -1)) = 1;
            if((cols < (img_width-1)) && (rows >0) &&
            (deps<(img_depth-1)))
                *(image + INDEX3D(deps+1,rows -1,cols +1)) = 1;
    }
    return;
}
/*
 * g3dplan.c - Notify and event callback functions and main( )
 */
#include "includes.h"
#include "g3dplan_ui.h"
#include "g3dplan.h"
main(int argc, char **argv)
{
    g3dplan_main_window_objects *G3dplan_main_window =
    NULL;
    g3dplan_sub_window_objects *G3dplan_sub_window = NULL;
    void int_contour(void);
    void set_canvas(void);
    void set_main_window_objects
    (g3dplan_main_window_objects *);
    void set_sub_window_objects(g3dplan_sub_window_objects *);
    void set_prog_name(char *);
    void int_window_array( );
    Notify_value main_window_destroy(Notify_client,
    Destroy_status);
    Notify_value sub_window_destroy(Notify_client, Destroy_status);
    /*
     * Initialize XView
     */
    xv_int(XV_INT_ARGC_PTR_ARGV, &argc, argv, NULL);
    INSTANCE = xv_unique_key( );
    /*
     * Initialize user interface components.
     * Do NOT edit the object initializations by hand.
     */
    G3dplan_main_window =
    g3dplan_main_window_objects_initialize(NULL, NULL);
    G3dplan_sub_window =
    g3dplan_sub_window_objects_initialize(NULL,
    G3dplan_main_window->main_window);
    set_main_window_objects(G3dplan_main_window);
    set_sub_window_objects(G3dplan_sub_window);
    set_prog_name(argv[0]);
    /*
     * initialize canvas
     */
    set_canvas( );
    init_window_array( ),
    init_contour( );
    /*
     * intercept quit
     */
    notify_interpose_destroy_func(G3dplan_sub_window->
    sub_window, sub_window_destroy);
    notify_interpose_destroy_func(G3dplan_main_window->
    main_window, main_window_destroy);
    /*
     * Turn control over to XView.
     */
    xv_main_loop(G3dplan_main_window->main_window);
    printf("g3dplan: bye bye . . . \n");
}
/*
 * g3dplan_ui.c = User interface object initialization functions.
 * This file was generated by 'gxv' from 'g3dplan.G'.
```

```
 * DO NOT EDIT BY HAND.
 */
#include <stdio.h>
#include <sys/param.h>
#include <sys/types.h>
#include <xview/xview.h>
#include <xview/canvas.h>
#include <xview/panel.h>
#include <xview/scrollbar.h>
#include <xview/svrimage.h>
#include <xview/termsw.h>
#include <xview/text.h>
#include <xview/tty.h>
#include <xview/xv_xrect.h>
#include "g3dplan_ui.h"
/*
 * Initialize an instance of object 'main_window'.
 */
g3dplan_main_window_objects *
g3dplan_main_window_objects_initialize
(g3dplan_main_window_objects *ip,
Xv_opaque owner)
{
    if (!ip && !(ip = (g3dplan_main_window_objects *) calloc(1,
        sizeof (g3dplan_main_window_objects))))
            return (g3dplan_main_window_objects *) NULL;
    if (!ip->main_window)
        ip->main_window =
            g3dplan_main_window_main_window_create(ip, owner);
    if (!ip->main_panel)
        ip->main_panel =
            g3dplan_main_window_main_panel_create(ip,
            ip->main_window);
    if (!ip->load)
        ip->load = g3dplan_main_window_load_create(ip,
            ip->main_panel);
    if (!ip->fill_contour)
        ip->fill_contour =
            g3dplan_main_window_fill_contour_create(ip,
            ip->main_panel);
    if (!ip->thining)
        ip->thining = g3dplan_main_window_thining_create(ip,
            ip->main_panel);
    if (!ip->display_update)
        ip->display_update =
            g3dplan_main_window_display_update_create(ip,
            ip->main_panel);
    if (!ip->step)
        ip->step = g3dplan_main_window_step_create(ip,
            ip->main_panel);
    if (!ip->make_shots)
        ip->make_shots =
            g3dplan_main_window_make_shots_create(ip,
            ip->main_panel);
    if (!ip->show_plan)
        ip->show_plan =
            g3dplan_main_window_show_plan_create(ip,
            ip->main_panel);
    if (!ip->show_3d)
        ip->show_3d = g3dplan_main_window_show_3d_create(ip,
            ip->main_panel);
    if (!ip->plus)
        ip->plus = g3dplan_main_window_plus_create(ip,
            ip->main_panel);
    if (!ip->minus)
        ip->plus = g3dplan_main_window_minus_create(ip,
            ip->main_panel);
    if (!ip->file_name)
        ip->file_name =
            g3dplan_main_window_file_name_create(ip,
            ip->main_panel);
    if (!ip->display_mag)
        ip->display_mag =
            g3dplan_main_window_display_mag_create(ip,
            ip->main_panel);
    if (!ip->load_mag)
        ip->load_mag =
            g3dplan_main_window_load_mag_create(ip,
            ip->main_panel);
```

```
        if (!ip->x)
                ip->x = g3dplan_main_window_x_create(ip,
                ip->main_panel);
        if (!ip->y)
                ip->y = g3dplan_main_window_y_create(ip,
                ip->main_panel);
        if (!ip->z)
                ip->z = g3dplan_main_window_z_create(ip,
                ip->main_panel);
        if (!ip->r)
                irp->r = g3dplan_main_window_r_create(ip,
                ip->main_panel);
        if (!ip->helmet)
                ip->helmet = g3dplan_main_window_helmet_create(ip,
                ip->main_panel);
        if (!ip->slice_number)
                ip->slice_number =
                g3dplan_main_window_slice_number_create(ip,
                ip->main_panel);
        if (!ip->slice_list)
                ip->slice_list =
                g3dplan_main_window_slice_list_create(ip,
                ip->main_panel);
        if (!ip->overlap)
                ip->overlap = g3dplan_main_window_overlap_create(ip,
                ip->main_panel);
        if (!ip->gap)
                ip->gap = g3dplan_main_window_gap_create(ip,
                ip->main_panel);
        if (!ip->skel)
                ip->skel = g3dpan_main_window_skel_create(ip,
                ip->main_panel);
        if (!ip->add_shots)
                ip->add_shots =
                g3dplan_main_window_add_shots_create(ip,
                ip->main_panel);
        if (!ip->stage)
                ip->stage = g3dplan_main_window_stage_create(ip,
                ip->main_panel);
        if (!ip->cancel)
                ip->cancel = g3dplan_main_window_cancel_create(ip,
                ip->main_panel);
        window_fit_height(ip->main_panel);
        if (!ip->main_canvas)
                ip->main_canvas =
                g3dplan_main_window_main_canvas_create(ip,
                ip->main_window);
        return ip;
}
/*
 * Create object 'main_window' in the specified instance.
 */
Xv_opaque
g3dplan_main_window_main_window_create
(g3dplan_main_window_objects *ip,
Xv_opaque owner)
{
        Xv_opaque    obj;
        Xv_opaque             main_window_image;
        static unsigned short  main_window_bits( ) = (
#include "g3dplan.icon"
        };
        main_window_image = xv_create(XV_NULL,
        SERVER_IMAGE,
                SERVER_IMAGE_DEPTH, 1,
                SERVER_IMAGE_BITS, main_window_bits,
                XV_WIDTH, 64,
                XV_HEIGHT, 64,
                NULL);
        obj = xv_create(owner, FRAME,
                XV_KEY_DATA, INSTANCE, ip,
                XV_WIDTH, 700,
                XV_HEIGHT, 800,
                XV_LABEL, "g3Dplan",
                FRAME_SHOW_FOOTER, TRUE,
                FRAME_SHOW_RESIZE_CORNER, FALSE,
                FRAME_ICON, xv_create(XV_NULL, ICON,
                        ICON_IMAGE, main_window_image,
                        NULL),
```

-continued

```
            NULL);
        return obj;
}
/*
 * Create object 'main_panel' in the specified instance.
 */
Xv_opaque
g3dplan_main_window_main_panel_create
(g3dplan_main_window_objects *ip,
Xv_opaque owner)
{
        Xv_opaque    obj;
        obj = xv_create(owner, PANEL,
            XV_KEY_DATA, INSTANCE, ip,
            XV_X, 0,
            XV_Y, 0,
            XV_WIDTH, WIN_EXTEND_TO_EDGE,
            XV_HEIGHT, 100,
            WIN_BORDER, TRUE,
            NULL);
        return obj;
}
/*
 * Create object 'load' in the specified instance.
 */
Xv_opaque
g3dplan_main_window_load_create
(g3dplan_main_window_objects *ip,
Xv_opaque owner)
{
        extern void       load_callback(Panel_item, Event *);
        Xv_opaque    obj;
        obj = xv_create(owner, PANEL_BUTTON,
            XV_KEY_DATA, INSTANCE, ip,
            PANEL_LABEL_STRING, "Load",
            PANEL_NOTIFY_PROC, load_callback,
            NULL);
        return obj;
}
/*
 * Create object 'fill_contour' in the specified instance.
 */
Xv_opaque
g3dplan_main_window_fill_contour_create
(g3dplan_main_window_objects
*ip, Xv_opaque owner)
{
        extern void       fill_contour_callback(Panel_item, Event
        *);
        Xv_opaque    obj;
        obj = xv_create(owner, PANEL_BUTTON,
            XV_KEY_DATA, INSTANCE, ip,
            PANEL_LABEL_STRING, "Fill Contour",
            PANEL_NOTIFY_PROC, fill_contour_callback,
            NULL);
        return obj;
}
/*
 * Create object 'thining' in the specified instance.
 */
Xv_opaque
g3dplan_main_window_thining_create
(g3dplan_main_window_objects *ip,
Xv_opaque owner)
{
        extern void       thining_callback(Panel_item, Event *);
        Xv_opaque    obj;
        obj = xv_create(owner, PANEL_BUTTON,
            XV_KEY_DATA, INSTANCE, ip,
            PANEL_LABEL_STRING, "Thining",
            PANEL_NOTIFY_PROC, thining_callback,
            NULL);
        return obj;
}
/*
 * Create object 'display_update' in the specified instance.
 */
Xv_opaque
g3dplan_main_window_display_update_create
```

-continued

```
(g3dplan_main_window_objects
*ip, Xv_opaque owner)
{
    extern void        display_update_callback(Panel_item,
        Event *);
    Xv_opaque    obj;
    obj = xv_create(owner, PANEL_BUTTON,
        XV_KEY_DATA, INSTANCE, ip,
        PANEL_LABEL_STRING, "Display Update",
        PANEL_NOTIFY_PROC, display_update_callback,
        NULL);
    return obj;
}
/*
 * Create object 'step' in the specified instance
 */
Xv_opaque
g3dplan_main_window_step_create
(g3dplan_main_window_objects *ip, Xv_opaque owner)
{
    extern void        step_callback(Panel_item, Event *);
    Xv_opaque    obj;
    obj = xv_create(owner, PANEL_BUTTON,
        XV_KEY_DATA, INSTANCE, ip,
        PANEL_LABEL_STRING, "Step",
        PANEL_NOTIFY_PROC, step_callback,
        NULL);
    return obj;
}
/*
 * Create object 'make_shots' in the specified instance.
 */
Xv_opaque
g3dplan_main_window_make_shots_create
(g3dplan_main_window_objects *ip, Xv_opaque owner)
{
    extern void        make_shots_callback(Panel_item, Event
        *);
    Xv_opaque    obj;
    obj = xv_create(owner, PANEL_BUTTON,
        XV_KEY_DATA, INSTANCE, ip,
        PANEL_LABEL_STRING, "Make Shots",
        PANEL_NOTIFY_PROC, make_shots_callback,
        NULL);
    return obj;
}
/*
 * Create object 'show_plan' in the specified instance.
 */
Xv_opaque
g3dplan_main_window_show_plan_create
(g3dplan_main_window_objects *ip, Xv_opaque owner)
{
    extern void        show_plan_callback(Panel_item, Event
        *);
    Xv_opaque    obj;
    obj = xv_create(owner, PANEL_BUTTON,
        XV_KEY_DATA, INSTANCE, ip,
        PANEL_LABEL_STRING, "Show Plan",
        PANEL_NOTIFY_PROC, show_plan_callback,
        NULL);
    return obj;
}
/*
 * Create object 'show_3d' in the specified instance.
 */
Xv_opaque
g3dplan_main_window_show_3d_create
(g3dplan_main_window_objects *ip, Xv_opaque owner)
{
    extern void        show_3d_callback(Panel_item, Event *);
    Xv_opaque    obj;
    obj = xv_create(owner, PANEL_BUTTON,
        XV_KEY_DATA, INSTANCE, ip,
        PANEL_LABEL_STRING, "Show 3D View",
        PANEL_NOTIFY_PROC, show_3d_callback,
        NULL);
    return obj;
}
```

```
/*
 * Create object 'plus' in the specified instance.
 */
Xv_opaque
g3dplan_main_window_plus_create
(g3dplan_main_window_objects *ip, Xv_opaque owner)
{
    extern void      plus_callback(Panel_item, Event *);
    Xv_opaque   obj;
    obj = xv_create(owner, PANEL_BUTTON,
        XV_KEY_DATA, INSTANCE, ip,
        PANEL_LABEL_STRING, "+",
        PANEL_NOTIFY_PROC, plus_callback,
        NULL);
    return obj;
}
/*
 * Create object 'minus' in the specified instance.
 */
Xv_opaque
g3dplan_main_window_minus_create
(g3dplan_main_window_objects *ip, Xv_opaque owner)
{
    extern void      minus_callback(Panel_item, Event *);
    Xv_opaque   obj;
    obj = xv_create(owner, PANEL_BUTTON,
        XV_KEY_DATA, INSTANCE, ip,
        PANEL_LABEL_STRING, "-",
        PANEL_NOTIFY_PROC, minus_callback,
        NULL);
    return obj;
}
/*
 * Create object 'file_name' in the specified instance.
 */
Xv_opaque
g3dplan_main_window_file_name_create
(g3dplan_main_window_objects *ip, Xv_opaque owner)
{
    Xv_opaque   obj;
    obj = xv_create(owner, PANEL_TEXT,
        XV_KEY_DATA, INSTANCE, ip,
        PANEL_VALUE_DISPLAY_LENGTH, 15,
        PANEL_VALUE_STORED_LENGTH, 80,
        PANEL_LABEL_STRING, "File Name:",
        PANEL_LAYOUT, PANEL_HORIZONTAL,
        PANEL_READ_ONLY, FALSE,
        NULL);
    return obj;
}
/*
 * Create object 'display_mag' in the specified instance.
 */
Xv_opaque
g3dplan_main_window_display_mag_create
(g3dplan_main_window_objects *ip, Xv_opaque owner)
{
    Xv_opaque   obj;
    obj = xv_create(owner, PANEL_NUMERIC_TEXT,
        XV_KEY_DATA, INSTANCE, ip,
        PANEL_VALUE_DISPLAY_LENGTH, 2,
        PANEL_VALUE_STORED_LENGTH, 40,
        PANEL_LABEL_STRING, "Disp. Mag:",
        PANEL_LAYOUT, PANEL_HORIZONTAL,
        PANEL_MAX_VALUE, 20,
        PANEL_MIN_VALUE, 1,
        PANEL_VALUE, 1,
        PANEL_READ_ONLY, FALSE,
        NULL);
    return obj;
}
/*
 * Create object 'load_mag' in the specified instance.
 */
Xv_opaque
g3dplan_main_window_load_mag_create
(g3dpan_main_window_objects *ip,
Xv_opaque owner)
{
```

```
        Xv_opaque   obj;
        obj = xv_create(owner, PANEL_NUMERIC_TEXT,
            XV_KEY_DATA, INSTANCE, ip,
            PANEL_VALUE_DISPLAY_LENGTH, 2,
            PANEL_VALUE_STORED_LENGTH, 10,
            PANEL_LABEL_STRING, "Load Mag:",
            PANEL_LAYOUT, PANEL_HORIZONTAL,
            PANEL_MAX_VALUE, 10,
            PANEL_MIN_VALUE, 1,
            PANEL_VALUE, 1,
            PANEL_READ_ONLY, FALSE,
            NULL);
        return obj;
}
/*
 * Create object 'x' in the specified instance.
 */
Xv_opaque
g3dplan_main_window_x_create
(g3dplan_main_window_objects *ip, Xv_opaque owner)
{
        Xv_opaque   obj;
        obj = xv_create(owner, PANEL_TEXT,
            XV_KEY_DATA, INSTANCE, ip,
            PANEL_VALUE_DISPLAY_LENGTH, 4,
            PANEL_VALUE_STORED_LENGTH, 40,
            PANEL_LABEL_STRING, "x:",
            PANEL_LAYOUT, PANEL_HORIZONTAL,
            PANEL_VALUE, "0",
            PANEL_READ_ONLY, FALSE,
            NULL);
        return obj;
}
/*
 * Create object 'y' in the specified instance.
 */
Xv_opaque
g3dplan_main_window_y_create
(g3dplan_main_window_objects *ip, Xv_opaque owner)
{
        Xv_object   obj;
        obj = xv_create(owner, PANEL_TEXT,
            XV_KEY_DATA, INSTANCE, ip,
            PANEL_VALUE_DISPLAY_LENGTH, 4,
            PANEL_VALUE_STORED_LENGTH, 40,
            PANEL_LABEL_STRING, "y:",
            PANEL_LAYOUT, PANEL_HORIZONTAL,
            PANEL_VALUE, "0",
            PANEL_READ_ONLY, FALSE,
            NULL);
        return obj;
}
/*
 * Create object 'z' in the specified instance.
 */
Xv_opaque
g3dplan_main_window_z_create
(g3dplan_main_window_objects *ip, Xv_opaque owner)
{
        Xv_opaque   obj;
        obj = xv_create(owner, PANEL_TEXT,
            XV_KEY_DATA, INSTANCE, ip,
            PANEL_VALUE_DISPLAY_LENGTH, 4,
            PANEL_VALUE_STORED_LENGTH, 40,
            PANEL_LABEL_STRING, "z:",
            PANEL_LAYOUT, PANEL_HORIZONTAL,
            PANEL_VALUE, "0",
            PANEL_READ_ONLY, FALSE,
            NULL);
        return obj;
}
/*
 * Create object 'r' in the specified instance.
 */
Xv_opaque
g3dplan_main_window_r_create
(g3dplan_main_window_objects *ip, Xv_opaque owner)
{
        Xv_opaque   obj;
```

-continued

```
        obj = xv_create(owner, PANEL_TEXT,
            XV_KEY_DATA, INSTANCE, ip,
            PANEL_VALUE_DISPLAY_LENGTH, 4,
            PANEL_VALUE_STORED_LENGTH, 40,
            PANEL_LABEL_STRING, "r:",
            PANEL_LAYOUT, PANEL_HORIZONTAL,
            PANEL_VALUE, "0",
            PANEL_READ_ONLY, FALSE,
            NULL);
        return obj;
}
/*
 * Create object 'helmet' in the specified instance.
 */
Xv_opaque
g3dplan_main_window_helmet_create
(g3dplan_main_window_objects *ip, Xv_opaque owner)
{
    Xv_opaque   obj;
        obj = xv_create(owner, PANEL_TEXT,
            XV_KEY_DATA, INSTANCE, ip,
            PANEL_VALUE_DISPLAY_LENGTH, 4,
            PANEL_VALUE_STORED_LENGTH, 40,
            PANEL_LABEL_STRING, "helmet:",
            PANEL_LAYOUT, PANEL_HORIZONTAL,
            PANEL_VALUE, "0",
            PANEL_READ_ONLY, FALSE,
            NULL);
        return obj;
}
/*
 * Create object 'slice_number' in the specified instance.
 */
Xv_opaque
g3dplan_main_window_slice_number_create
(g3dplan_main_window_objects *ip, Xv_opaque owner)
{
    Xv_opaque   obj;
        obj = xv_create(owner, PANEL_NUMERIC_TEXT,
            XV_KEY_DATA, INSTANCE, ip,
            PANEL_VALUE_DISPLAY_LENGTH, 3,
            PANEL_VALUE_STORED_LENGTH, 20,
            PANEL_LABEL_STRING, "Slice:",
            PANEL_LAYOUT, PANEL_HORIZONTAL,
            PANEL_MAX_VALUE, 100,
            PANEL_MIN_VALUE, 0,
            PANEL_VALUE, 0,
            PANEL_READ_ONLY, FALSE,
            NULL);
        return obj;
}
/*
 * Create object 'slice_list' in the specified instance.
 */
Xv_opaque
g3dplan_main_window_slice_list_create
(g3dplan_main_window_objects *ip, Xv_opaque owner)
{
    Xv_opaque   obj;
        obj = xv_create(owner, PANEL_TEXT,
            XV_KEY_DATA, INSTANCE, ip,
            PANEL_VALUE_DISPLAY_LENGTH, 15,
            PANEL_VALUE_STORED_LENGTH, 90,
            PANEL_LABEL_STRING, "Slice List:",
            PANEL_LAYOUT, PANEL_HORIZONTAL,
            PANEL_READ_ONLY, FALSE,
            NULL);
        return obj;
}
/*
 * Create object 'overlap' in the specified instance.
 */
Xv_opaque
g3dplan_main_window_overlap_create
(g3dplan_main_window_objects *ip, Xv_opaque owner)
{
    Xv_opaque   obj;
        obj = xv_create(owner, PANEL_NUMERIC_TEXT,
            XV_KEY_DATA, INSTANCE, ip,
```

```
            PANEL_VALUE_DISPLAY_LENGTH, 2,
            PANEL_VALUE_STORED_LENGTH, 20,
            PANEL_LABEL_STRING, "Overlap:",
            PANEL_LAYOUT, PANEL_HORIZONTAL,
            PANEL_MAX_VALUE, 100,
            PANEL_MIN_VALUE, 0,
            PANEL_VALUE, 0,
            PANEL_READ_ONLY, FALSE,
            NULL);
      return obj;
}
/*
 * Create object 'gap' in the specified instance.
 */
Xv_opaque
g3dplan_main_window_gap_create
(g3dplan_main_window_objects *ip, Xv_opaque owner)
{
      Xv_opaque   obj;
      obj = xv_create(owner, PANEL_NUMERIC_TEXT,
            XV_KEY_DATA, INSTANCE, ip,
            PANEL_VALUE_DISPLAY_LENGTH, 2,
            PANEL_VALUE_STORED_LENGTH, 20,
            PANEL_LABEL_STRING, "Gap:",
            PANEL_LAYOUT, PANEL_HORIZONTAL,
            PANEL_MAX_VALUE, 10,
            PANEL_MIN_VALUE, 0,
            PANEL_VALUE, 0,
            PANEL_READ_ONLY, FALSE,
            NULL);
      return obj;
}
/*
 * Create object 'skel' in the specified instance.
 */
Xv_opaque
g3dplan_main_window_skel_create
(g3dplan_main_window_objects *ip, Xv_opaque owner)
{
      extern void      skel_callback(Panel_item, Event *);
      Xv_opaque   obj;
      obj = xv_create(owner, PANEL_BUTTON,
            XV_KEY_DATA, INSTANCE, ip,
            PANEL_LABEL_STRING, "Skeleton",
            PANEL_NOTIFY_PROC, skel_callback,
            NULL);
      return obj;
}
/*
 * Create object 'add_shots' in the specified instance.
 */
Xv_opaque
g3dplan_main_window_add_shots_create
(g3dplan_main_window_objects *ip, Xv_opaque owner)
{
      extern void      add_shots_callback(Panel_item, Event
      *);
      Xv_opaque   obj;
      obj = xv_create(owner, PANEL_BUTTON,
            XV_KEY_DATA, INSTANCE, ip,
            PANEL_LABEL_STRING, "Add Shots",
            PANEL_NOTIFY_PROC, add_shots_callback,
            NULL);
      return obj;
}
/*
 * Create object 'stage' in the specified instance.
 */
Xv_opaque
g3dplan_main_window_stage_create
(g3dplan_main_window_objects *ip, Xv_opaque owner)
{
      extern void      stage_callback(Panel_item, Event *);
      extern int get_stage( );
      int stage = get_stage( );
      char str[64];
      Xv_opaque   obj;
      sprintf(str,"Stage (%d)", stage);
      obj = xv_create(owner, PANEL_BUTTON,
```

-continued

```
        XV_KEY_DATA, INSTANCE, ip,
        PANEL_LABEL_STRING, str,
        PANEL_NOTIFY_PROC, stage_callback,
        NULL);
    return obj;
}
/*
 * Create object 'cancel' in the specified instance.
 */
Xv_opaque
g3dplan_main_window_cancel_create
(g3dplan_main_window_objects *ip, Xv_opaque owner)
{
    extern void     cancel_callback(Panel_item, Event *);
    Xv_opaque   obj;
    obj = xv_create(owner, PANEL_BUTTON,
        XV_KEY_DATA, INSTANCE, ip,
        PANEL_LABEL_STRING, "CancelLastShot",
        PANEL_NOTIFY_PROC, cancel_callback,
        NULL);
    return obj;
}
/*
 * Create object 'main_canvas' in the specified instance.
 */
Xv_opaque
g3dplan_main_window_main_canvas_create
(g3dplan_main_window_objects *ip, Xv_opaque owner)
{
    Xv_opaque   obj;
    obj = xv_create(owner, CANVAS,
        XV_KEY_DATA, INSTANCE, ip,
        XV_X, 0,
        XV_Y,   (int)xv_get(ip->main_panel, XV_Y) +
                (int)xv_get(ip->main_panel, XV_HEIGHT) + 2,
        XV_WIDTH, WIN_EXTEND_TO_EDGE,
        XV_HEIGHT, WIN_EXTEND_TO_EDGE,
        NULL);
    xv_create(obj, SCROLLBAR, SCROLLBAR_DIRECTION,
    SCROLLBAR_HORIZONTAL, NULL);
    xv_create(obj, SCROLLBAR, SCROLLBAR_DIRECTION,
    SCROLLBAR_VERTICAL, NULL);
    /*
     * This line is here for backwards compatibility. It will be
     * remover for the next release.
     */
    xv_set(canvas_paint_window(obj), XV_KEY_DATA,
    INSTANCE, ip, NULL);
    return obj;
}
/*
 * Initialize an instance of object 'sub_window'.
 */
g3dplan_sub_window_objects *
g3dplan_sub_window_objects_initialize
(g3dplan_sub_window_objects *ip, Xv_opaque owner)
{
    if (!ip && !(ip = (g3dplan_sub_window_objects *) calloc(1,
    sizeof (g3dplan_sub_window_objects))))
        return (g3dplan_sub_window_objects *) NULL;
    if (!ip->sub_window)
        ip->sub_window =
        g3dplan_sub_window_sub_window_create(ip, owner);
    if (!ip->sub_panel)
        ip->sub_panel =
        g3dplan_sub_window_sub_panel_create(ip,
        ip->sub_window);
    if (!ip->alpha)
        ip->alpha = g3dplan_sub_window_alpha_create(ip,
        ip->sub_panel);
    if (!ip->beta)
        ip->beta = g3dplan_sub_window_beta_create(ip,
        ip->sub_panel);
    if (!ip->gamma)
        ip->gamma = g3dplan_sub_window_gamma_create(ip,
        ip->sub_panel);
    if (!ip->x)
        ip->x = g3dplan_sub_window_x_create(ip, ip->sub_panel);
    if (!ip->y)
```

-continued

```
        ip->y = g3dplan_sub_window_y_create(ip, ip->sub_panel);
    if (!ip->z)
        ip->z = g3dplan_sub_window_z_create(ip, ip->sub_panel);
    if (!ip->display_3d)
        ip->display_3d =
        g3dplan_sub_window_display_3d_create(ip,
            ip->sub_panel);
    if (!ip->sub_canvas)
        ip->sub_canvas =
        g3dplan_sub_window_sub_canvas_create(ip,
            ip->sub_window);
    return ip;
}
/*
 * Create object 'sub_window' in the specified instance.
 */
Xv_opaque
g3dplan_sub_window_sub_window_create
(g3dplan_sub_window_objects *ip, Xv_opaque owner)
{
    Xv_opaque    obj;
    Xv_opaque         sub_window_image;
    static unsigned short sub_window_bits( ) = (
#include "g3dplan.icon"
    };
    sub_window_image = xv_create(XV_NULL, SERVER_IMAGE,
        SERVER_IMAGE_DEPTH, 1,
        SERVER_IMAGE_BITS, sub_window_bits,
        XV_WIDTH, 64,
        XV_HEIGHT, 64,
        NULL);
    obj = xv_create(owner, FRAME,
        XV_KEY_DATA, INSTANCE, ip,
        XV_WIDTH, 450,
        XV_HEIGHT, 470,
        XV_LABEL, "3D View",
        XV_SHOW, FALSE,
        FRAME_SHOW_FOOTER, TRUE,
        FRAME_SHOW_RESIZE_CORNER, FALSE,
        FRAME_ICON, xv_create(XV_NULL, ICON,
            ICON_IMAGE, sub_window_image,
            NULL),
        NULL);
    return obj;
}
/*
 * Create object 'sub_panel' in the specified instance.
 */
Xv_opaque
g3dplan_sub_window_sub_panel_create
(g3dplan_sub_window_objects *ip, Xv_opaque owner)
{
    Xv_opaque    obj;
    obj = xv_create(owner, PANEL,
        XV_KEY_DATA, INSTANCE, ip,
        XV_X, 0,
        XV_Y, 0,
        XV_WIDTH, WIN_EXTEND_TO_EDGE,
        XV_HEIGHT, 70,
        WIN_BORDER, TRUE,
        NULL);
    return obj;
}
/*
 * Create object 'alpha' in the specified instance.
 */
Xv_opaque
g3dplan_sub_window_alpha_create
(g3dplan_sub_window_objects *ip, Xv_opaque owner)
{
    Xv_opaque    obj;
    obj = xv_create(owner, PANEL_NUMERIC_TEXT,
        XV_KEY_DATA, INSTANCE, ip,
        PANEL_VALUE_DISPLAY_LENGTH, 3,
        PANEL_VALUE_STORED_LENGTH, 5,
        PANEL_LABEL_STRING, "ALpha:",
        PANEL_LAYOUT, PANEL_HORIZONTAL,
        PANEL_MAX_VALUE, 360,
        PANEL_MIN_VALUE, 0,
```

```
        PANEL_VALUE, 0,
        PANEL_READ_ONLY, FALSE,
        NULL);
    return obj;
}
/*
 * Create object 'beta' in the specified instance.
 */
Xv_opaque
g3dplan_sub_window_beta_create(g3dplan_sub_window_objects *ip,
Xv_opaque owner)
{
    Xv_opaque  obj;
    obj = xv_create(owner, PANEL_NUMERIC_TEXT,
        XV_KEY_DATA, INSTANCE, ip,
        PANEL_VALUE_DISPLAY_LENGTH, 3,
        PANEL_VALUE_STORED_LENGTH, 5,
        PANEL_LABEL_STRING, "Beta: ",
        PANEL_LAYOUT, PANEL_HORIZONTAL,
        PANEL_MAX_VALUE, 360,
        PANEL_MIN_VALUE, 0,
        PANEL_VALUE, 0,
        PANEL_READ_ONLY, FALSE,
        NULL);
    return obj;
}
/*
 * Create object 'gamma' in the specified instance.
 */
Xv_opaque
g3dplan_sub_window_gamma_create
(g3dplan_sub_window_objects *ip, Xv_opaque owner)
{
    Xv_opaque  obj;
    obj = xv_create(owner, PANEL_NUMERIC_TEXT,
        XV_KEY_DATA, INSTANCE, ip,
        PANEL_VALUE_DISPLAY_LENGTH, 3,
        PANEL_VALUE_STORED_LENGTH, 5,
        PANEL_LABEL_STRING, "Gamma: ",
        PANEL_LAYOUT, PANEL_HORIZONTAL,
        PANEL_MAX_VALUE, 360,
        PANEL_MIN_VALUE, 0,
        PANEL_VALUE, 0,
        PANEL_READ_ONLY, FALSE,
        NULL);
    return obj;
}
/*
 * Create object 'x' in the specified instance.
 */
Xv_opaque
g3dplan_sub_window_x_create
(g3dplan_sub_window_objects *ip, Xv_opaque owner)
{
    Xv_opaque  obj;
    obj = xv_create(owner, PANEL_NUMERIC_TEXT,
        XV_KEY_DATA, INSTANCE, ip,
        PANEL_VALUE_DISPLAY_LENGTH, 3,
        PANEL_VALUE_STORED_LENGTH, 5,
        PANEL_LABEL_STRING, "X: ",
        PANEL_LAYOUT, PANEL_HORIZONTAL,
        PANEL_MAX_VALUE, 500,
        PANEL_MIN_VALUE, -500,
        PANEL_VALUE, 0,
        PANEL_READ_ONLY, FALSE,
        NULL);
    return obj;
}
/*
 * Create object 'y' in the specified instance.
 */
Xv_opaque
g3dplan_sub_window_y_create
(g3dplan_sub_window_objects *ip, Xv_opaque owner)
{
    Xv_opaque  obj;
    obj = xv_create(owner, PANEL_NUMERIC_TEXT,
        XV_KEY_DATA, INSTANCE, ip,
        PANEL_VALUE_DISPLAY_LENGTH, 3,
```

```
            PANEL_VALUE_STORED_LENGTH, 5,
            PANEL_LABEL_STRING, "Y: ",
            PANEL_LAYOUT, PANEL_HORIZONTAL,
            PANEL_MAX_VALUE, 500,
            PANEL_MIN_VALUE, -500,
            PANEL_VALUE, 0,
            PANEL_READ_ONLY, FALSE,
            NULL);
    return obj;
}
/*
 * Create object 'display_3d' in the specified instance.
 */
Xv_opaque
g3dplan_sub_window_display_3d_create
(g3dplan_sub_window_objects *ip, Xv_opaque owner)
{
    extern void       display_3d_callback(Panel_item, Event
        *);
    Xv_opaque   obj;
    obj = xv_create(owner, PANEL_BUTTON,
            XV_KEY_DATA, INSTANCE, ip,
            PANEL_LABEL_STRING, "Display",
            PANEL_NOTIFY_PROC, display_3d_callback,
            NULL);
    return obj;
}
/*
 * Create object 'z' in the specified instance.
 */
Xv_opaque
g3dplan_sub_window_z_create
(g3dplan_sub_window_objects *ip, Xv_opaque owner)
{
    Xv_opaque   obj;
    obj = xv_create(owner, PANEL_NUMERIC_TEXT,
            XV_KEY_DATA, INSTANCE, ip,
            PANEL_VALUE_DISPLAY_LENGTH, 3,
            PANEL_VALUE_STORED_LENGTH, 5,
            PANEL_LABEL_STRING, "Z: ",
            PANEL_LAYOUT, PANEL_HORIZONTAL,
            PANEL_MAX_VALUE, 500,
            PANEL_MIN_VALUE, -500,
            PANEL_VALUE, 0,
            PANEL_READ_ONLY, FALSE,
            NULL);
    return obj;
}
/*
 * Create object 'sub_canvas' in the specified instance.
 */
Xv_opaque
g3dplan_sub_window_sub_canvas_create
(g3dplan_sub_window_objects *ip, Xv_opaque owner)
{
    Xv_opaque   obj;
    obj = xv_create(owner, CANVAS,
            XV_KEY_DATA, INSTANCE, ip,
            XV_X, 0,
            XV_Y,   (int)xv_get(ip->sub_panel, XV_Y) +
                    (int)xv_get(ip->sub_panel, XV_HEIGHT) + 2,
            XV_WIDTH, WIN_EXTEND_TO_EDGE,
            XV_HEIGHT, WIN_EXTEND_TO_EDGE,
            NULL);
    xv_create(obj, SCROLLBAR, SCROLLBAR_DIRECTION,
    SCROLLBAR_HORIZONTAL, NULL);
    xv_create(obj, SCROLLBAR, SCROLLBAR_DIRECTION,
    SCROLLBAR_VERTICAL, NULL);
    /*
     * This line is here for backwards compatibility. It will be
     * removed for the next release.
     */
    xv_set(canvas_paint_window(obj), XV_KEY_DATA,
    INSTANCE, ip, NULL);
    return obj;
}
#ifndef g3dplan_HEADER
#define g3dplan_HEADER
/*
```

```
* g3dplan_ui.h - User interface object and function declarations.
* This file was generated by 'gxv' from 'g3dplan.G'.
* DO NOT EDIT BY HAND.
*/
extern Attr_attribute    INSTANCE;
typedef struct {
    Xv_opaque    main_window;
    Xv_opaque    main_panel;
    Xv_opaque    load;
    Xv_opaque    fill_contour;
    Xv_opaque    thining;
    Xv_opaque    display_update;
    Xv_opaque    step;
    Xv_opaque    make_shots;
    Xv_opaque    show_plan;
    Xv_opaque    show_3d;
    Xv_opaque    file_name;
    Xv_opaque    display_mag;
    Xv_opaque    load_mag;
    Xv_opaque    plus;
    Xv_opaque    minus;
    Xv_opaque    x;
    Xv_opaque    y;
    Xv_opaque    z;
    Xv_opaque    r;
    Xv_opaque    helmet;
    Xv_opaque    slice_number;
    Xv_opaque    slice_list;
    Xv_opaque    overlap;
    Xv_opaque    gap;
    Xv_opaque    skel;
    Xv_opaque    add_shots;
    Xv_opaque    stage;
    Xv_opaque    cancel;
    Xv_opaque    main_canvas;
} g3dplan_main_window_objects;
extern g3dplan_main_window_objects
*g3dplan_main_window_objects_initialize
(g3dplan_main_window_objects *, Xv_opaque);
extern Xv_opaque
g3dplan_main_window_main_window_create
(g3dplan_main_window_objects *, Xv_opaque);
extern Xv_opaque
g3dplan_main_window_main_panel_create
(g3dplan_main_window_objects *, Xv_opaque);
extern Xv_opaque
g3dplan_main_window_load_create
(g3dplan_main_window_objects *, Xv_opaque);
extern Xv_opaque
g3dplan_main_window_fill_contour_create
(g3dplan_main_window_objects *, Xv_opaque);
extern Xv_opaque
g3dplan_main_window_thining_create
(g3dplan_main_window_objects *, Xv_opaque);
extern Xv_opaque
g3dplan_main_window_display_update_create
(g3dplan_main_window_objects *, Xv_opaque);
extern Xv_opaque
g3dplan_main_window_step_create
(g3dplan_main_window_objects *, Xv_opaque);
extern Xv_opaque
g3dplan_main_window_make_shots_create
(g3dplan_main_window_objects *, Xv_opaque);
extern Xv_opaque
g3dplan_main_window_show_plan_create
(g3dplan_main_window_objects *, Xv_opaque);
extern Xv_opaque
g3dplan_main_window_show_3d_create
(g3dplan_main_window_objects *, Xv_opaque);
extern Xv_opaque
g3dplan_main_window_file_name_create
(g3dplan_main_window_objects *, Xv_opaque);
extern Xv_opaque
g3dplan_main_window_display_mag_create
(g3dplan_main_window_objects *, Xv_opaque);
extern Xv_opaque
g3dplan_main_window_load_mag_create
(g3dplan_main_window_objects *, Xv_opaque);
extern Xv_opaque
```

```
g3dplan_main_window_plus_create
(g3dplan_main_window_objects *, Xv_opaque);
extern Xv_opaque
g3dplan_main_window_minus_create
(g3dplan_main_window_objects *, Xv_opaque);
extern Xv_opaque
g3dplan_main_window_x_create(g3dplan_main_window_objects *,
Xv_opaque);
extern Xv_opaque
g3dplan_main_window_y_create(g3dplan_main_window_objects *,
Xv_opaque);
extern Xv_opaque
g3dplan_main_window_z_create(g3dplan_main_window_objects *,
Xv_opaque);
extern Xv_opaque
g3dplan_main_window_r_create(g3dplan_main_window_objects *,
Xv_opaque);
extern Xv_opaque
g3dplan_main_window_helmet_create
(g3dplan_main_window_objects *, Xv_opaque);
extern Xv_opaque
g3dplan_main_window_slice_number_create
(g3dplan_main_window_objects *, Xv_opaque);
extern Xv_opaque
g3dplan_main_window_slice_list_create
(g3dplan_main_window_objects *, Xv_opaque);
extern Xv_opaque
g3dplan_main_window_overlap_create
(g3dplan_main_window_objects *, Xv_opaque);
extern Xv_opaque
g3dplan_main_window_gap_create(g3dplan_main_window_objects *,
Xv_opaque);
extern Xv_opaque
g3dplan_main_window_skel_create
(g3dplan_main_window_objects *, Xv_opaque);
extern Xv_opaque
g3dplan_main_window_add_shots_create
(g3dplan_main_window_objects *, Xv_opaque);
extern Xv_opaque
g3dplan_main_window_stage_create
(g3dplan_main_window_objects *, Xv_opaque);
extern Xv_opaque
g3dplan_main_window_cancel_create
(g3dplan_main_window_objects *, Xv_opaque);
extern Xv_opaque
g3dplan_main_window_main_canvas_create
(g3dplan_main_window_objects *, Xv_opaque);
typedef struct {
        Xv_opaque       sub_window;
        Xv_opaque       sub_panel;
        Xv_opaque       alpha;
        Xv_opaque       beta;
        Xv_opaque       gamma;
        Xv_opaque       x;
        Xv_opaque       y;
        Xv_opaque       z;
        Xv_opaque       display_3d;
        Xv_opaque       sub_canvas;
} g3dplan_sub_window_objects;
extern g3dplan_sub_window_objects
*g3dplan_sub_window_objects_initialize
(g3dplan_sub_window_objects *, Xv_opaque);
extern Xv_opaque
g3dplan_sub_window_sub_window_create
(g3dplan_sub_window_objects *, Xv_opaque);
extern Xv_opaque
g3dplan_sub_window_sub_panel_create
(g3dplan_sub_window_objects *, Xv_opaque);
extern Xv_opaque
g3dplan_sub_window_alpha_create(g3dplan_sub_window_objects *,
Xv_opaque);
extern Xv_opaque
g3dplan_sub_window_beta_create(g3dplan_sub_window_objects *,
Xv_opaque);
extern Xv_opaque
g3dplan_sub_window_gamma_create
(g3dplan_sub_window_objects *, Xv_opaque);
extern Xv_opaque
g3dplan_sub_window_x_create(g3dplan_sub_window_objects *,
```

-continued

```
Xv_opaque),
extern Xv_opaque
g3dplan_sub_window_y_create(g3dplan_sub_window_objects *,
Xv_opaque),
extern Xv_opaque
g3dplan_sub_window_z_create(g3dplan_sub_window_objects *,
Xv_opaque),
extern Xv_opaque
g3dplan_sub_window_display_3d_create
(g3dplan_sub_window_objects *, Xv_opaque);
extern Xv_opaque
g3dplan_sub_window_sub_canvas_create
(g3dplan_sub_window_objects *, Xv_opaque);
typedef struct {
        Frame      *window;
        Canvas     *canvas;
        Window     *paint_window;
        int        count;
} g3dplan_window_array_objects;
#endif
;GIL-3
{
{
        :type              :base-window
        :name              main_window
        :owner             nil
        :width             700
        :height            800
        :background-color  **
        :foreground-color  **
        :label             "g3Dplan"
        :label-type        :string
        :initial-state     :open
        :show-footer       t
        :resizable         nil
        :icon-file         "g3dplan.icon"
        :icon-label        **
        :icon-mask-file    **
        :event-handler     nil
        :user-data         ( )
        :actions           ( )
}
{
        :type              :control-area
        :name              main_panel
        :owner             main_window
        :help              **
        :x                 0
        :y                 0
        :width             700
        :height            100
        :background        **
        :foreground        **
        :initial-state     :visible
        :show-border       t
        :menu              nil
        :event-handler     nil
        :user-data         ( )
        :actions           ( )
}
{
        :type              :button
        :name              load
        :owner             main_panel
        :help              **
        :x                 15
        :y                 15
        :width             46
        :height            19
        :constant-width    nil
        :button-type       :normal
        :foreground-color  **
        :label             "Load"
        :label-type        :string
        :initial-state     :active
        :menu              nil
        :notify-handler    load_callback
        :event-handler     nil
        :user-data         ( )
```

-continued

```
        :actions            {
            {
                :when               (main_window load)
                :to                 (Notify )
                :function_type      (main_window load)
                :arg_type           CallFunction
                :action             ( )
            }                       (load_callback)
        }
    }
}
{
    :type               :button
    :name               fill_contour
    :owner              main_panel
    :help               **
    :x                  65
    :y                  15
    :width              90
    :height             19
    :constant-width     nil
    :button-type        :normal
    :foreground-color   **
    :label              "Fill Contour"
    :label-type         :string
    :initial-state      :active
    :menu               nil
    :notify-handler     fill_contour_callback
    :event-handler      nil
    :user-data          ( )
    :actions            {
        {
            :from               (main_window fill_contour)
            :when               (Notify )
            :to                 (main_window fill_contour)
            :function_type      CallFunction
            :arg_type           ( )
            :action             (fill_contour_callback)
        }
    }
}
{
    :type               :button
    :name               thining
    :owner              main_panel
    :help               **
    :x                  160
    :y                  15
    :width              65
    :height             19
    :constant-width     nil
    :button-type        :normal
    :foreground-color   **
    :label              "Thining"
    :label-type         :string
    :initial-state      :active
    :menu               nil
    :notify-handler     thining_callback
    :event-handler      nil
    :user-data          ( )
    :actions            {
        {
            :from               (main_window thining)
            :when               (Notify )
            :to                 (main_window thining)
            :function-type      CallFunction
            :arg-type           ( )
            :action             (thining_callback)
        }
    }
}
{
    :type               :button
    :name               display_update
    :owner              main_panel
    :help               **
    :x                  235
    :y                  15
    :width              111
    :height             19
```

```
    :constant-width     nil
    :button-type        :normal
    :foreground-color   **
    :label              "Display Update"
    :label-type         :string
    :initial-state      :active
    :menu               nil
    :notify-handler     display_update_callback
    :event-handler      nil
    :user-data          ( )
    :actions            {
                            {
                            :from           (main_window display_update)
                            :when           (Notify )
                            :to             (main_window display_update)
                            :function_type  CallFunction
                            :arg_type       ( )
                            :action         (display_update_callback)
                            }
                        }
}
{
    :type               :button
    :name               step
    :owner              main_panel
    :help               **
    :x                  355
    :y                  15
    :width              45
    :height             19
    :constant-width     nil
    :button-type        :normal
    :foreground-color   **
    :label              "Step"
    :label-type         :string
    :initial-state      :active
    :menu               nil
    :notify-handler     step_callback
    :event-handler      nil
    :user-data          ( )
    :actions            {
                            {
                            :from           (main_window step)
                            :when           (Notify )
                            :to             (main_window step)
                            :function_type  CallFunction
                            :arg_type       ( )
                            :action         (step_callback)
                            }
                        }
}
{
    :type               :button
    :name               make_shots
    :owner              main_panel
    :help               **
    :x                  405
    :y                  15
    :width              87
    :height             19
    :constant-width     nil
    :button-type        :normal
    :foreground-color   **
    :label              "Make Shots"
    :label-type         :string
    :initial-state      :active
    :menu               nil
    :notify-handler     make_shots_callback
    :event-handler      nil
    :user-data          ( )
    :actions            {
                            {
                            :from           (main_window make_shots)
                            :when           (Notify )
                            :to             (main_window make_shots)
                            :function_type  CallFunction
                            :arg_type       ( )
                            :action         (make_shots_callback)
                            }
```

-continued

```
    }
}
{
    :type              :button
    :name              show_plan
    :owner             main_panel
    :help              **
    :x                 500
    :y                 15
    :width             82
    :height            19
    :constant-width    nil
    :button-type       :normal
    :foreground-color  **
    :label             "Show Plan"
    :label-type        :string
    :initial-state     :active
    :menu              nil
    :notify-handler    show_plan_callback
    :event-handler     nil
    :user-data         ( )
    :actions           {
                          {
                              :from           (main_window show_plan)
                              :when           (Notify )
                              :to             (main_window show_plan)
                              :function_type  CallFunction
                              :arg_type       ( )
                              :action         (show_plan_callback)
                          }
                       }
}
{
    :type              :text-field
    :name              file_name
    :owner             main_panel
    :help              **
    :x                 15
    :y                 50
    :width             199
    :height            15
    :value-x           94
    :value-y           50
    :value-length      15
    :stored-length     80
    :rows              3
    :foreground-color  **
    :text-type         :alphanumeric
    :label             "File Name:"
    :label-type        :string
    :layout-type       :horizontal
    :value-underlined  t
    :initial-value     **
    :initial-state     :active
    :read-only         nil
    :notify-handler    nil
    :event-handler     nil
    :user-data         ( )
    :actions           ( )
}
{
    :type              :text-field
    :name              display_mag
    :owner             main_panel
    :help              **
    :x                 230
    :y                 50
    :width             149
    :height            15
    :value-x           308
    :value-y           50
    :value-length      2
    :stored-length     40
    :rows              3
    :foreground-color  **
    :text-type         :numeric
    :label             "Disp. Mag:"
    :label-type        :string
    :layout-type       :horizontal
```

-continued

```
          :value-underlined    t
          :max-value           10
          :min-value           1
          :initial-value       1
          :initial-state       :active
          :read-only           nil
          :notify-handler      nil
          :event-handler       nil
          :user-data           ( )
          :actions             ( )
}
{
          :type                :text-field
          :name                load_mag
          :owner               main_panel
          :help                **
          :x                   385
          :y                   50
          :width               146
          :height              15
          :value-x             460
          :value-y             50
          :value-length        2
          :stored-length       10
          :rows                3
          :foreground-color    **
          :text-type           :numeric
          :label               "Load Mag:"
          :label-type          :string
          :layout-type         :horizontal
          :value-underlined    t
          :max-value           10
          :min-value           1
          :initial-value       1
          :initial-state       :active
          :read-only           nil
          :notify-handler      nil
          :event-handler       nil
          :user-data           ( )
          :actions             ( )
}
{
          :type                :test-field
          :name                x
          :owner               main_panel
          :help                **
          :x                   15
          :y                   75
          :width               54
          :height              15
          :value-x             33
          :value-y             75
          :value-length        4
          :stored-length       40
          :rows                3
          :foreground-color    **
          :text-type           :alphanumeric
          :label               "x:"
          :label-type          :string
          :layout-type         :horizontal
          :value-underlined    t
          :initial-value       "0"
          :initial-state       :active
          :read-only           nil
          :notify-handler      nil
          :event-handler       nil
          :user-data           ( )
          :actions             ( )
}
{
          :type                :text-field
          :name                y
          :owner               main_panel
          :help                **
          :x                   75
          :y                   75
          :width               55
          :height              15
          :value-x             94
```

```
        :value-y            75
        :value-length       4
        :stored-length      40
        :rows               3
        :foreground-color   **
        :text-type          :alphanumeric
        :label              "y:"
        :label-type         :string
        :layout-type        :horizontal
        :value-underlined   t
        :initial-value      "0"
        :initial-state      :active
        :read-only          nil
        :notify-handler     nil
        :event-handler      nil
        :user-data          ( )
        :actions            ( )
}
{
        :type               :text-field
        :name               z
        :owner              main_panel
        :help               **
        :x                  135
        :y                  75
        :width              54
        :height             15
        :value-x            153
        :value-y            75
        :value-length       4
        :stored-length      40
        :rows               3
        :foreground-color   **
        :text-type          :alphanumeric
        :label              "z:"
        :label-type         :string
        :layout-type        :horizontal
        :value-underlined   t
        :initial-value      "0"
        :initial-state      :active
        :read-only          nil
        :notify-handler     nil
        :event-handler      nil
        :user-data          ( )
        :actions            ( )
}
{
        :type               :text-field
        :name               r
        :owner              main_panel
        :help               **
        :x                  195
        :y                  75
        :width              53
        :height             15
        :value-x            212
        :value-y            75
        :value-length       4
        :stored-length      40
        :rows               3
        :foreground-color   :alphanumeric
        :label              "r:"
        :label-type         :string
        :label-type         :horizontal
        :value-underlined   t
        :initial-value      "0"
        :initial-state      :active
        :read-only          nil
        :notify-handler     nil
        :event-handler      nil
        :user-data          ( )
        :actions            ( )
}
{
        :type               :text-field
        :name               helmet
        :owner              main_panel
        :help               **
        :x                  255
```

-continued

```
            :y                  75
            :width              53
            :height             15
            :value-x            212
            :value-y            75
            :value-length       4
            :stored-length      40
            :rows               3
            :foreground-color   **
            :text-type          :alphanumeric
            :label              "r:"
            :label-type         :string
            :layout-type        :horizontal
            :initial-value      "0"
            :initial-state      :active
            :read-only          nil
            :notify-handler     nil
            :event-handler      nil
            :user-data          ( )
            :actions            ( )
}
{
            :type               :text-field
            :name               slice_number
            :owner              main_panel
            :help               **
            :x                  260
{
            :type               :text-field
            :name               slice_number
            :owner              main_panel
            :help               **
            :x                  260
            :y                  75
            :width              115
            :height             15
            :value-x            304
            :value-y            75
            :value-length       3
            :stored-length      20
            :rows               3
            :foreground-color   **
            :text-type          :numeric
            :label              "Slice:"
            :label-type         :string
            :layout-type        :horizontal
            :value-underlined   t
            :max-value          100
            :min-value          0
            :initial-value      0
            :initial-state      :active
            :read-only          nil
            :notify-handler     nil
            :event-handler      nil
            :user-data          ( )
            :actions            ( )
}
{
            :type               :text-field
            :name               overlap
            :owner              main_panel
            :help               **
            :x                  385
            :y                  75
            :width              137
            :height             15
            :value-x            451
            :value-y            75
            :value-length       2
            :stored-length      20
            :rows               3
            :foreground-color   **
            :text-type          :numeric
            :label              "Overlap:"
            :label-type         :string
            :layout-type        :horizontal
            :value-underlined   t
            :max-value          10
            :min-value          0
```

```
                :initial-value          0
                :initial-state          :active
                :read-only              nil
                :notify-handler         nil
                :event-handler          nil
                :user-data              ( )
                :actions                ( )
        }
        {
                :type                   :text-field
                :name                   gap
                :owner                  main_panel
                :help                   **
                :x                      545
                :y                      75
                :width                  108
                :height                 15
                :value-x                582
                :value-y                75
                :value-length           2
                :stored-length          20
                :rows                   3
                :foreground-color       **
                :text-type              :numeric
                :label                  "Gap:"
                :label-type             :string
                :layout-type            :horizontal
                :value-underlined       t
                :max-value              10
                :min-value              0
                :initial-value          0
                :initial-state          :active
                :read-only              nil
                :notify-handler         nil
                :event-handler          nil
                :user-data              ( )
                :actions                ( )
        }
        {
                :type                   :canvas-pane
                :name                   main_canvas
                :owner                  main_window
                :help                   **
                :x                      0
                :y                      100
                :width                  700
                :height                 700
                :background-color       **
                :foreground-color       **
                :initial-state          :visible
                :draggable              nil
                :droppable              nil
                :default-drop-site      nil
                :menu                   nil
                :horizontal-scrollbar   t
                :scrollable-width       700
                :vertical-scrollbar     t
                :scrollable-height      700
                :repaint-proc           nil
                :event-handler          nil
                :drawing-model          :xview
                :user-data              ( )
                :actions                ( )
        }
        {
                :type                   :base-window
                :name                   sub_window
                :owner                  main_window
                :width                  400
                :height                 470
                :background-color       **
                :foreground-color       **
                :label                  "3D View"
                :label-type             :string
                :initial-state          :open
                :show-footer            t
                :resizable              nil
                :icon-file              "g3dplan.icon"
                :icon-label             **
```

```
        :icon-mask-file     **
        :event-handler      nil
        :user-data          ( )
        :actions            ( )
}
{
        :type               :control-area
        :name               sub_panel
        :owner              sub_window
        :help               **
        :x                  0
        :y                  0
        :width              400
        :height             70
        :background-color   **
        :foreground-color   **
        :initial-state      :visible
        :show-border        t
        :menu               nil
        :event-handler      nil
        :user-data          ( )
        :actions            ( )
}
{
        :type               :text-field
        :name               x_rot
        :owner              sub_panel
        :help               **
        :x                  10
        :y                  15
        :width              117
        :height             15
        :value-x            56
        :value-y            15
        :value-length       3
        :stored-length      5
        :rows               3
        :foreground-color   **
        :text-type          :numeric
        :label              "X Rot:"
        :label-type         :string
        :layout-type        :horizontal
        :value-underlined   t
        :max-value          360
        :min-value          0
        :initial-value      0
        :initial-state      :active
        :read-only          nil
        :notify-handler     nil
        :event-handler      nil
        :user-data          ( )
        :actions            ( )
}
{
        :type               :text-field
        :name               y_rot
        :owner              sub_panel
        :help               **
        :x                  145
        :y                  15
        :width              117
        :height             15
        :value-x            191
        :value-y            15
        :value-length       3
        :stored-length      5
        :rows               3
        :foreground         **
        :text-type          :numeric
        :label              "Y Rot:"
        :label-type         :string
        :layout-type        :horizontal
        :value-underlined   t
        :max-value          360
        :min-value          0
        :initial-value      0
        :initial-state      :active
        :read-only          nil
        :notify-handler     nil
```

-continued

```
        :event-handler      nil
        :user-data           ( )
        :actions             ( )
}
{
        :type                :text-field
        :name                z_rot
        :owner               sub_panel
        :help                **
        :x                   275
        :y                   15
        :width               116
        :height              15
        :value-x             320
        :value-y             15
        :value-length        3
        :stored-length       5
        :rows                3
        :foreground-color    **
        :text-type           :numeric
        :label               "Z Rot:"
        :label-type          :string
        :layout-type         :horizontal
        :value-underlined    t
        :max-value           360
        :min-value           0
        :initial-value       0
        :initial-state       :active
        :read-only           nil
        :notify-handler      nil
        :event-handler       nil
        :user-data           ( )
        :actions             ( )
}
{
        :type                :button
        :name                display_3d
        :owner               sub_panel
        :help                **
        :x                   168
        :y                   40
        :width               63
        :height              19
        :constant-width      nil
        :button-type         :normal
        :foreground-color    **
        :label               "Display"
        :label-type          :string
        :initial-state       :active
        :menu                nil
        :notify-handler      display_3d_callback
        :event-handler       nil
        :user-data           ( )
        :actions             {
            {
            :from            (sub_window display_3d)
            :when            (Notify )
            :to              (sub_window display_3d)
            :function_type   CallFunction
            :arg_type        ( )
            :action          (display_3d_callback)
            }
        }
}
{
        :type                :canvas-pane
        :name                sub_canvas
        :owner               sub_window
        :help                **
        :x                   0
        :y                   70
        :width               400
        :height              400
        :background-color    **
        :foreground-color    **
        :initial-state       :visible
        :draggable           nil
        :droppable           nil
        :default-drop-site   nil
```

-continued

```
            :menu                   nil
            :horizontal-scrollbar   t
            :scrollable-width       400
            :vertical-scrollbar     t
            :scrollable-height      400
            :repaint-proc           nil
            :event-handler          nil
            :drawing-model          :xview
            :user-data              ( )
            :actions                ( )
    }
  }
}
/*
 * globals.c - globals variables and functions to read/write them
 */
#include "includes.h"
#include "g3dplan_ui.h"
#include "g3dplan.h"
/*
 * Global object definitions.
 */
static g3dplan_main_window_objects *G3dplan_main_window =
NULL;
static g3dplan_sub_window_objects *G3dplan_sub_window = NULL;
static g3dplan_window_array_objects window_array;
/*
 * Global object definitions.
 */
static char *prog_name = NULL;
/* X display variables */
static Visual          *visual = NULL;
static Display         *display = NULL;
static Colormap        cmap;
static Window          paint_window, sub_paint_window;
static GC              gc, sub_gc;
static unsigned long black_pixel, white_pixel, red_pixel, yellow_pixel,
green_pixel;
static unsigned long blue_pixel, brown_pixel, orange_pixel;
static unsigned long gray_start_pixel;
static int             canvas_width, canvas_height, sub_canvas_width,
sub_canvas_height;
static int             depth;
static int             current_slice;
/*
 * Instance XV_KEY_DATA key. An instance is a set of related
 * user interface objects. A pointer to an object's instance
 * is stored under this key in every object. This must be a
 * global variable.
 */
Attr_attribute INSTANCE;
/*
 * more global variables
 */
static CONTOUR contour;
static SKELETON *first_skelet = NULL, *tmp_skelet = NULL;
static unsigned char   *img = NULL;
static unsigned char   *tmp_img = NULL;
static int   img_width, img_height,img_depth; /* of the image */
static int   load_mag;
static int   stage = 2;
static int   img_min = 0, img_max = 0;
static unsigned short *dist_img;
static float vmin=0.0, vmax=0.0, umin=0.0, umax=0.0;
static int destroy_override = FALSE;
/*
 * global variable operating functions
 */
void init_contour( )
{
    contour.num_slices = 0;
    contour.min_x = contour.min_y = contour.min_z =
    contour.max_x = contour.max_y = contour.max_z = 0.0;
    contour.x = contour.y = NULL;
    contour.z = NULL;
    contour.num_vert = NULL;
}
void set_contour(CONTOUR c)
{
    contour.num_slices = c.num_slices;
```

```
            contour.num_vert = c.num_vert;
            contour.min_x = c.min_x;
            contour.min_y = c.min_y;
            contour.min_z = c.min_z;
            contour.max_x = c.max_x;
            contour.max_y = c.max_y;
            contour.max_z = c.max_z;
            contour.x = c.x;
            contour.y = c.y;
            contour.z = c.z;
    }
    unsigned char *get_img( )
    {
            return img;
    }
    void set_img(unsigned char *imptr)
    {
            img = imptr;
    }
    unsigned char *get_tmp_img( )
    {
            return tmp_img;
    }
    void set_tmp_img(unsigned char *imptr)
    {
            tmp_img = imptr;
    }
    unsigned short *get_dist_img( )
    {
            return dist_img;
    }
    void set_dist_img(unsigned short *dptr)
    {
            dist_img = dptr;
    }
    CONTOUR get_contour( )
    {
            return contour;
    }
    SKELETON *get_first_skelet( )
    {
            return first_skelet;
    }
    void set_first_skelet(SKELETON *sptr)
    {
            first_skelet = sptr;
    }
    SKELETON *get_tmp_skelet( )
    {
            return tmp_skelet( );
    }
    void set_tmp_skelet(SKELETON *sptr)
    {
            tmp_skelet = sptr;
    }
    void FreeContour( )
    {
            int i;
            extern void GFree( );
            extern void init_contour( );
            GFree(contour.z);
            GFree(contour.num_vert);
            if(contour.x != NULL)
            {
                    for (i= 0;i<contour.num_slices;i++)
                    {
                            if(contour.x[i] != NULL)
                                    GFree(contour.x[i]);
                    }
                    GFree(contour.x);
            }
            if(contour.y != NULL)
            {
                    for(i=0;i<contour.num_slices;i++)
                    {
                            if(contour.y[i] != NULL)
                                    GFree(contour.y[i]);
                    }
                    GFree(contour.y);
```

-continued

```
        }
        init_contour( );
}
void set_prog_name(char *name)
{
        prog_name = name;
}
char *get_prog_name( )
{
        return prog_name;
}
void set_main_window_objects(g3dplan_main_window_objects *obj)
{
        G3dplan_main_window = obj;
}
void set_sub_window_objects(g3dplan_sub_window_objects *obj)
{
        G3dplan_sub_window = obj;
}
g3dplan_main_window_objects *get_main_window_objects( )
{
        return G3dplan_main_window;
}
g3dplan_sub_window_objects *get_sub_window_objects( )
{
        return G3dplan_sub_window;
}
Display *get_display( )
{
        return display;
}
void set_display(Display *d)
{
        display = d;
}
int get_load_mag( )
{
        return load_mag;
}
void set_load_mag(int lmag)
{
        load_mag = lmag;
}
int get_img_width( )
{
        return img_width;
}
void set_img_width(int width)
{
        img_width = width;
}
int get_img_height( )
{
        return img_height;
}
void set_img_height(int height)
{
        img_height = height;
}
int get_img_depth( )
{
        return img_depth;
}
void set_img_depth(int depth)
{
        img_depth = depth;
}
int get_stage( )
{
        return stage;
}
void set_stage(int s)
{
        stage = s;
}
Visual *get_visual( )
{
        return visual;
}
```

-continued

```
void set_visual(Visual *v)
{
    visual = v;
}
Colormap get_colormap( )
{
    return cmap;
}
void set_colormap(Colormap c)
{
    cmap = c ;
}
Window get_paint_window( )
{
    return paint_window;
}
void set_paint_window(Window w)
{
    paint_window = w;
}
Window get_sub_paint_window( )
{
    return sub_paint_window;
}
void set_sub_paint_window(window w)
{
    sub_paint_window = w;
}
GC get_gc( )
{
    return gc;
}
void set_gc(GC g)
{
    gc = g;
}
GC get_sub_gc( )
{
    return sub_gc;
}
void set_sub_gc(GC g)
{
    sub_gc = g;
}
unsigned long get_black_pixel( )
{
    return_black_pixel;
}
void set_black_pixel(unsigned long p)
{
    black_pixel = p;
}
unsigned long get_white_pixel( )
{
    return white_pixel;
}
void set_white_pixel(unsigned long p)
{
    white_pixel = p;
}
unsigned long get_green_pixel( )
{
    return green_pixel;
}
void set_green_pixel(unsigned long p)
{
    green_pixel = p;
}
unsigned long get_red_pixel( )
{
    return red_pixel;
}
void set_red_pixel(unsigned long p)
{
    red_pixel = p;
}
unsigned long get_yellow_pixel( )
{
    return yellow_pixel;
```

-continued

```
}
void set_yellow_pixel(unsigned long p)
{
    yellow_pixel = p;
}
unsigned long get_blue_pixel( )
{
    return blue_pixel;
}
void set_blue_pixel(unsigned long p)
{
    blue_pixel = p;
}
unsigned long get_brown_pixel( )
{
    return brown_pixel;
}
void set_brown_pixel(unsigned long p)
{
    brown_pixel = p;
}
unsigned long get_orange_pixel( )
{
    return orange_pixel;
}
void set_orange_pixel(unsigned long p)
{
    orange_pixel = p;
}
unsigned long get_gray_start_pixel( )
{
    return gray_start_pixel;
}
void set_gray_start_pixel(unsigned long p)
{
    gray_start_pixel = p;
}
int get_canvas_width( )
{
    return canvas_width;
}
void set_canvas_width(int w)
{
    canvas_width = w;
}
int get_canvas_height( )
{
    return canvas_height;
}
void set_canvas_height(int h)
{
    canvas_height = h;
}
int get_sub_canvas_width( )
{
    return sub_canvas_width;
}
void set_sub_canvas_width(int w)
{
    sub_canvas_width = w;
}
int get_sub_canvas_height( )
{
    return sub_canvas_height;
}
void set_sub_canvas_height(int h)
{
    sub_canvas_height = h;
}
int get_depth( )
{
    return depth;
}
void set_depth(int d)
{
    depth = d;
}
void print_contour( )
{
```

```
        int i,j;
        printf("contour: Num of Slices: %d\n", contour.num_slices);
        if(contour.num_slices > 0)
        {
            printf("    Min X: %g\n", contour.min_x);
            printf("    Min Y: %g\n", contour.min_y);
            printf("    Min Z: %g\n", contour.min_z);
            printf("    Max X: %g\n", contour.max_x);
            printf("    Max Y: %g\n", contour.max_y);
            printf("    Max Z: %g\n", contour.max_z);
            for(i=0;i<contour.num_slices;i++)
            {
                printf("    Slice %d Number of Vertices
                %d\n", i, contour.num_vert[i]);
                printf("        Z: %g\n",
                contour.z[i]);
                for(j=0;j<contour.num_vert[i];j++)
                {
                    printf("            %d: (X: %g,
                    Y: %g)\n", j,
                        contour.x[i][j],
                        contour.y[i][j]);
                }
            }
        }
        else
        {
            printf("    Empty contour\n");
        }
}
int get_current_slice( )
{
    return current_slice;
}
void set_current_slice(int n)
{
    current_slice = n;
}
void print_1contour(CONTOUR c)
{
        int i,j;
        printf("contour: Num of Slices: %d\n", c.num_slices);
        if(c.num_slices > 0)
        {
            printf("    Min X: %g\n", c.min_x);
            printf("    Min Y: %g\n", c.min_y);
            printf("    Min Z: %g\n", c.min_z);
            printf("    Max X: %g\n", c.max_x);
            printf("    Max Y: %g\n", c.max_y);
            printf("    Max Z: %g\n", c.max_z);
            for(i=0;i<c.num_slices;i++)
            {
                printf("    Slice %d Number of Vertices
                %d\n", i, c.num_vert[i]);
                printf("        Z: %g\n", c.z[i]);
                for(j=0;j<c.num_vert[i];j++)
                {
                    printf("            %d: (X: %g,
                    Y: %g)\n", j,
                        c.x[i][j], c.y[i][j]);
                }
            }
        }
        else
        {
            printf("    Empty contour\n");
        }
}
void print_dimensions( )
{
    printf("dimensions: img width: %d height: %d depth: %d\n",
        img_width, img_height, img_depth);
}
void set_img_min(int v)
{
    img_min = v;
}
void set_img_max(int v)
{
```

-continued

```
        img_max = v;
}
int get_img_min( )
{
        return img_min;
}
int get_img_max( )
{
        return img_max;
}
void set_view_vmin(float v)
{
        vmin = v;
}
void set_view_umin(float v)
{
        umin = v;
}
void set_view_vmax(float v)
{
        vmax = v;
}
void set_view_umax(float v)
{
        umax = v;
}
float get_view_vmin( )
{
        return vmin ;
}
float get_view_umin( )
{
        return umin ;
}
float get_view_vmax( )
{
        return vmax ;
}
float get_view_umax( )
{
        return umax ;
}
int get_destroy_override( )
{
        return destroy_override;
}
void set_destroy_override(int t)
{
        destroy_override = t;
}
g3dplan_window_array_objects  *get_window_array_pointer( )
{
        return (g3dplan_window_array_objects *)(&(window_array));
}
void init_window_array( )
{
        window_array.window = NULL;
        window_array.canvas = NULL;
        window_array.paint_window = NULL;
        window_array.count = 0;
}
void free_window_array( )
{
        int i;
        void GFree( );
        if(window_array.count < 1)
                return;
        GFree(window_array.paint_window);
        for(i=0;i<window_array.count;i++)
        {
                set_destroy_override(TRUE);
                xv_destroy_safe(window_array.window[i]);
        }
        GFree(window_array.canvas);
        GFree(window_array.window);
        window_array.window         = NULL;
        window_array.canvas         = NULL;
        window_array.paint_window   = NULL;
        window_array.count          = 0;
```

```c
}
#include <stdio.h>
#include <math.h>
#include <malloc.h>
#include <sys/param.h>
#include <sys/types.h>
#include <sys/time.h>
#include <string.h>
#if defined(__STDC__)
#include <stdarg.h>
#else
#include <varargs.h>
#endif
#include <values.h>
#include <xview/xview.h>
#include <xview/frame.h>
#include <xview/panel.h>
#include <xview/canvas.h>
#include <xview/scrollbar.h>
#include <xview/notice.h>
#include <xview/cursor.h>
#include <xview/textsw.h>
#include <xview/xv_xrect.h>
#include <X11/X.h>
#include <X11/Xlib.h>
#include <X11/Xutil.h>
#include <X11/Xos.h>
#include <X11/cursorfont.h>
/*
 * processing routines for g3dplan:
 * load_contour.c
 *
 * button callback routines
 *
 */
#include "includes.h"
#include "g3dplan_ui.h"
#include "g3dplan_h"
/*
 * esternal functions
 */
extern void display_status( );
extern void  free_list( ), GFree( );
extern g3dplan_main_window_objects *get_main_window_objects( );
extern Display *get_display( );
extern char *get_prog_name( );
extern SKELETON *get_first_skelet( );
extern unsigned char *get_img( );
extern unsigned short *get_dist_img( );
extern int get_load_mag( );
extern int get_img_width( ), get_img_height( ), get_img_depth( );
extern void set_first_skelet(SKELETON *);
extern void set_img(unsigned char *);
extern void set_dist_img(unsigned short *);
extern void get_load_mag(int);
extern void set_contour(CONTOUR);
extern void set_current_slice(int);
extern void FreeContour( );
extern void print_contour( );
void
load_contour( )
{
    int    i, j;
    float  max_x, max_y, max_z;
    char sbuff[256];
    char   *input = NULL;
    FILE   *fp = NULL;
    g3dplan_main_window_objects  *G3dplan_main_window =
    get_main_window_objects( );
    Display *display = get_display( );
    char *prog_name = get_prog_name( );
    SKELETON *first_skelet = get_first_skelet( );
    unsigned short *dist_img = get_dist_img( );
    unsigned char   *img = get_img( );
    int load_mag = get_load_mag( );
    int img_width = get_img_width( ),
    img_height = get_img_height( ),
    img_depth = get_img_depth( );
    CONTOUR contour;
```

-continued

```
/*
 * get the file name
 */
input = (char *)xv_get(G3dplan_main_window->file_name,
PANEL_VALUE);
if((int) strlen(input) < (int)1)
{
    sprintf(sbuff, "%s: specify a file name for the contour
    data\n", prog_name);
    xv_set(G3dplan_main_window->main_window,
    FRAME_LEFT_FOOTER, sbuff, NULL);
    XBell(display, 0);
    return ;
}
/*
 * free up previous contour, image data and skeleton data
 */
FreeContour( );
GFree(img);
img = NULL;
set_img(NULL);
free_list(first_skelet);
first_skelet = NULL;
set_first_skelet(NULL);
GFree(dist_img);
dist_img = NULL;
set_dist_img(NULL);
/*
 * read the contour file
 */
if ((fp = fopen(input, "r")) == NULL)
{
    sprintf(sbuff, "%s: can not open file %s to read \n",
    prog_name, input);
    xv_set(G3dplan_main_window->main_window,
    FRAME_LEFT_FOOTER, sbuff, NULL);
    XBell(display, 0);
    return ;
}
if ((fscanf(fp,"%g",&(contour.min_x))) != 1)
{
    sprintf(sbuff, " %s: read file %s error\n",prog_name,
    input);
    fclose(fp);
    xv_set(G3dplan_main_window->main_window,
    FRAME_LEFT_FOOTER, sbuff, NULL);
    XBell(display, 0);
    return ;
}
if ((fscanf(fp, "%g",&(contour.min_y))) != 1)
{
    sprintf(sbuff, " %s: read file %s error\n", prog_name,
    input);
    fclose(fp);
    xv_set(G3dplan_main_window->main_window,
    FRAME_LEFT_FOOTER, sbuff, NULL);
    XBell(display, 0);
    return ;
}
if (fscanf(fp,"%g",&(contour.min_z))) != 1)
{
    sprintf(sbuff, " %s: read file %s error\n", prog_name,
    input);
    fclose(fp);
    xv_set(G3dplan_main_window->main_window,
    FRAME_LEFT_FOOTER, sbuff, NULL);
    XBell(display, 0);
    return ;
}
if ((fscanf(fp,"%g",&(contour.max_x))) != 1)
{
    sprintf(sbuff, " %s: read file %s error\n", prog_name,
    input);
    fclose(fp);
    xv_set(G3dplan_main_window->main_window,
    FRAME_LEFT_FOOTER, sbuff, NULL);
    XBell(display, 0);
    return ;
}
```

-continued

```
if ((fscanf(fp,"%g",&(contour.max_y))) != 1)
{
    sprinft(sbuff, " %s: read file %s error\n", prog_name,
    input);
    fclose(fp);
    xv_set(G3dplan_main_window->main_window,
    FRAME_LEFT_FOOTER, sbuff, NULL);
    XBell(display, 0);
    return ;
}
if ((fscanf(fp,"%g",&(contour.max_z))) != 1)
{
    sprintf(sbuff, " %s: read file %s error\n", prog_name,
    input);
    fclose(fp);
    xv_set(G3dplan_main_window->main_window,
    FRAME_LEFT_FOOTER, sbuff, NULL);
    XBell(display, 0);
    return ;
}
if ((fscanf(fp,"%d",%(contour.num_slices))) != 1)
{
    sprintf(sbuff, " %s: read file %s error\n",
    prog_name,input);
    fclose(fp);
    xv_set(G3dplan_main_window->main_window,
    FRAME_LEFT_FOOTER, sbuff, NULL);
    XBell(display, 0);
    return ;
}
contour.num_vert = (int *) calloc(contour.num_slices,
sizeof(int));
if(contour.num_vert == NULL)
{
    sprintf(sbuff, " %s: read file %s error\n",
    prog_name,input);
    fclose(fp);
    xv_set(G3dplan_main_window->main_window,
    FRAME_LEFT_FOOTER, sbuff, NULL);
    XBell(display, 0);
    return ;
}
for (i=0;i < contour.num_slices; i ++)
{
    if ((fscanf(fp,"%d",&(contour.num_vert[i]))) != 1)
    {
        GFree(contour.num_vert);
        sprintf(sbuff, " %s: read file %s error\n",
        prog_name,input);
        fclose(fp);
        xv_set(G3dplan_main_window->main_window,
        FRAME_LEFT_FOOTER, sbuff, NULL);
        XBell(display, 0);
        return ;
    }
}
load_mag = (int) xv_get(G3dplan_main_window->load_mag,
PANEL_VALUE);
set_load_mag(load_mag);
/* allocate memory for contour */
contour.z = (float *) calloc(contour.num_slices,
sizeof(float));
if(contour.z == NULL)
{
    GFree(contour.num_vert);
    sprintf(sbuff, " %s: can not allocate memory for
    contour points %s\n", prog_name, input);
    fclose(fp);
    xv_set(G3dplan_main_window->main_window,
    FRAME_LEFT_FOOTER, sbuff, NULL);
    XBell(display, 0);
    return;
}
contour.x = (float **) calloc(contour.num_slices, sizeof(float
*));
contour.y = (float **) calloc(contour.num_slices, sizeof(float
*));
if(contour.x == NULL || contour.y == NULL)
{
```

```
        GFree(contour.num_vert);
        GFree(contour.z);
        GFree(contour.x);
        GFree(contour.y);
        sprintf(sbuff, " %s: can not allocate memory for
        contour points %s\n", prog_name, input);
        fclose(fp);
        xv_set(G3dplan_main_window->main_window,
        FRAME_LEFT_FOOTER, sbuff, NULL);
        XBell(display, 0);
        return;
}
for(i=0;i<contour.num_slices;i++)
{
    contour.x[i] = (float *) calloc(contour.num_vert[i],
    sizeof(float));
    contour.y[i] = (float *) calloc(contour.num_vert[i],
    sizeof(float));
    if(contour.x[i] == NULL || contour.y[i] == NULL)
    {
        GFree(contour.num_vert);
        GFree(contour.z);
        GFree(contour.x);
        GFree(contour.y);
        for(j=0;j<i;j++)
        {
            GFree(contour.x[j]);
            GFree(contour.y[j]);
        }
        sprintf(sbuff, " %s: can not allocate memory
        for contour points %s\n", prog_name, input);
        fclose(fp);
        xv_set(G3dplan_main_window->main_window,
        FRAME_LEFT_FOOTER, sbuff, NULL);
        XBell(display, 0);
        return;
    }
}
for(i=0;i<contour.num_slices;i++)
{
    if ((fscanf(fp, "%g",&(contour.z[i]))) != 1)
    {
        GFree(contour.num_vert);
        GFree(contour.z);
        GFree(contour.x);
        GFree(contour.y);
        for(j=0;j<contour.num_slices;j++)
        {
            GFree(contour.x[j]);
            GFree(contour.y[j]);
        }
        sprintf(sbuff, " %s: read file %s error\n",
        prog_name, input);
        fclose(fp);
        xv_set(G3dplan_main_window->main_window,
        FRAME_LEFT_FOOTER, sbuff, NULL);
        XBell(display, 0);
    }
    for(j=0;j< contour.num_vert[i];j++)
    {
        if((fscan(fp,"%g", &(contour.x[i][j]))) != 1 )
        {
            GFree(contour.num_vert);
            GFree(contour.z);
            GFree(contour.x);
            GFree(contour.y);
            for(j=0;j<contour.num_slices;j++)
            {
                GFree(contour.x[j]);
                GFree(contour.y[j]);
            }
            sprintf(sbuff, " %s: read file %s
            error\n", prog_name, input);
            fclose(fp);
            xv_set(G3dplan_main_window->main_window,
            FRAME_LEFT_FOOTER, sbuff, NULL);
            XBell(display, 0);
            return ;
        }
```

```
        if((fscanf(fp, "%g", &(contour.y[i][j]))) != 1 )
        {
            GFree(contour.num_vert);
            GFree(contour.z);
            GFree(contour.x);
            GFree(contour.y);
            for(j=0;j<contour.num_slices;j++)
            {
                GFree(contour.x[j]);
                GFree(contour.y[j]);
            }
            sprintf(sbuff, " %s: read file %s
            error\n", prog_name, input);
            fclose(fp);
            xv_set(G3dplan_main_window->main_window,
            FRAME_LEFT_FOOTER, sbuff, NULL);
            XBell(display, 0);
            return ;
        }
    }
}
fclose(fp);
/*
 * rescale the contour information
 */
for(i=0;i<contour.num_slices;i++)
{
    contour.z[i] = load_mag*(contour.z[i] - contour.min_z)
    + contour.min_z;
    for(j=0;j < contour.num_vert[i];j++)
    {
        contour.x[i][j] = load_mag*(contour.x[i][j] -
        contour.min_x) + contour.min_x;
        /*
        contour.y[i][j] = load_mag*(contour.y[i][j] -
        contour.min_y] + contour.min_y;
        */
        contour.y[i][j] = load_mag*(contour.y[i][j] -
        contour.min_y)*1.1 + contour.min_y;
    }
}
/*
 * reset the min/max of the contour
 */
max_x = (contour.max_x - contour.min_x)* load_mag +
contour.min_x;
max_y = (contour.max_y - contour.min_y)* load_mag *1.1 +
contour.min_y;
/*
max_y = (contour.max_y - contour.min_y)* load_mag +
contour.min_y;
*/
max_z = (contour.max_z - contour.min_z)* load_mag +
contour.min_z;
contour.max_y = max_y;
contour.max_x = max_x;
contour.max_z = max_z;
img_width = (int)(contour.max_x - contour.min_x) ;
img_height = (int)(contour.max_y - contour.min_y) ;
img_depth = (int)(contour.max_z - contour.min_z) ;
if(img_width > (float)MAX_IMG_SIZE || img_height >
(float)MAX_IMG_SIZE || img_depth > (float)MAX_IMG_SIZE)
{
    GFree(contour.num_vert);
    GFree(contour.z);
    GFree(contour.x);
    GFree(contour.y);
    for(j=0;j<contour.num_slices;j++)
    {
        GFree(contour.x[j]);
        GFree(contour.y[j]);
    }
    sprintf(sbuff,"%s: the contour is outside the max. size
    of the image allowed",prog_name);
    xv_set(G3dplan_main_window->main_window,
    FRAME_LEFT_FOOTER, sbuff, NULL);
    XBell(display, 0);
    return ;
}
```

```
    set_img_width(img_width);
    set_img_height(img_height);
    set_img_depth(img_depth);
    /*
     * set the global contour information
     */
    set_contour(contour);
    /* print_contour( ); */
    /*
     * set window object parameters
     */
    xv_set(G3dplan_main_window->slice_number,
        PANEL_MIN_VALUE, 0,
        PANEL_MAX_VALUE, (img_depth -1),
        PANEL_VALUE, 0,
        NULL);
    set_current_slice(0);
    XFlush(display);
    /*
     * display contour
     */
    display_status(DISPLAY_NONE);
    return;
}
/*
 * title: mag3D - unsigned char magnify with replication
 *
 * descr: Magnifies a 3D unsigned char array (unsigned chars) by
replication.
 *
 * usage: nunsigned char = bmag(input,ncol,nrow,nlev,output,mx,my,mz)
 *
 * value: int nunsigned char . . . number of output unsigned chars
generated
 *
 * parms:   unsigned char *input    array of input data
 *          int ncol                horizontal dimension
 *          int nrow                vertical dimension
 *          int nlev                depth dimension
 *          unsigned char *output   array to receive output data
 *          int mx                  horizontal magnification factor
 *          int my                  vertical magnification factor
 *          int mz                  depth magnification factor
 *
 */
#include <stdio.h>
#include <memory.h>
int mag3D(unsigned char *input, int ncol, int nrow, int nlev,
                    unsigned char *output, int mx, int my, int mz)
{
    int row=0, col=0, lev=0, rent=0, ccnt=0, lcnt=0, count=0;
    int xcnt, ycnt, zcnt, xinc, yinc, zinc;
    int slice_size, row_size;
    unsigned char *psl, *prow, *p, *pouptut;
    if (input==(unsigned char *)NULL || output==
    (unsigned char *)NULL || mx==0 || my==0 || mz==0)
                    return(0);
    if (abs(mx)==1 && abs(my)==1 && abs(mz)==1)
    {
        count = ncol"nrow"nlev;
        memcpy(output, input, count);
        return(count);
    }
    if (mx < 0)
            (xcnt = 1; xinc = -mx;)
    else
            (xcnt = mx; xinc = 1;)
    if (my < 0)
            (ycnt = 1; yinc = -my;)
    else
            (ycnt = my; yinc = 1;)
    if (mz < 0)
            (zcnt = 1; zinc = -mz;)
    else
            (zcnt = mz; zinc = 1;)
    row_size = yinc*ncol;
    slice_size = zinc*ncol*nrow;
    pouptut = output;
    lev = lcnt = 0;
```

```
    psl = input;
    while (lev < nlev)
    {
    row = rent = 0;
    prow = psl;
    while (row < nrow)
    {
        p = prow;
        col = ccnt = 0;
        while (col < ncol)
        {
            *poutput = *(ip + col);
            poutput++;
            count++;
            ccnt++;
            if (ccnt == xcnt)
            {
                ccnt = 0; col += xinc;
            }
        }
        rcnt++;
        if (rcnt == ycnt)
        {
            rcnt = 0;
            row += yinc;
            prow += row_size;
        }
    }
    lcnt++
    if (lcnt == zcnt)
    {
        lcnt = 0;
        lev += zinc;
        psl += slice_size;
    }
    }
    return(count);
}
/*
 *
 */
#include <stdio.h>
#include <math.h>
#include <malloc.h>
#include <sys/param.h>
#include <sys/types.h>
#include <sys/time.h>
#include <string.h>
#if (defined(__STDC__))
#include <stdarg.h>
#else
#include <varargs.h>
#endif
#include <values.h>
#include "g3dplan.h"
main(argc,argv)
int argc;
char *argv( );
{
    int     i, j, count;
    float   maxx, maxy, maxz, minx, miny, minz;
    float   xm, ym, zm;
    char sbuff[256];
    char    *input = NULL;
    char *output = NULL;
    FILE   *fp = NULL;
    CONTOUR contour;
    /*
     * get the file name
     */
    if(argc != 13)
    {
        fprintf(stderr,"%s: Usage: %s input output count maxx
        maxy maxz minx miny minz xm ym zm\n", argv[0]);
        argv[0]);
        exit[1];
    }
    input = argv[1];
    output = argv[2];
```

```
count = atoi(argv[3]);
maxx = atof(argv[4]);
maxy = atof(argv[5]);
maxz = atof(argv[6]);
minx = atof(argv[7]);
miny = atof(argv[8]);
minz = atof(argv[9]);
xm = atof(argv[10]);
ym = atof(argv[11]);
zm = atof(argv[12]);
/*
 * read the contour slices
 */
/* allocate memory for contour */
contour.num_slices = count;
contour.z = (float *) calloc(contour.num_slices,
sizeof(float));
if(contour.z == NULL)
{
    fprintf(stderr, " %s: can not allocate memory for
    contour points \n", argv[0]);
    exit[1];
}
contour.x = (float **) calloc(contour.num_slices, sizeof(float
*));
contour.y= (float **) calloc(contour.num_slices, sizeof(float
*));
if(contour.x == NULL || contour.y == NULL)
{
    fprintf(stderr, " %s: can not allocate memory for
    contour points \n", argv[0]);
    exit[1];
}
contour.num_vert = (int *) calloc(contour.num_slices,
sizeof(int));
if(contour.num_vert == NULL)
{
    fprintf(stderr, " %s: can not allocate memory for
    contour points \n", argv[0]);
    exit[1];
}
contour.z = (float *) calloc(contour.num_slices,
sizeof(float));
if(contour.z == NULL)
{
    printf(stderr, " %s: can not allocate memory for
    contour points \n", argv[0]);
    exit[1];
}
for(i=0;i<contour.num_slices;i++)
{
    contour.z[i] = i;
    if(i >=9 )
        sprintf(sbuff, "%s%d", input, (i+1));
    else
        sprintf(sbuff, "%s0%d", input, (i+1));
    if((fp = fopen(sbuff,"r")) == NULL)
    {
        fprintf(stderr, " s: can not open file %s\n",
        argv[0], sbuff);
        exit[1];
    }
    if ((fscanf(fp,"%d",&(contour.num_vert[i]))) != 1)
    {
        fprintf(stderr, " %s: read file %s error for
        number of vertices\n", argv[0], sbuff);
        fclose(fp);
        exit[1] ;
    }
    contour.x[i] = (float *) calloc(contour.num_vert[i],
    sizeof(float));
    contour.y[i] = (float *) calloc(contour.num_vert[i],
    sizeof(float));
    if(contour.x[i] == NULL || contour.y[i] == NULL)
    {
        fprintf(stderr, " %s: can not allocate memory
        for contour points for slices %s\n",
                argv[0], sbuff);
        fclose(fp);
```

```
                exit[1];
        }
    for(j=0;j< contour.num_vert[i];j++)
    {
        if((fscanf(fp,"%g", &(contour.x[i][j])) != 1 )
        {
            fprintf(stderr, " %s: read file %s
            error for vertex coordinates\n",
                argv[0], sbuff);
            fclose(fp);
            exit[1] ;
        }
        if((fscanf(fp,"%g", &(contour.y[i][j])) != 1 )
        {
            fprintf(stderr, " %s: read file %s
            error for vertex coordinates\n",
                argv[0], sbuff);
            fclose(fp);
            exit[1] ;
        }
        if( i == 0 && j == 0)
        {
            contour.min_x = contour.x[i][j];
            contour.min_y = contour.y[i][j];
            contour.max_x = contour.x[i][j];
            contour.max_y = contour.y[i][j];
            contour.min_z = contour.z[i];
            contour.max_z = contour.z[i];
        }
        else
        {
            if(contour.x[i][j] < contour.min_x)
                contour.min_z =
                contour.x[i][j];
            if(contour.y[i][j] < contour.min_y)
                contour.min_y =
                contour.y[i][j];
            if(contour.z[i] < contour.min_z)
                contour.min_z = contour.z[i];
            if(contour.x[i][j] > contour.max_x)
                contour.max_x =
                contour.x[i][j];
            if(contour.y[i][j] > contour.max_y)
                contour.max_y =
                contour.y[i][j];
            if(contour.z[i] > contour.max_z)
                contour.max_z = contour.z[i];
        }
    }
    fclose(fp);
}
/*
 * rescale the contour information
 */
for(i=0;i<contour.num_slices;i++)
{
    contour.z[i] = (maxz-minz)*(contour.z[i] -
    contour.min_z)/(contour.max_z - contour.min_z) + minz +
    zm;
    for(j=0;j < contour.num_vert[i];j++)
    {
        contour.x[i][j] = minx + xm +
            (maxx-minx)*(contour.x[i][j] -
            contour.min_x)/(contour.max_x -
            contour.min_x);
        contour.y[i][j] = miny + ym +
            (maxy-miny)*(contour.y[i][j] -
            contour.min_y)/(contour.max_y -
            contour.min_y);
    }
}
contour.min_x = minx;
contour.min_y = miny;
contour.min_z = minz;
contour.max_x = maxx+2*xm;
contour.max_y = maxy+2*ym;
contour.max_z = maxz+2*zm;
/*
 * write the contour file
```

```
        */
        if ((fp = fopen(output,"w")) == NULL)
        {
            fprintf(stderr, " %s: can not open file%s\n", argv[0],
            output);
            exit[1];
        }
        fprintf(fp,"%g\n",(contour.min_x));
        fprintf(fp,"%g\n",(contour.min_y));
        fprintf(fp,"%g\n",(contour.min_z));
        fprintf(fp,"%g\n",(contour.max_x));
        fprintf(fp,"%g\n",(contour.max_y));
        fprintf(fp,"%g\n",(contour.max_z));
        fprintf(fp, "%d\n\n",(contour.num_slices));
        for (i=0;i < contour.num_slices; i ++)
        {
            fprintf(fp,"d\n",(contour.num_vert[i]));
        }
        fprintf(fp,"\n");
        for(i=0;i<contour.num_slices;i++)
        {
            fprintf(fp,"%g\n",(contour.z[i]));
            for(j=0;j< contour.num_vert[i];j++)
            {
                fprintf(fp," %g", (contour.x[i][j]));
                fprintf(fp," %g", (contour.y[i][j]));
                if(((j+1) % 5) == 0)
                    fprintf(fp,"\n");
            }
            fprintf(fp,"\n");
        }
        fclose(fp);
        for(i=0;i<contour.num_slices;i++)
        {
            sprintf(sbuff,"%s_mat_%d", output,(i+1));
            if ((fp = fopen(sbuff,"w")) == NULL)
            {
                fprintf(stderr, " %s: can not open file%s\n",
                argv[0], sbuff);
                exit[1];
            }
            for(j=0;j< contour.num_vert[i];j++)
            {
                fprint(fp," %g", (contour.x[i][j]));
                fprintf(fp," %g", (contour.y[i][j]));
                fprintf(fp," %g\n",(contour.z[i]));
            }
            fclose(fp);
        }
    exit(0);
}
/*
 * button callback routines: make_shots form already know plan
 *
 */
#include "includes.h"
#include "g3dplan_ui.h"
#include "g3dplan_h"
/*
 * Global object definitions
 */
extern g3dplan_main_window_objects * get_main_window_objects( );
extern void display_status( ), GFree( );
extern int mag3D( );
extern int cutimg( );
extern SKELETON *add_note( );
extern SKELETON *get_first_skelet( );
extern void  set_first_skelet(SKELETON *);
extern unsigned char *get_img( );
extern unsigned shor *get_dist_img( );
void
make_shots( )
{
    SKELETON *first_skelet = get_first_skelet( );
    g3dplan_main_window_objects *G3dplan_main_window =
    get_main_window_objects( );
    unsigned char   *img = get_img( );
    unsigned short *dist_img = get_dist_img( );
    int img_width = get_img_width( ),
```

```
        img_height = get_img_height( ),
        img_depth = get_img_depth( );
        SHOT   shot;
        int helmet;
        fputs("make_shots: make_shots & planning\n", stderr);
        if(dist_img == NULL)
        {
                dist_img = (unsigned short *)
                calloc(img_width*img_height*img_depth, sizeof(short));
                if(dist_img == NULL)
                {
                        fprintf(stderr,"make_shots . . . No memory
                        available (\n");
                        return;
                }
                if( !sedt(img, dist_img))
                {
                        fprintf(stderr,"make_shots . . . No memory
                        available \n");
                        return;
                }
                set_dist_img(dist_img);
}
/* gxv_start_connections DO NOT EDIT THIS SECTION */
shot.x = (float) atof(char *)xv_get(G3dplan_main_window->x,
        PANEL_VALUE));
        shot.y = (float) atof((char *)xv_get(G3dplan_main_window->y,
        PANEL_VALUE));
        shot.z = (float) atof((char *)xv_get(G3dplan_main_window->z,
        PANEL_VALUE));
        shot.r = (float) atof((char *)xv_get(G3dplan_main_window->r,
        PANEL_VALUE));
        cutimg(img,shot);
        first_skelet = add_node(shot.x, shot.y, shot.z, shot.r, 0,
        first_skelet);
        set_first_skelet(first_skelet);
        /* display_status(DISPLAY_SKELETON, first_skelet); */
        display_status(DISPLAY_ALL,img, first_skelet);
        return;
}
/*
 * processing routines for g3dplan;
 * display_status.c
 *
 */
#include "includes.h"
#include "g3dplan_ui.h"
#include "g3dplan_h"
extern g3dplan_main_window_objects *get_main_window_objects( );
extern char *get_prog_name( );
extern CONTOUR get_contour( );
extern int   get_img_width( ), get_img_height( ), get_img_depth( );
/* range of the image */
extern int mag3D( );
extern void GFree( );
extern int get_current_slice( );
extern void set_current_slice( );
extern ILIST *atoil(char *);
extern void FreeIlist(ILIST *);
/* X display variables */
extern Visual *get_visual( );
extern Display *get_display( );
extern Colormap get_colormap( );
extern Window   get_paint_window( ), get_sub_paint_window( );
extern GC   get_gc( ), get_sub_gc( );
extern unsigned long get_black_pixel( ), get_white_pixel( ),
get_red_pixel( ),
                        get_yellow_pixel( ), get_green_pixel( ),
                        get_gray_start_pixel( );
extern int        set_canvas_width( ), set_canvas_height( ),
                        set_sub_canvas_height( ),
                        set_sub_canvas_width( );
extern int        get_depth( );
extern unsigned   char *get_img( );
extern unsigned   char *get_tmp_img( );
extern SKELETON   *get_first_skelet( );
extern int        get_load_mag( );
extern void       display_array(int, int *, unsigned char *,
                        SKELETON *);
```

-continued

```
extern void         display_status(int, . . . );
extern float        get_weighting( );
extern float        get_drawr( );
void plus_slice( )
{
    g3dplan_window_array_objects   *get_window_array_pointer( );
    g3dplan_main_window_objects    *main_win =
    get_main_window_objects( );
    g3dplan_window_array_objects   *array =
    get_window_array_pointer( );
    int slice = get_current_slice( );
    int img_depth = get_img_depth( );
    int disp_type;
    int count, i;
    unsigned char *img = get_tmp_img( );
    SKELETON *first_skelet = get_first_skelet( );
    Display *display = get_display( );
    char * str = NULL;
    ILIST *list = NULL;
    int *index = NULL;
    /*
     * check current slice being displayed
     */
    if(slice >= (img_depth - 1))
        return;
    img = get_tmp_img( );
    slice = slice + 1;
    xv_set(main_win->slice_number, PANEL_VALUE, slice ,
    NULL);
    XFlush(display);
    set_current_slice(slice);
    if( img == NULL )
    {
        printf("display none . . . \n");
        disp_type = DISPLAY_NONE;
        display_status(disp_type);
    }
    else if (first_skelet == NULL)
    {
        disp_type = DISPLAY_IMAGE;
        display_status(disp_type, img);
    }
    else
    {
        disp_type = DISPLAY_ALL;
        display_status2(disp_type, img, first_skelet);
    }
    count = array->count;
    img = get_tmp_img( );
    if(count > 0 && img != NULL)
    {
        if(count > img_depth)
            count = img_depth;
        index = (int *) calloc(count, sizeof(int));
        if(index != NULL)
        {
            str = (char *) xv_get(main_win->slice_list,
            PANEL_VALUE);
            list = atoil(str);
            for(i=0;i<count;i++)
                index[i] = i;
            if(list != NULL)
            {
                for(i=0;i<(list->n);i++)
                {
                    if(list->data[i] >= 0 &&
                    list->data[i] < img_depth)
                        index[i] =
                        list->data[i];
                }
                FreeIlist(list);
                display_array(count, index, img, first_skelet);
                GFree(index);
            }
        }
    }
    return;
}
void minus_slice( )
```

```
{
    g3dplan_window_array_objects   *get_window_array_pointer( );
    g3dplan_main_window_objects    *main_win =
    get_main_window_objects( );
    g3dplan_window_array_objects   *array =
    get_window_array_pointer( );
    int slice = get_current_slice( );
    int img_depth = get_img_depth( );
    int disp_type;
    int count, i;
    unsigned char *img = get_tmp_img( );
    SKELETON *first_skelet = get_first_skelet( );
    Display *display = get_display( );
    int *index = NULL;
    char * str = NULL;
    ILIST *list = NULL;
    /*
     * check current slice being displayed
     */
    if(slice <= 0)
        return;
    slice = slice - 1;
    xv_set(main_win->slice_number, PANEL_VALUE, slice,
    NULL);
    XFlush(display);
    set_current_slice(slice);
    if( img == NULL )
    {
        printf("display none . . . \n");
        disp_type = DISPLAY_NONE;
        display_status(disp_type);
    }
    else if (first_skelet == NULL)
    {
        disp_type = DISPLAY_IMAGE;
        display_status(disp_type, img);
    }
    else
    {
        disp_type = DISPLAY_ALL;
        display_status2(disp_type, img, first_skelet);
    }
    count = array->count;
    img = get_tmp_img( );
    if(count > 0 && img != NULL)
    {
        if(count > img_depth)
            count = img_depth;
        index = (int *) calloc(count, sizeof(int));
        if(index != NULL)
        {
            str = (char *) xv_get(main_win->slice_list,
            PANEL_VALUE);
            list = atoil(str);
            for(i=0;i<count;i++)
                index[i] = i;
            if(list != NULL)
            {
                for(i=0;i<(list->n);i++)
                {
                    if(list->data[i] >= 0 &&
                    list->data[i] < img_depth)
                        index[i] =
                        list->data[i];
                }
            }
            FreeIlist(list);
            display_array(count, index, img, first_skelet);
            GFree(index);
        }
    }
    return;
}
#include "includes.h"
#include "g3dplan_ui.h"
#include "g3dplan_h"
extern void display_status( );
extern int mag3D( );
/* global variable */
```

```
extern g3dplan_main_window_objects *get_main_window_objects( );
extern int    get_img_width( ), get_img_height( ), get_img_depth( );
extern int    get_load_mag( );
extern unsigned char  *get_img( );
extern SKELETON *add_node( );
extern int    cutimg( );
extern unsigned short *get_dist_img( );
extern CONTOUR   get_contour( );
void  print_branch2(treeptr,filecount,shotlist, shot_num)
TREE   *treeptr;
int    *filecount;
SHOT   *shotlist;
int    shot_num;
{
    int   img_width = get_img_width( ),
          img_height = get_img_height( ),
          img_depth = get_img_depth( ); /* range of the image
          */
    int   load_mag = get_load_mag( );
    unsigned char  *img = get_img( );
    unsigned short *dist_img = get_dist_img( );
    g3dplan_main_window_objects  *G3dplan_main_window =
    get_main_window_objects( );
    CONTOUR contour = get_contour( );
    TREE   *tmpptr;
    FILE   *fp;
    char   filename[256];
    int    shotn=0;
    char   *curimg = NULL;
    unsigned short  *s1 = NULL, *s2=NULL, *finalimg= NULL;
    SKELETON  *sk= NULL, *tsk = NULL;
    int    i,area, unmatch;
    float  x,y,z,r, percent, overlap;
    if(treeptr == NULL)
    {
        printf("print_branch2:nothing to write,
        %s\n",filename);
        return;
    }
    overlap = (float)((int) xv_get(G3dplan_main_window->overlap,
    PANEL_VALUE));
/*  overlap /= 100; */
    /* after all, we would like to see how the plan looks like on
    the scree */
    curimg = (char *)calloc(img_height*img_width*img_depth,
    sizeof(char));
    finalimg = (unsigned short
    *)calloc(img_height*img_width*img_depth, sizeof(short));
    if(!curimg || !finalimg)
    {
        fprintf(stderr, "print_branch2: cannot allocate memory
        for images\n");
        exit[1];
    }
    mag3D(img,img_width,img_height,img_depth,curimg,1,1,1);
    for(i=0; i<shot_num; i++)
    {
        cutimg(curimg,shotlist[i]);
        sk = add_node(shotlist[i].x, shotlist[i].y,
        shotlist[i].z,shotlist[i].r, 0, sk);
    }
    tmpptr = treeptr;
    while(tmpptr->prev != NULL)
    {
        cutimg(curimg,tmpptr->shot);
        sk = add_node(tmpptr->shot.x, tmpptr->shot.y,
        tmpptr->shot.z,tmpptr->shot.r, 0, sk);
        tmpptr = tmpptr->prev;
    }
    display_status(DISPLAY_ALL,curimg,sk);
    if( !sedt(curimg, finalimg))
    {
        fprintf(stderr,"print_branch2: int_dist_img
        failed\n");
        GFree(curimg);
        GFree(finalimg);
        free_list(sk);
        return;
    }
```

-continued

```
        GFree(curimg);
        s1 = dist_img;
        s2 = finalimg;
        unmatch =0;
        area =0;
        for(i=0; i< (img_width*img_height*img_depth); i++)
        {
            if( (float)sqrt(s1[i]) <= (4.0*load_mag) &&
            (float)sqrt(s1[i]) >= (1.3*load_mag ))
            {
                if((float)sqrt(s2[i]) != 0.0)
                {
                    unmatch += s2[i];
                    area += s1[i];
                }
            }
        }
        percent = (float)unmatch/ (float)area;
        fprintf(stderr," area %d, unmatch %d, percent: %g\n", area,
        unmatch, percent);
        if(percent > overlap)
        {
            fprintf(stderr,"print_branch2: not going to write plan
            %d\n", *filecount);
            GFree(finalimg);
            free_list(sk);
            return;
        }
        /* fprintf(stderr,"print_branch2: display plan %d\n",
        *filecount);*/
        sprintf(filename, "plan%d", *filecount);
        tsk = sk;
        while(tsk != NULL)
        {
            tsk = tsk->next;
            shotn ++;
        }
        if((fp = fopen(filename, "w")) == NULL)
        {
            sprintf("print_branch: can not open file %s for
            write\n", filename);
            free_list(sk);
            exit[1];
        }
        fprintf(fp,"Shot Number: %d\n", shotn);
        tsk = sk;
        while(tsk != NULL)
        {
            fprintf((fp,"Shot: x: %f y: %f z:%f r: %f\n",
                (tsk->position).x,(tsk->position).y,(tsk->position).z,
                tsk->thickness);
            tsk = tsk->next;
        }
        tsk = sk;
        while(tsk != NULL)
        {
            x = (tsk->position.x)/load_mag + contour.min_x;
            y = (tsk->position.y)/(load_mag*1.1) + contour.min_y;
            z = (tsk->position.z)/(load_mag) + contour.min_z;
            r = (tsk->thickness)/load_mag;
            fprintf(fp,"real x: %f y: %f z: %f r: %f\n",x,y,z,r);
            tsk = tsk->next;
        }
        fprint(fp,"percent : %f\n", percent);
        fclose(fp);
        fprintf(stderr,"print_branch: write plan %d\n", *filecount);
        *(filecount) = *(filecount)+1;
/*
        notice = xv_create(Gammaplan_main_window->main_window,
        NOTICE,
            NOTICE_LOCK_SCREEN, FALSE,
            NOTICE_BLOCK_THREAD, TRUE,
            NOTICE_BUSY_FRAMES,
                Gammaplan_main_window->main_window,
                NULL,
            NOTICE_MESSAGE_STRINGS,"One Plan Finished",
            NULL,
            NOTICE_BUTTON_YES, "Continue",
            XV_SHOW, TRUE,
```

```
            NULL);
        xv_destroy(notice);
*/
        GFree(finalimg);
        free_list(sk);
        return;
/*    >>>>>>>>>>>>>>>>>>>>>>>  <<<<<<<<<<<<<<<<<<<<<<<
      >>>>
      >>>>    Library Routine for projecting
      >>>>    the skeleton
      >>>>
      >>>>>>>>>>>>>>>>>>>>>>>  <<<<<<<<<<<<<<<<<<<<<<< */
#include "includes.h"
#include "g3dplan.h"
#define Epsilon 1E-05
#define PI 3.1415927
extern matrix M; /* the transformation matrix */
void tr_matrix(float, float, float, float, float, float);
int project( unsigned char *scene,
             unsigned char **proj,
             float   alpha,
             float   beta,
             float   gamma,
             float   X,
             float   Y,
             float   Z,
             int     *output_size)
{
    int  w = get_img_width( ),
         h = get_img_height( ),
         d = get_img_depth( );   /* number of data elements in each
         direction */
    int proj_dim;                /* dimension of projection image */
    int i, j, k, index;
    float x, y, z;
    float xo, Yo, Zo;
    int   ix, iy, iz;
    unsigned char *scene_ptr = NULL;
    unsigned char *proj_data = NULL;
    /*
     * Check to see if the input an output objects passed into the
     1routine
     * are valid data objects.
     */
    if (!scene) {
       fprintf(stderr, "Input object is not a valid data object.");
       return (FALSE);
    }
    if (! proj ) {
       fprintf(stderr, "Output objects is not a valid data objects.");
       return (FALSE);
    }
    /*
     * Calculate the output object size w and h.
     */
    x = w;
    y = h;
    z = d;
    proj_dim = (int)(sqrt((double)(x*x + y*y + z*z)));
    *output_size = proj_dim;
    /*
     * Create value output objects and set their minimum attributes.
     */
    proj_data = (unsigned char *) calloc(proj_dim*proj_dim,
    sizeof(unsigned char));
    if ( ! proj_data )
    {
        fprintf(stderr, "proj: failed to create output projfer\n");
        return (FALSE);
    }
    *proj = proj_data;
    /*
     *
     * Here starts the ray casting algorithm.
     *
     */
    tr_matrix(alpha, beta, gamma, X, Y, Z);
    scene_ptr = scene;
    for(i=0;i<d;i++)
```

```
{
    for(j=0;j<h;j++)
    {
        for(k=0;k<w;k++)
        {
            if( (int) *scene_ptr > 0 )
            {
                x = k - 0.5*w;
                y = j - 0.5*h;
                z = i - 0.5*d;
                Xo = M[0][0]*x + M[1][0]*y + M[2][0]*z
                    + M[3][0];
                Yo = M[0][1]*x + M[1][1]*y + M[2][1]*z
                    + M[3][1];
                Zo = M[0[[2]*x + M[1][2]*y + M[2][2]*z
                    + M[3][2];
                ix = (Xo + 0.5);
                iy = (Yo + 0.5);
                iz = (Zo + 0.5);
                if(ix>=0 && ix < proj_dim && iz>=0 &&
                iz <proj_dim)
                {
                    index =
                    (proj_dim-1-iz)*proj_dim + ix;
                    proj_data[index]++;
                }
            }
            scene_ptr++;
        }
    }
}
return (TRUE);
}
/*
* recur_search problem: fo through all the combinations
*/
#include "includes.h"
#include "g3dplan_ui.h"
#include "g3dplan_h"
/* global variable */
extern int      calc_shots( );
extern int      get_stage( );
extern void     set_stage(int);
/* recursive search for all possible plans */
void    recur_search(ptr, filecount, level)
TREE    *ptr;
int     *filecount;
int     level;
{
    int     stage = get_stage( );
    int     i, node_count=0;
    SHOT    *shots=NULL;
    void    print_branch2( );
    /* search for all possible shots at current level */
    if( level == 1)
        stage = 1;
    set_stage(stage);
    if(*filecount==1)
        return;
    fprintf(stderr,"now enter recur_search at filecount %d level %d
    stage: %d\n", *filecount, level, stage);
    node_count = calc_shots(&shots,ptr);
    if(node_count == 0 && stage == 1)
    {
        set_stage(2);
        fprintf(stderr,"change stage : %d\n, get_stage( );
        GFree(shots);
        shots=NULL;
        fprintf(stderr,"doing calc_shots2 \n");
        node_count = calc_shots2(&shots,ptr);
        print_branch2(ptr,filecount,shots, node_count);
        set_stage(1);
        GFree(shots);
        shots = NULL;
    }
    else if( node_count != 0)
    {
        ptr->next = (TREE **)calloc(node_count,sizeof((TREE **));
        if(ptr->next == NULL)
```

```
            {
                fprintf(stderr,"recur_search: cannot locate
                memory for ptr->next\n");
                exit(1);
            }
            ptr->next_count = node_count;
            fprintf(stderr, "   new nodes: %d\n", node_count);
            for(i=0; i< (ptr->next_count); i++)
            {
                ptr->next[i] = (TREE *)calloc(1, sizeof(TREE));
                if(ptr->next[i] == NULL)
                {
                    fprintf(stderr,"recur_search: cannot
                    locate memory for ptr->next\n");
                    exit(1);
                }
                (ptr->next[i])->shot.x = shots[i].x;
                (ptr->next[i])->shot.y = shots[i].y;
                (ptr->next[i])->shot.z = shots[i].z;
                (ptr->next[i])->shot.r = shots[i].r;
                (ptr->next[i])->prev = ptr;
                (ptr->next[i])->next_count = 0;
                (ptr->next[i])->next = NULL;
            }
            GFree(shots);
            shots = NULL;
            for(i=0; i< (ptr->next_count); i++)
            {
                recur_search(ptr->next[i],filecount,
                (level+1));
            }
        }
    }
    return;
}
#include <math.h>
#include "includes.h"
#include "g3dplan.h"
#define SIGN(a,b) ((b)<0 ? -fabs(a) : fabs(a))
extern int get_stage( ), get_load_mag( );
int ridge(short *img, int w, int h, int d, unsigned char *grad)
{
    int i, j, k, index, i1, i2,c;
    double d1, d2, dx, dy, dz;
    double g;
    double **matrix = NULL;
    double dv[3], ev[3];
    void tred2( ), tqli( ), NRC_eigstr( );
    int stage = get_stage( ), load_mag = get_load_mag( ),cutoff;
    if(img == NULL || grad == NULL || w < 1 || h < 1 || d < 1)
        return 0;
    matrix = (double **) calloc(3, sizeof(double *));
    if(matrix == NULL)
    {
        free(grad);
    }
    for(i=0;i<3;i++)
    {
        matrix[i] = (double *) calloc(3, sizeof(double));
        if(matrix[i] == NULL)
        {
            for(j=0;j<i;j++)
                free(matrix[j]);
        }
    }
    if(stage == 2)
        cutoff = (int)(load_mag*RMIN*RMIN*load_mag);
    else
        cutoff = (int)(load_mag*R8[0]*R8[0]*load_mag);
    c = (int)sqrt((double)cutoff);
    index =-1;
    for(i=0;i<d;i++)
    {
        for(j=0;j<h;j++)
        {
            for(k=0;k<w;k++)
            {
                index ++ ;
                grad[index] = 0;
                if((int)img[index] >= cutoff)
```

```
{
    i1 = index −1;
    i2 = index +1;
    d1 = sqrt((double)img[i2])
    −sqrt((double)img[index]);
    d2 = sqrt((double)img[index]) −
    sqrt((double)img[i1]);
    dx = d1 − d2;
    i1 = index − w;
    i2 = index + w;
    d1 = sqrt((double)img[i2])
    −sqrt((double)img[index]);
    d2 = sqrt((double)img[index]) −
    sqrt((double)img[i]));
    dy = d1 − d2;
    i1 = index − w*h;
    i2 = index + w*h;
    d1 = sqrt((double)img[i2])
    −sqrt((double)img[index]);
    d2 = sqrt((double)img[index]) −
    sqrt((double)img[i1]);
    dz = d1 − d2;
    g =
    sqrt((double)(dx*dx(dy(dy+dz*dz));
    /*
     * the double grads
     */
    matrix[0][0] = −dx;
    matrix[1][1] = −dy;
    matrix[2][2] = −dz;
    /*
     * fxy
     */
    i1 = index − 1 −w;
    i2 = index + 1 + w;
    d1 = sqrt((double)img[i2]) +
    sqrt((double)img[i1]);
    i1 = index + 1 −w;
    i2 = index − 1 + w;
    d2 = sqrt(double)img[i2]) +
    sqrt((double)img[i1]);
    dx = 0.25*(d1 − d2);
    matrix[0][1] = matrix[1][0] =
    −dx;
    /*
     * fxz
     */
    i1 = index − 1 −w*h;
    i2 = index + 1 + w*h;
    d1 = sqrt((double)img[i2]) +
    sqrt((double)img[i1]);
    i1 = index + 1 −w*h;
    i2 = index − 1 + w*h;
    d2 = sqrt((double)img[i2]) +
    sqrt((double)img[i1]);
    dx = 0.25*(d1 − d2);
    matrix[0][2] = matrix[2][0] =
    −dx;
    /*
     * fyz
     */
    i1 = index − w −w*h;
    i2 = index + w + w*h;
    d1 = sqrt((double)img[i2]) +
    sqrt((double)img[i1]);
    i1 = index + w −w*h;
    i2 = index − w + w*h;
    d2 = sqrt((double)img[i2] +
    sqrt((double)img[i1]);
    dx = 0.25*(d1 − d2);
    matrix[1][2] = matrix[2][1] =
    −dx;
    tred2(matrix, 3, dv, ev);
    tqli(dv,ev,3,matrix);
    NRC_eigsrt(3, dv, matrix);
    if(dv[1]>0.5)
        {
            grad[index] = 5;
printf("ridge %d %d %d, %f %f %f\n", k,j,i, dv[0],dv[1],dv[2]);
```

```
                    }
                }
            }
        }
        for(i=0;i<3;i++)
            free(matrix[i]);
        free(matrix);
        return 1;
}
void NRC_eigsrt (n, eigval, eigvec)
int n;
double *eigval, **eigvec;
/*
    input:   eigval = eigenvalues in arbitrary order
             eigvec = column k of matrix is eigenvector for eigval[k]
    output:  eigval =eigenvalues in descending order, maximum in
                     eigval[0], minimum in eigval[n-1]
             eigvec = column k of matrix is eigenvector for eigval[k]
*/
{
    /* sort eigenvalues so that eigval[i] >= eigval[j] for i < j */
    int i, k, j;
    double max;
    for (i = 0; i <= (n-2); i++)
    {
        max = eigval[k=i];
        for (j = i+1; j < n; j++)
            if ( eigval[j] > max) max = eigval[k=j];
        if ( k != i)
        {
            /* swap eigenvalues */
            eigval[k] = eigval[i];
            eigval[i] = max;
            /* swap eigenvectors */
            for ( j = 0; j < n; j++)
            {
                float tmp = eigvec[j][i];
                eigvec[j][i] = eigvec[j][k];
                eigvec[j][k] = tmp;
            }
        }
    }
}
void tqli(d,e,n,z)
double d( ),e( ),**z;
int n;
{
        int m,l,iter,i,k;
        double s,r,p,g,f,dd,c,b;
        for (i=2;i<=n;i++) e[i-2]=e[i-1];
        e[n-1]=0.0;
        for (l=1;l<=n;l++) {
            iter=0;
            do {
                for (m=1;m<=n-1;m++) {
                    dd=fabs(d[m-1])+fabs(d[m]);
                    if (fabs(e[m-1])+dd == dd) break;
                }
                if (m != 1) {
                    if (iter++ == 30) {
                        printf("Too many iterations in
                            TQLI");
                        return;
                    }
                    g=(d[l]-d[l-1])/(2.0*e[l-1]);
                    r=sqrt((double)((g*g)+1.0));
                    g=d(m-1)-d[l-1]+e[l-1]/(g+SIGN(r,g));
                    s=c=1.0;
                    p=0.0;
                    for (i=m-1;i>=1;i--) {
                        f=s*e[i-1];
                        b=c*e[i-1];
                        if (fabs(f) >= fabs(g)) {
                            c=g/f;
                            r=sqrt((double)((c*c)+1.0));
                            e[i]=f*r;
                            c *= (s-1.0/r);
                        } else {
```

-continued

```
                    s=f/g;
                    r=sqrt((double)((s*s)+1.0));
                    e[i]=g*r;
                    s *= (c=1.0/r);
                }
                g=d[i]-p;
                r=(d[i-1]-g)*s+2.0*c*b;
                p=s*r;
                d[i]=g+p;
                g=c*r-b;
                /* Next loop can be omitted if
                eigenvectors not wanted */
                for (k=1;k<=n;k++) {
                    f=z[k-1][i];
                    z[k-1][i]=s*z[k-1][i-1]+c*f;
                    z[k-1][i-1]=c*z[k-1][i-1]-s*f;
                }
            }
            d[l-1]=d[l-1]-p;
            e[l-1]=g;
            e[m-1]=0.0;
        }
    } while (m != 1);
    }
}
void tred2(a,n,d,e)
double **d,d( ),e( );
int n;
{
    int l,k,j,i;
    double scale,hh,h,g,f;
    for (i=n;i>=2;i--) {
        l=i-1;
        h=scale=0.0;
        if (l > 1) {
            for (k=1;k<=1;k++)
                scale += fabs(s[i-1][k-1]);
            if (scale == 0.0)
                e[i-1]=a[i-1][l-1];
            else {
                for (k=1;k<=1;k++) {
                    a[i-1][k-1] /= scale;
                    h += a[i-1][k-1]*a[i-1][k-1];
                }
                f=a[i-1][l-1];
                g = f>0 ? -sqrt(h) : sqrt(h);
                e[i-1]=scale*g;
                h -= f*g;
                a[i-1][l-1]=g-g;
                f=0.0;
                for (j=1;j<=1;j++) {
                /* Next statement can be omitted if
                eigenvectors not wanted */
                    a[j-1][i-1]=a[i-1][j-1]/h;
                    g=0.0;
                    for (k=1;k<=j;k++)
                        g +=
                            a[j-1][k-1]*a[i-1][k-1];
                    for (k=j+1;k<=1;k++)
                        g +=
                            a[k-1][j-1]*a[i-1][k-1];
                    e[j-1]=g/h;
                    f +=e[j-1]*a[i-1][j-1];
                }
                hh=f/(h+h);
                for (j=1;j<=1;j++) {
                    f=a[i-1][j-1];
                    e[j-1]=g=e[j-1]-hh*f;
                    for (k=1;k<=j;k++)
                        a[j-1][k-1] -=
                            (f*e[k-1]+g*a[i-1][k-1]);
                }
            }
        } else
            e[i-1]=a[i-1][l-1];
        d[i-1]=h;
    }
    /* Next statement can be omitted if eigenvectors not wanted */
    d[l-1]=0.0;
```

```
            e[1-1]=0.0;
    /* Contents of this loop can be omitted if eigenvectors not
            wanted except for statement d[i]=a[i][i]; */
    for (i=1;i<=n;i++) {
        l=i-1;
        if (d[i-1]) {
            for (j=1;j<=1;j++) {
                g=0.0;
                for (k=1;k<=1;k++)
                    g += a[i-1][k-1]*a[k-1][j-1];
                for (k=1;k<=1;k++)
                    a[k-1][j-1] -= g*a[k-1][i-1];
            }
        }
        d[i-1]=a[i-1][i-1];
        a[i-1][i-1]=1.0;
        for (j=1;j<=1;j++) a[j-1][i-1]=a[i-1][j-1]=0.0;
    }
}
#include <math.h>
#include "includes.h"
#include "g3dplan.h"
#define SIGN(a,b) ((b)<0 ? fabs(a) : fabs(a))
extern int get_stage( ), get_load_mag( );
int ridge(short *img, int w, int h, ind d, unsigned char *grad)
{
    int i, j, k, index, i1, i2,c;
    double d1, d2, dx, dy, dz;
    double g;
    double **matrix = NULL;
    double dv[3], ev[3];
    void tred2( ), tqli( ), NRC_eigsrt( );
    int stage = get_stage( ), load_mag = get_load_mag( ),cutoff;
    if(img == NULL || grad == NULL || w < 1 || h < 1 || d < 1)
        return 0;
    matrix = (double **) calloc(3, sizeof(double *));
    if(matrix == NULL)
    {
        free(grad);
    }
    for(i=0;i<3;i++)
    {
        matrix[i] = (double *) calloc(3, sizeof(double));
        if(matrix[i] == NULL)
        {
            for(j=0;j<i;j++)
                free(matrix[j]);
        }
    }
    if(stage == 2)
        cutoff = (int)(load_mag*RMIN*RMIN*load_mag);
    else
        cutoff = (int)(load_mag*R8[0]*R8[0]*load_mag);
    c = (int)sqrt((double)cutoff);
    for(i=c;i<(d-c);i++)
    {
        for(j=c;j<(h-c);j++)
        {
            for(k=c;k<(w-c);k++)
            {
                index = k + (i*h + j)*w;
                grad[index] =
                    sqrt((double)img[index]);
            }
        }
    }
    for(i=0;i<3;i++)
        free(matrix[i]);
    free(matrix);
    return 1;
}
void NRC_eigsrt (n, eigval, eigvec)
int n;
double *eigval, **eigvec;
/*
    input:   eigval = eigenvalues in arbitrary order
             eigvec = column k of matrix is eigenvector for eigval[k]
    output:  eigval = eigenvalues in descending order, maximum in
                eigval[0], minimum in eigval[n-1]
```

```
            eigvec = column k of matrix is eigenvector for eigval[k]
*/
{
    /* sort eigenvalues so that eigval[i] >= eigval[j] for i < j */
    int i, k, j;
    double max;
    for (i = 0; i <= [n-2]; i++)
    {
        max = eigval[k=i];
        for [j = i+1; j < n; j++)
            if ( eigval[j] > max) max = eigval[k=j];
        if ( k != i)
        {
            /* swap eigenvalues */
            eigval[k] = eigval[i];
            eigval[i] = max;
            /* swap eigenvectors */
            for ( j = 0; j < n; j++)
            {
                float tmp = eigvec[j][i];
                eigvec[j][I] = eigvec[j][k];
                eigvec[j][k] = tmp;
            }
        }
    }
}
void tqli(d,e,n,z)
double d( ),e( ),**z,
int n;
{
            int m,l,iter,i,k;
            double s,r,p,g,f,dd,c,b;
            for (i=2;i<=n;i++) e[i-2]=e[i-1];
            e[n-1]=0.0;
            for (l=1;l<=n;l++) {
                    iter=0;
                    do {
                        for (m=1;m<=n-1;m++) {
                            dd=fabs(d[m-1])+fabs(d[m]);
                            if (fabs(e[m-1])+dd == dd) break;
                        }
                        if (m != 1) {
                            if (iter++ == 30) {
                                printf("Too many interations in
                                TQLI");
                                return;
                            }
                            g=(d[l]-d[l-1])/(2.0*e[l-1]);
                            r=sqrt((double)((g*g)+1.0));
                            g=d[m-1]-d[l-1]+e[l-1]/(g+
                            SIGN(r,g));
                s=c=1.0;
                p=0.0;
                for (i=m-1;i>=1;i--) {
                    f=s*e[i-1];
                    b=c*e[i-1];
                    if (fabs(f) >= fabs(g)) {
                        c=g/f;
                        r=sqrt((double)((c*c)+1.0));
                        e[i]=f*r;
                        c *= (s=1,0/r);
                    } else {
                        s=f/g;
                        r=sqrt((double)((s*s)+1.0));
                        e[i]=g*r;
                        s *= (c=1,0/r);
                    }
                    g=d[i]-p;
                    r=(d[i-1]-g)*s+2.0*c*b;
                    p=s*r;
                    d[i]=g+p;
                    g=c*r-b;
                    /* Next loop can be omitted if
                    eigenvectors not wanted */
                    for (k=1;k<=n;k++) {
                        f=z[k-1][i];
                        z[k-1][i]=s*z[k-1][i-1]+c*f;
                        z[k-1][i-1]=c*z[k-1][i-1]-s*f;
                    }
```

-continued

```
                    }
                    d[l-1]=d[l-1]-p;
                    e[l-1]=g;
                    e[m-1]=0.0;
                }
            } while (m != 1);
        }
    }
}
void tred(a,n,d,e)
double **a,d( ),e( );
int n;
{
    int l,k,j,i;
    double scale,hh,h,g,f;
    for (i=n;i>=2;i--) {
        l=i-1;
        h=scale=0.0;
        if (l > 1) {
            for (k=1;k<=1;k++)
                scale += fabs([i-1][k-1]);
            if (scale == 0.0)
                e[i-1]=a[i-1][l-1];
            else {
                for (k=1;k<=1;k++) {
                    a[i-1][k-1]/= scale;
                    h += a[i-1][k-1]*a[i-1][k-1];
                }
                f=a[i-1][l-1];
                g = f>0 ? -sqrt(h) : sqrt(h);
                e[i-1]=scale*g;
                h -= f*g;
                a[i-1][l-1]=f-g;
                f=0.0;
                for (j=1;j<=1;j++) {
                    /* Next statement can be omitted if
                       eigenvectors not wanted */
                    a[j-1][i-1]=a[i-1][j-1]/h;
                    g=0.0;
                    for (k=1;k<=j;k++)
                        g +=
                            a[j-1][k-1]*a[i-1][k-1];
                    for (k=j+1;k<=1;k++)
                        g +=
                            a[k-1][j-1]*a[i-1][k-1];
                    e[j-1]=g/h;
                    f += e[j-1]*a[i-1][j-1];
                }
                hh=f/(h+h);
                for (j=1;j<=1;j++) {
                    f=a[i-1 [j-1];
                    e[j-1]=g=e[j-1]-hh*f;
                    for (k=1;k<=j;k++)
                        a[j-1][k-1] -=
                            (f*e[k-1]+g*a[i-1][k-1]);
                }
            }
        } else
            e[i-1]=a[i-1][l-1];
        d[i-1]=h;
    }
    /* Next statement can be omitted if eigenvectors not wanted */
    d[l-1]=0.0;
    e[l-1]=0.0;
    /* Contents of this loop can be omitted if eigenvectors not
       wanted except for statement d[i]=a[i][i]; */
    for (i=1;i<=n;i++) {
        l=i-1;
        if (d[i-1]) {
            for (j=1;j<=1;j++) {
                g=0.0;
                for (k=1;k<=1;k++)
                    g += a[i-1][k-1]*a[k-1][j-1];
                for (k=1;k<=1;k++)
                    a[k-1][j-1] -= g*a[k-1][i-1];
            }
        }
        d[i-1]=a[i-1][i-1];
        a[i-1][i-1]=1.0;
        for (j=1;j<=1;j++) a[j-1][i-1]=a[i-1][j-1]=0.0;
```

```
        }
}
#include <stdio.h>
#include <malloc.h>
#include <math.h>
#include "includes.h"
#include "g3dplan_ui.h"
#include "g3dplan.h"
extern void GFree( );
extern void FreeContour( );
/*
 * roi_1gp2g3dp: get vertices for 1gp ROI file as g3dplan's contour
 files (slices by slice)
 *
 * usage:
 *
 *    roi_1gp2g3dp: input_file output_file
 *
 */
typedef struct
{
    float x;
    float y;
    float z;
} RVert;
typedef struct
{
    int     no_vert;
    int     type; /* usually it is 34 */
    RVert   *v;
} ROI;
main(argc, argv)
int argc;
char **argv;
{
    int i,j, slice;
    float x1,y1,x2,y2,d;
    int type = 34;
    char *input = NULL, *output = NULL;
    char str[250];
    FILE *fp = NULL;
    ROI roi;
    CONTOUR contour;
    if ( argc != 3 )
    {
        fprintf(stderr, "Usage is: %s input_file
        output_file\n", argv[0]);
        exit(1);
    }
    input = argv[1];
    output = argv[2];
    /*
     * read the contour file
     */
    if ((fp = fopen(input,"r")) == NULL)
    {
        fprintf(stderr, "roi_1gp2g3dp: can not open file % to
        read \n", input);
        exit( );
    }
    if((fread(&(roi.no_vert), sizeof(int),l, fp) != 1))
    {
        fclose(fp);
        fprintf(stderr, "roi_1gp2g3dp: read file %s error \n",
        input);
        exit(1);
    }
    if((fread(&(roi.type), sizeof(int),l, fp) != 1))
    {
        fclose(fp);
        fprintf(stderr, "roi_1gp2g3dp: read file %s error \n",
        input);
        exit(1);
    }
    fprintf(stderr,"%d->", roi.no_vert);
    roi.v = (RVert *)calloc(roi.no_vert, sizeof(RVert));
    if(roi.v == NULL)
    {
        fclose(fp);
```

```
            fprintf(stderr, "roi_1gp2g3dp: allocate memory %s \n",
            input);
            exit(1);
    }
    for(i=0; i<roi.no_vert; i++)
    {
            if((fread(&(roi.v[i]), sizeof(RVert),1, fp) != 1))
            {
                    fclose(fp);
                    fprintf(stderr, "roi_1gp2g3dp: read file %s
                    error \n", input);
                    exit(1);
            }
    }
    fclose(fp);
    j=1;
    if ((fp = fopen(output,"w")) == NULL)
    {
            printf(stderr, "roi_1gp2g3dp: can not open file %s to
            read \n", input);
            exit(1);
    }
    fprintf(fp,"%5.2f\n", (roi.v[1]).z);
    fprintf(fp,"%5.2f &5.2f ", (roi.v[1]).x, (roi.v[1]).y);
    x1 = roi.v[1].x;
    y1 = roi.v[1].y;
    for(i=1; i<roi.no_vert; i++)
    {
            x2 = roi.v[i].x;
            y2 = roi.v[i].y;
            d = (x1-x2)*(x1-x2) + (y1-y2)*(y1-y2);
            if( d > 1.0 )
            {
                    fprintf(fp,"%5.2f %5.2f ",
                    (roi.v[i]).x, (roi.v[i]).y);
                    x1 = x2;
                    y1 = y2;
                    j++;
            }
            if( (j % 7) == 0)
                fprintf(fp,"\n");
    }
    fprintf(fp,"\n");
    fprintf(fp,"%d\n", j);
    fprintf(stderr, "%d\n", j);
    exit(0);
}
#include <math.h>
#include "includes.h"
#include "g3dplan_ui.h"
#include "g3dplan.h"
#define MAXVAL 32767
#define SQR(X) ((float)((float)(X)*(float)(X)))
extern int   get_img_width( ), get_img_height( ), get_img_depth( );
/* range of the image */
extern int mag3D( );
extern int mag2D( );
extern void GFree( );
extern g3dplan_main_window_objects *get_main_window_objects( );
extern Display * get_display( );
/*
 * Routine Name: sedt  Do the distance function of a binary image.
 *
 */
int sedt(img1, img2)
unsigned char *img1;
short *img2;
{
    int img_width = get_img_width( ), img_height =
    get_img_height( ), img_depth = get_img_depth( );
    g3dplan_main_window_objects *main_win =
    get_main_window_objects( ),
    Display *display = get_display( );
    int i, j, k, r, offset, index;
    int row, col, depth;
    short C1x,C1y,C1z, C2z,C2y,C2x;
    short *Jx1 = NULL, *Jy1 = NULL, *Jx2 = NULL, *Jy2 = NULL,
    *Jz1 = NULL, *Jz2 = NULL;
    if(!img) || !img2)
```

```
        return (0);
/* vector images */
Jx2 = (short *)calloc(img_width*img_height, sizeof((short));
Jy2 = (short *)calloc(img_width*img_height, sizeof((short));
Jz2 = (short *)calloc(img_width*img_height, sizeof((short));
Jx1 = (short *)calloc(img_width*img_height, sizeof((short));
Jy1 = (short *)calloc(img_width*img_height, sizeof((short));
Jz1 = (short *)calloc(img_width*img_height, sizeof((short));
if( !Jx1 || !Jy1 || !Jz1 || !Jx2 || !Jy2 || !Jz2 )
{
    GFree(Jx1);
    GFree(Jy1);
    GFree(Jz1);
    GFree(Jx2);
    GFree(Jy2);
    GFree(Jz2);
    xv_set(main_win->main_window,
    FRAME_LEFT_FOOTER, "sedt: memory
    allocation failure", NULL);
    XBell(display, 0);
    return(0);
}
for (i = 0; i < img_width*img_height; i++)    /* initialize
plane images */
{
        Jy1[i] = Jx1[i] = Jz1[i]= 0;
}
/*
r=0;
for(i=0; i<img_depth; i++)
{
        printf("slice %d\n", i);
    for(j=0; j<img_height; j++)
    {
        for(k=0; k<img_width; k++)
        {
            printf("%d ", img1[r]);
            r++;
        }
        printf("\n");
    }
        printf("\n");
}
*/
/* forward loop */
offset = 0;
for(depth =0; depth <img_depth; depth++)
{
    for (i = ; i< img_width*img_height; i++)
    initialize plane images */
    {
        if ((int) img1[i+offset] == (int) 1)
            Jy2[i] = Jx2[i] = Jz2[i]= MAXVAL;
        else
            Jy2[i] = Jx2[i] = Jz2[i]= 0;
    }
    /*
     * init the frame . . .
     */
    k= img_width*img_height;
    for(i=0;i<img_width;i++)
    {
            index = i;
            Jx2[index] = Jy2[index] = Jz2[index] = 0;
            Jx2[index+k-img_width] =
            Jy2[index+k-img_width] =
            Jz2[index+k-img_width] = 0;
    }
    for(i=0;i<k;i+= img_width)
    {
            Jx2[index] = Jy2[index] =
            Jz2[index] = 0;
            Jx2[index+img_width-1] =
            Jy2[index+img_width-1] =
            Jz2[index+img_width-1] = 0;
    }
    /* 1st loop of Danielson's alg. */
    for (row = 0; row < img_height; row++)
    {
```

```
            r = row * img_width;
            if (row != 0)
            {
                for (j = 1; j < img_width; j++) /* skip first
                line and column */
                {
                    k = r + j;
                    if(img1[offset+k] == 0)
                            continue;
                    C1x = Jx2[k];
                    C1y = Jy2[k];
                    C1z = Jz2[k];
                    C2x = Jx1[k];
                    C2y = Jy1[k];
                    C2z = Jz1[k] - 1;
                    if (SQR(C1x) + SQR(C1y) + SQR(C1z) >
                    SQR(C2x) + SQR(C2y) + SQR(C2z))
                    {
                        C1x = C2x;
                        C1y = C2y;
                        C1z = C2z;
                    }
                    C2x = Jx2[k - img_width];
                    C2y = Jy2[k - img_width]-1;
                    C2z = Jz2[k - img_width];
                    if (SQR(C1x) + SQR(C1y) + SQR(C1z) >
                    SQR(C2x) + SQR(C2y) + SQR(C2z))
                    {
                        C1x = C2x;
                        C1y = C2y;
                        C1z = C2z;
                    }
                    C2x = Jx2[k - 1] - 1;
                    C2y = Jy2[k - 1];
                    C2z = Jx2[k - 1];
                    if (SQR(C1x) + SQR(C1y) + SQR(C1z) >
                    SQR(C2x) + SQR(C2y) + SQR(C2z))
                    {
                        Jx2[k] = C2x;
                        Jy2[k] = C2y;
                        Jz2[k] = C2z;
                    }
                    else
                    {
                        Jx2[k] = C1x;
                        Jy2[k] = C1y;
                        Jz2[k] = C1z;
                    }
                }
            }
            for (j = img_width - 2; j >= 0; j--) /* skip last column
            */
                k = r + j;
                if(img1[offset+k] == 0)
                        continue;
                C1x = Jx2[k];
                C1y = Jy2[k];
                C1z = Jz2[k];
                C2x = Jx2[k + 1] + 1;
                C2y = Jy2[k + 1];
                C2z = Jz2[k + 1];
                if (SQR(C1x) + SQR(C1y) + SQR(C1z) >
                SQR(C2x) + SQR(C2y) + SQR(C2z))
                {
                    Jx2[k] = C2x;
                    Jy2[k] = C2y;
                    Jz2[k] = C2z;
                }
            }
        }
        for (row = img_height - 2: row >= 0; row--) /* 2nd loop of
        Danielson's alg. */
        {
            r = row * img_width;
            for (j = img_width - 1; j >= 0; j--)   /* skip last line
            and column */
            {
                k = r + j;
                if(img1[offset+k] == 0)
```

```
                    continue;
                C1x = Jx2[k];
                C1y = Jy2[k];
                C1z = Jz2[k];
                C2x = Jx2[k + img_width];
                C2y = Jy2[k + img_width] + 1;
                Cz2 = Jx2[k + img_width];
                if (SQR(C1x) + SQR(C1y) + SQR(C1z) ×
                SQR(C2x) + SQR(C2y) + SQR(C2z))
                {
                    Jx2[k] = C2x;
                    Jy2[k] = C2y;
                    Jz2[k] = C2z;
                }
            }
        }
        for (i = 0; i < img_width*img_height; i++)
        {
            img2[i+offset] = (short)(SQR(Jx2[i]) + SQR(Jys[i]) +
            SQR(Jz2[i]));
        }
        memcpy((char *) Jx1, (char *) Jx2,
        img_width*img_height*sizeof(short));
        memcpy((char *) Jy1, (char *) Jy2,
        img_width*img_height*sizeof(short));
        memcpy((char *) Jz1, (char *) Jz2,
        img_width*img_height*sizeof(short));
        offset += img_width * img_height;
    }
    /* the backward loop */
    for (i = 0; i < img_width*img_height; i++)     /* initialize
    plane images */
    {
        Jy1[i] = Jx1[i] = Jz1[i]= 0;
    }
    offset = (img_depth-1)*img_width*img_height;
    for(depth =img_depth -1 ; depth >= 0; depth--)
    {
        for (i = 0; i < img_width*img_height; i++)     /*
        initialize plane images */
        {
            if ((int) img1[i+offset] == (int) 1)
                Jy2[i] = Jx2[i] = Jz2[i] = MAXVAL;
            else
                Jy2[i] = Jx2[i] = Jz2[i]= 0;
        }
    /*
     * init the frame . . .
     */
    k= img_width*img_height;
    for(i=0;i<img_width;i++)
    {
        index = i;
        Jx2[index] = Jy2[index] = Jx2[index] = 0;
        Jx2[index+k-img_width] = Jy2[index+k-img_width] =
        Jz2[index+k-img_width] = 0;
    }
    for(i=0;i<k;i+= img_width)
    {
        Jx2[index] = Jy2[index] = Jx2[index] = 0;
        Jx2[index+img_width-1] = Jy2[index+img_width-1] =
        Jz2[index+img_width-1] = 0;
    }
    for (row = img_height - 1; row >= 0; row--)
    {
        r = row + img_width;
        if (row != (img_width-1))
        {
            for (j = img_width-2; j >= 0; j--) /* skip last
            line and column */
            {
                k = r + j;
                if(img1[offset+k] == 0)
                    continue;
                C1x = Jx2[k];
                C1y = Jy2[k];
                C1z = Jz2[k];
                C2x = Jx1[k];
                C2y = Jy1[k];
```

```
                C2z = Jz1[k] + 1;
                if (SQR(C1x) + SQR(C1y) + SQR(C1z) >
                SQR(C2x) + SQR(C2y) + SQR(C2z))
                {
                        C1x = C2x;
                        C1y = C2y;
                        C1z = C2z;
                }
                C2x = Jx2[k + img_width];
                C2y = Jy2[k + img_width]+1;
                C2z = Jz2[k + img_width];
                if (SQR(C1x) + SQR(C1y) + SQR(C1z) >
                SQR(C2x) + SQR(C2y) + SQR(C2z))
                {
                        C1x = C2x;
                        C1y = C2y;
                        C1z = C2z;
                }
                C2x = Jx2[k + 1] + 1;
                C2y = Jy2[k + 1];
                C2z = Jx2[k + 1];
                if (SQR(C1x) + SQR(C1y) + SQR(C1z) >
                SQR(C2x) + SQR(C2y) + SQR(C2z))
                {
                    Jx2[k] = C2x;
                    Jy2[k] = C2y;
                    Jz2[k] = C2z;
                }
                else
                {
                    Jx2[k] = C1x;
                    Jy2[k] = C1y;
                    Jz2[k] = C1z;
                }
            }
        }
        for (j = 1 ; j < img_width; j++)
        {
            k = r + j;
            if(img1[offset+k] == 0)
                continue;
            C1x = Jx2[k];
            C1y = Jy2[k];
            C1z = Jz2[k];
            C2x = Jx2[k - 1] - 1;
            C2y = Jy2[k - 1];
            Cz2 = Jz2[k - 1];
            if (SQR(C1x) + SQR(C1y) + SQR(C1z) >
            SQR(C2x) + SQR(C2y) + SQR(C2z))
            {
                    Jx2[k] = C2x;
                    Jy2[k] = C2y;
                    Jz2[k] = C2z;
            }
        }
    }
}
for (row = 1; row < img_height; row++)
{
    r = row + img_width;
    for (j = 0; j < img_width; j++)
    {
        k = r + j;
        if(img1[offset+k] == 0)
            continue;
        C1x = Jx2[k];
        C1y = Jy2[k];
        C1z = Jz2[k];
        C2x = Jx2[k - img_width];
        C2y = jy2[k - img_width] - 1;
        C2z = Jz2[k - img_width];
        if (SQR(C1x) + SQR(C1y) + SQR(C1z) >
        SQR(C2x) + SQR(C2y) + SQR(C2z))
        {
            Jx2[k] = C2x;
            Jy2[k] = C2y;
            Jz2[k] = C2z;
        }
    }
}
```

-continued

```
                k=0;
                for (i = ; i < img_height;i++)
                {
                        for(j=0; j<img_width; j++)
                        {
                                r = (short)(SQR(Jx2[k]) + SQR(Jy2[k]) +
                                SQR(Jz2[k]));
                                if( img2[offset+k] > r)
                                img2[offset+k] = r;
                                k++;
                        }
                }
                memcpy((char *) Jx1, (char *) Jx2,
                img_width*img_height*sizeof(short));
                memcpy((char *) Jy1, (char *) Jy2,
                img_width*img_height*sizeof(short));
                memcpy((char *) Jz1, (char *) Jz2,
                img_width*img_height*sizeof(short));
                offset -= img_width * img_height;
        }
GFree(Jx1);
GFree(Jy1);
GFree(Jz1);
GFree(Jx2);
GFree(Jy2);
GFree(Jx2);
/*
r=0;
for(i=0; i<img_depth; i++)
{
                print("slice %d\n", i);
                for(j=0; j<img_height; j++)
                {
                        for(k=0; k<img_width; k++)
                        {
                                printf("%d ", img2[r]);
                                r++;
                        }
                        printf("\n");
                }
                printf("\n");
        }
   */
        return(1);
}
/*
 * set_canvas.c
 */
#include "includes.h"
#include "g3dplan_ui.h"
#include "g3dplan.h"
/*
 * external function definitions.
 */
extern g3dplan_main_window_objects  *get_main_window_objects( );
extern g3dplan_sub_window_objects   *get_sub_window_objects( );
extern char *get_prog_name( );
extern Visual       *get_visual( );
extern void         set_visual(Visual *);
extern Display      *get_display( );
extern void         set_display(Display *);
extern Colormap     get_colormap( );
extern void         set_colormap(Colormap);
extern window       get_paint_window( ), get_sub_paint_window( );
extern void         set_paint_window(Window),
set_sub_paint_window(Window);
extern GC           get_gc( ), get_sub_gc( );
extern void         set_gc(GC), set_sub_gc(GC);
extern unsigned long get_black_pixel( ), get_white_pixel( ),
get_red_pixel( ),
                get_yellow_pixel( ), get_green_pixel( ),
                get_blue_pixel( ),
                get_brown_pixel( ), get_orange_pixel( ),
                get_gray_start_pixel( );
extern void     set_black_pixel(unsigned long),
set_white_pixel(unsigned long),
                set_red_pixel(unsigned long), set_yellow_pixel(unsigned
                long),
                set_blue_pixel(unsigned long),
```

-continued

```
                    set_brown_pixel(unsigned long),
                    set_orange_pixel(unsigned long),
                    set_green_pixel(unsigned long),
                    set_gray_start_pixel(unsigned long);
extern int          get_canvas_width( ), get_canvas_height( );
extern void         set_canvas_width( ), set_canvas_height(int);
extern int          get_sub_canvas_width( ), get_sub_canvas_height( );
extern void         set_sub_canvas_width(int), set_sub_canvas_height(int);
extern int          get_depth( );
extern void         set_depth(int);
extern char *       get_prog_name( );
extern Attr_attribute   INSTANCE;
/* global variable */
void set_canvas( )
{
    g3dplan_main_window_objects    *main_win =
    get_main_window_objects( );
    g3dplan_sub_window_objects     *sub_win =
    get_sub_window_objects( );
    char *prog_name = get_prog_name( );
    Visual     *visual = get_visual( );
    Display    *display = get_display( );
    Colormap   cmap = get_colormap( );
    Window     paint_window = get_paint_window( ),
               sub_paint_window = get_sub_paint_window( );
    GC         gc = get_gc( ), sub_gc = get_sub_gc( );
    unsigned   long black_pixel = get_black_pixel( ),
        white_pixel = get_white_pixel( ),
        red_pixel = get_red_pixel( ),
        yellow_pixel = get_yellow_pixel( ),
        green_pixel = get_green_pixel( ),
        blue_pixel = get_blue_pixel( ),
        brown_pixel = get_brown_pixel( ),
        orange_pixel = get_orange_pixel( ),
        gray_start_pixel = get_gray_start_pixel( );
    int        canvas_width = get_canvas_width( ), canvas_height =
    get_canvas_width( );
    int        sub_canvas_width = get_sub_canvas_width( ),
               sub_canvas_height = get_sub_canvas_height( );
    int        depth = get_depth( );
    Xv_Screen xv_screen;
    int screen, i, min, max;
    Xv_Window paint_xv_window;
    XColor colour;
    unsigned long plane_mask;
    XGCValues values;
    XVisualInfo visual_info;
    unsigned long gc_mask;
    unsigned long colors(GRAY_COLORS);
    display = (Display *)xv_get(main_win->main_canvas,
    XV_DISPLAY);
    set_display(display);
    xv_screen = (Xv_Screen)xv_get(main_win->main_canvas,
    XV_SCREEN);
    screen = (int)xv_get(xv_screen,SCREEN_NUMBER);
    paint_xv_window = (Xv_Window)xv_get(main_win->
    main_canvas, CANVAS_NTH_PAINT_WINDOW, 0);
    paint_window = (Window) xv_get(paint_xv_window,XV_XID);
    set_paint_window(paint_window);
    paint_xv_window = (Xv_Window)xv_get(sub_win->sub_canvas,
    CANVAS_NTH_PAINT_WINDOW, 0);
    sub_paint_window = (Window) xv_get(paint_xv_window,
    XV_XID);
    set_sub_paint_window(sub_paint_window);
    visual = DefaultVisual(display, screen);
    set_visual(visual);
    depth = DefaultDepth(display, screen);
    set_depth(depth);
    if(visual->class != PseudoColor)
    {
        if(!XMatchVisualInfo(display, screen, 8, PseudoColor,
        &visual_info))
        {
            fprintf(stderr,"%s: Could not get PseudoColor
            Visual\n", prog_name);
            exit(1);
        }
        visual = visual_info.visual;
    }
```

-continued

```
        cmap = DefaultColormap(display, screen);
        set_colormap(cmap);
        if( !XAllocColorCells(display, cmap, False, &plane_mask, 0,
        color, EXTRA_COLORS))
        {
            fprintf(stderr,"%s: Could not allocate 4 colors for
            display\n", prog_name);
            exit(1);
        }
/*
 * define colors
 */
        colour.pixel = colors[0];
        colour.red = colour.blue = colour.green = 0;
        colour.flags = DoRed | DoGreen | DoBlue;
        XStoreColor(display, cmap, &colour);
        colour.pixel = colors[1];
        colour.red = colour.blue = colour.green = 65535;
        colour.flags = DoRed | DoGreen | DoBlue;
        XStoreColor(display, cmap, &colour);
        colour.pixel = colors[2];
        colour.blue = colour.green = 0;
        colour.red = 65535;
        colour.flags = DoRed | DoGreen | DoBlue;
        XStoreColor(display, cmap, &colour);
        colour.pixel = colors[3];
        colour.blue = 0;
        colour.red = colour.green = 65535;
        colour.flags = DoRed | DoGreen | DoBlue;
        XStoreColor(display, cmap, &colour);
        colour.pixel = colors[4];
        colour.blue = colour.red = 0;
        colour.green = 65535;
        colour.flags = DoRed | DoGreen | DoBlue;
        XStoreColor(display, cmap, &colour);
        colour.pixel = colors[5];
        colour.red = 135*256;
        colour.green = 205*256;
        colour.blue = 235*256;
        colour.flags = DoRed | DoGreen | DoBlue;
        XStoreColor(display, cmap, &colour);
        colour.pixel = colors[6];
        colour.red = 255*256;
        colour.blue = 72*256;
        colour.green = 727*256;
        colour.flags = DoRed | DoGreen | DoBlue;
        XStoreColor(display, cmap, &colour);
        colour.pixel = colors[7];
        colour.red = 65535;
        colour.green = 140*256;
        colour.blue = 0;
        colour.flags = DoRed | DoGreen | DoBlue;
        XStoreColor(display, cmap, &colour);
        black_pixel = colors[0];
        white_pixel = colors[1];
        red_pixel = colors[2];
        yellow_pixel = colors[3];
        green_pixel = colors[4];
        blue_pixel = colors[5];
        brown_pixel = colors[6];
        orange_pixel = colors[7];
        set_black_pixel(black_pixel);
        set_white_pixel(white_pixel);
        set_red_pixel(red_pixel);
        set_yellow_pixel(yellow_pixel);
        set_green_pixel(green_pixel);
        set_blue_pixel(blue_pixel);
        set_brown_pixel(brown_pixel);
        set_orange_pixel(orange_pixel);
/*
 * now the gray scale ramp
 */
        if( !XAllocColorCells(display, cmap, False, &plane_mask, 0,
        colors, GRAY_COLORS))
        {
            fprintf(stderr,"set_canvas: Could not allocate %d
            colors for display\n", GRAY_COLORS);
            exit(1);
        }
```

-continued

```
    min = max = colors[0];
    for(i=1;i<GRAY_COLORS;i++)
    {
        if(colors[i] < min)
            min = colors[i];
        if(colors[i] > max)
            max = colors[i];
    }
    if((max - min) != (GRAY_COLORS-1))
    {
        fprintf(stderr,"%s: set_canvas: mas - min !=
        GRAY_COLORS\n", prog_name);
        fprintf(stderr,"          bug in X Server\n");
        exit(1);
    }
    gray_start_pixel = min;
    for(i=0;i<GRAY_COLORS;i++)
    {
        colour.pixel = gray_start_pixel + i;
        color.red = color.green = colour.blue =
            i * MAX_16BIT / GRAY_COLORS;
        colour.flags = DoRed | DoGreen | DoBlue;
        XStoreColor( display, cmap, &colour);
    }
    set_gray_start_pixel(gray_start_pixel);
    /*
     * set the graphics contexts
     */
    values.foreground = white_pixel;
    values.background = black_pixel;
    values.function = GXcopy;
    values.line_width = 0;
    values.line_style = LineSolid;
    gc_mask = GCFunction | GCForeground | GCBackground |
                    GCLineWidth | GCLineStyle;
    gc = XCreateGC(display, paint_window, gc_mask, &values);
    sub_gc = XCreateGC(display, sub_paint_window, gc_mask,
    &values);
    set_gc(gc);
    set_sub_gc(gc);
    XSetBackground(display, gc, black_pixel);
    XSetForeground(display, gc, white_pixel);
    XSetBackground(display, sub_gc, black_pixel);
    XSetForeground(display, sub_gc, white_pixel);
    XClearWindow(display, paint_window);
    XClearWindow(display, sub_paint_window);
    XSetWindowBackground(display, paint_window, black_pixel);
    XSetWindowBackground(display, sub_paint_window, black_pixel);
    canvas_width = (int) xv_get(main_win->main_canvas,
    CANVAS_WIDTH);
    canvas_height = (int) xv_get(main_win->main_canvas,
    CANVAS_HEIGHT);
    set_canvas_width(canvas_width);
    set_canvas_height(canvas_height);
    xv_set(main_win->main_canvas,
    CANVAS_MIN_PAINT_WIDTH, canvas_width, NULL);
    xv_set(main_win->main_canvas,
    CANVAS_MIN_PAINT_HEIGHT, canvas_height, NULL);
    xv_set(main_win->main_canvas,
    CANVAS_AUTO_EXPAND, TRUE, NULL);
    xv_set(main_win->main_canvas, CANVAS_AUTO_SHRINK,
    FALSE, NULL);
    sub_canvas_width = (int) xv_get(sub_win->sub_canvas,
    CANVAS_WIDTH);
    sub_canvas_height = (int) xv_get(sub_win->sub_canvas,
    CANVAS_HEIGHT);
    set_sub_canvas_width(sub_canvas_width);
    set_sub_canvas_height(sub_canvas_height);
    xv_set(sub_win->sub_canvas, CANVAS_MIN_PAINT_WIDTH,
    sub_canvas_width, NULL);
    xv_set(sub_win->sub_canvas,
    CANVAS_MIN_PAINT_HEIGHT,
    sub_canvas_height, NULL);
    xv_set(sub_win->sub_canvas,
    CANVAS_AUTO_EXPAND, TRUE, NULL);
    xv_set(sub_win->sub_canvas,
    CANVAS_AUTO_SHRINK, FALSE, NULL);
    return;
}
```

```
/*
 * calculate possible shots from crosspt list
 *
 */
#include "includes.h"
#include "g3dplan_ui.h"
#include "g3dplan.h"
extern void  free_list( );
extern in    mag3D( ), cutimg( );
extern SKELETON  *delet_node( ), *delete_node( );
extern SKELETON  *add_node( );
extern int   touch2( );
/* global variable */
extern int       get_img_width( ), get_img_height( ), get_img_depth( );
extern int       get_load_mag( ), get_stage( );
extern unsigned short  *get_dist_img( );
int   shotsfromcross(crosspts,list)
SKELETON  *crosspts, **list;
{
    int     load_mag = get_load_mag( ),
            img_width = get_img_width( ),
            img_height = get_img_height( ),
            img_depth = get_img_depth( ),
            stage = get_stage( );
    unsigned short  *dist_img = get_dist_img( );
    int     shot_count=0;
    int     i;
    TREE    *tpt;
    SKELETON  *sk4shot= NULL, *tsk=NULL;
    SKELETON  *newsk4shot = NULL,*tmpc= NULL,
              *compare=NULL;
    float   x1,y1, z1,r1,x2, y2,z2,r2,dis, ax, ay,za, ar;
    int     n=1; ind;
    unsigned short  *s=NULL;
    s = dist_img;
    if( crosspts != NULL)
    {
        /* fprintf(stderr,"shotsfrom cross: list \n"); */
        tsk = crosspts;
        while(tsk != NULL)
        {
            x1= tsk->position.x;
            y1= tsk->position.y;
            z1 = tsk->position.z;
            r1 = tsk->thickness;
            /* fprintf(stderr,"       (%4.1f,
            %4.1f, %4.1f,%41.f)\n",
            x1, y1,z1,r1); */
            ind = (((int)z1) *img_height +
            (int)y1)*img_width*(int)x1;
            if( (float)(fabs[r]*r1 - s[ind])) > 3) /* means
            inside region, loose limit applied */
            {
                if( r1 <= (R18[1]*load_mag) && r1 >=
                (RMIN*load_mag) && stage == 2)
                {
                    sk4shot =
                    add_node(tsk->position.x,tsk->position.y,
                    tsk->position.z, 0, sk4shot);
                    shot_count ++;
                }
                else if( r1 <= (R18[1]*load_mag) && r1
                >= (R8[0]*load_mag) && stage == 1)
                {
                    sk4shot =
                    add_node(tsk->position.x,tsk->position.y,
                    tsk->position.z, 0, sk4shot);
                    shot_count ++;
                }
            }
            else
            {
                if( r1 <= (R18[1]*load_mag) && r1 >=
                (R8[0]*load_mag) )
                {
                    sk4shot =
                    add_node(tsk->position.x,tsk->position.y,
                    tsk->position.z, 0, sk4shot);
                    shot_count ++;
```

```
                }
                else if( r1 <= (R4[1]*load_mag) && r1
                >= (R4[0]*load_mag) && stage == 2 )
                {
                    sk4shot =
                    add_node(tsk->position.x,tsk->position.y,
                    tsk->position.z, 0, sk4shot);
                    shot_count ++;
                }
            }
            tsk = tsk->next;
        }
    }
/* check all the cross points so that the shots verty close to each
other will be averaged. */
    tsk = sk4shot;
    while(tsk)
    {
        ar = r1 = tsk->thickness;
        ax = x1 = tsk->position.x;
        ay = y1 = tsk->position.y;
        az = z1 = tsk->position.z;
        n = 1;
        compare = tsk->next;
        while(compare)
        {
            tmpc = compare->next;
            x2 = compare->position.x;
            y2 = compare->position.y;
            z2 = compare->position.z;
            r2 = compare->thickness;
            dis = (ax/n-x2)*(ax/n-x2)
            +(ay/n-y2)*(ay/n-y2)+(az/n-z2)*(az/n-z2);
            if( (float)sqrt((double)dis) <=
            (float)(load_mag*RMIN*1.5))
            {
                ax += x2;
                ay += y2;
                az += z2;
                ar += r2;
                n ++;
                sk4shot = delete_node(compare, sk4shot,
                &tmpc);
            }
            compare = tmpc;
        }
        newsk4shot = add_note((ax/n),(ay/n),(az/n),(ar/n), 0,
        newsk4shot);
        sk4shot = delete_node(tsk, sk4shot, &tmpc);
        tsk = tmpc;
    }
    free_list(sk4shot);
    tsk = newsk4shot;
    shot_count =0;
    while(tsk)
    {
        shot_count ++;
/*      fprintf(stderr,"shotsfromcross: (%f %f %f %f)\n",
        tsk->position.x, tsk->position.y, tsk->position.z,
        tsk->thickness); */
        tsk = tsk->next;
    }
    *list = newsk4shot;
    return(shot_count);
}
/*
* calculate possible shots from one end point
*
*
*/
#include "includes.h"
#include "g3dplan_ui.h"
#include "g3dplan.h"
/* global variable */
extern unsigned short  *get_dist_img( );
extern int mag3D( ),get_img_width( ),get_img_height( ),
get_img_height( );
extern SKELETON *delet_node( ), *delete_node( ), *add_node( ),
*get_first_skelet( );
```

```
-continued extern void    free_list( );
extern int     get_load_mag( ),get_stage( );
int shotsfromend(endpoint,skeleton,list)
SHOT    endpoint;
SKELETON   *skeleton, **list;
{
    int  img_width = get_img_width( ),
         img_height = get_img_height( ),
         img_depth = get_img_depth( ),
         load_mag = get_load_mag( ),
         stage = get_stage( );
    unsigned short  *dist_img = get_dist_img( );
    int numonlist =0;
    float dis,x,y,z,r, dd,x1,y1,z1,r1;
    SKELETON *tmp = NULL, *compare = NULL, *tmpc = NULL,
    *tmpt = NULL;
    int row, col, ind;
    int touch2( );
    /* check the input */
    if(skeleton == NULL)
    {
        printf("shotsfromend: NULL skeleton passed \n");
        return(0);
    }
    if(list == NULL)
    {
        printf("shotsfromend: NULL list passed \n");
        return(0);
    }
    r1 = endpoint.r;
    x1 = endpoint.x;
    y1 = endpoint.y;
    z1 = endpoint.z;
    tmp = skeleton;
    numonlist = 0;
    while(tmp != NULL)
    {
        r = tmp->thickness;
        x = tmp->position.x;
        y = tmp->position.y;
        z = tmp->position.z;
        dis = sqrt((double)(x-x)*(x-x1) +(y-y1)*(y-y1)
        +(z-z)*)z-z1)));
        if( (dis - r + endpoint.r) <= (0.8*load_mag) )
        {
            dis += touch2(x,y,z,r) + endpoint,r/2.5;
            if( dis < r)
                dis = r;
            if( dis -> (R18[1]*load_mag) && dis >=
            (R8[0]*load_mag))
            {
                *list = add_node(x, y, z, dis, 0,
                *list);
                numonlist ++;
            }
            else if( dis <= (R4[1]*load_mag) && dis >=
            (R4[0]*load_mag) && stage = 2)
            {
                *list = add_node(x, y, z, dis, 0,
                *list);
                numonlist ++;
            }
        }
        tmp = tmp->next;
    }
/* compress the list that the shots very very close to each other will
not duplicate */
    tmp = *list;
    while(tmp)
    {
        r = tmp->thickness;
        x = tmp->position.x;
        y = tmp->position.y;
        z = tmp->position.z;
        /* check for any of the next shots starting with the
        next node */
        compare = tmp->next;
        while(compare != NULL)
        {
```

```
            /*
             * the "compare" node may be deleted.
             * so save the pointer to next
             */
            tmpc = compare->next;
            x1 = compare->position.x;
            y1 = compare->position.y;
            z1 = compare->position.z;
            r1 = compare->thickness;
            dis = sqrt((double)((x-x1)*(x-x1)
            +(y-y1)*(y-y1)+(z-z1)*(-z1)));
            if( dis <= (float)(load_mag*RMIN*0.5))
            {
                *list = delete_node(compare, (SKELETON
                    *)(*list), &tmpc);
            }
            else if( dis <= (float)(load_mag*RMIN*0.8) &&
            (float)fabs(r1-r) <= (float)(0.3*load_mag))
            {
                *list = delete_node(compare, (SKELETON
                    *)(*list), &tmpc);
            }
            compare = tmpc;
        }
        tmp = tmp->next;
    }
    /* count the total nodes remaining in the list for return */
    tmp = *list;
    numonlist = 0;
    while(tmp)
    {
        numonlist ++;
        tmp = tmp->next;
    }
    return(numonlist);
}
int touch2(xp,yp,zp,r)
float xp, yp,zp,r;
{
    SKELETON  *tmp = NULL;
    SKELETON  *first_skelet = get_first_skelet( );
    int       img_width = get_img_width( ), img_height =
    get_img_height( );
    unsigned short *dist_img = get_dist_img( );
    int load_mag = get_load_mag( );
    float     d,xx,yy,zz;
    int       loc;
    if( !first_skelet)
    {
        fprintf(stderr,"touch2: first skelet is null\n");
        return(0);
    }
    tmp = first_skelet;
    loc = (((int)zp)*img_height +(int)yp)*img_width + (int)xp;
    d = dist_img(loc);
    d -= (r*r);
    if( fabs(d) <= (double)(6.0))
    {
        while(tmp)
        {
            xx = tmp->position.x;
            yy = tmp->position.y;
            zz = tmp->position.z;
            d = (xp-xx)*(xp-xx)+(yp-yy)*(yp-yy) + (zp -
            zz)*(zp-zz);
            if( (float)sqrt(d) <= (0.4*load_mag))
            {
                return(2)
            }
            tmp = tmp->next;
        }
        return(1);
    }
    else
    {
        return(0);
    }
/*
 *
```

```
* button callback routines: show_plan from already know plan
*
*/
#include "includes.h"
#include "g3dplan_ui.h"
#include "g3dplan.h"
/*
 * Global object definitions.
 */
extern void display_status( ), free_list( );
extern int cutimg( );
extern SKELETON *add_node( );
extern g3dplan_main_window_objects *get_main_window_objects( );
extern Display *get_display( );
extern unsigned char *get_img( );
extern char *get_prog_name( );
void
show_plan( )
{
    unsigned char *img = get_img( );
    char *prog_name = get_prog_name( );
    Display *display = get_display( );
    g3dplan_main_window_objects   *G3dplan_main_window =
    get_main_window_objects( );
    int      i;
    char     sbuff[256];
    char     *input = NULL;
    float    x,y,z,r;
    int      count;
    FILE     *fp = NULL;
    SKELETON *sk=NULL, *tmpsk =NULL;
    SHOT     shot;
    fputs("g3dplan: show_plan\n", stderr);
    input = (char *)xv_get(G3dplan_main_window->file_name,
    PANEL_VALUE);
    if ((fp = fopen(input, "r")) == NULL)
    {
        sprintf(sbuff, "%s: can not open file %s to read \n",
        prog_name, input);
        xv_set(G3dplan_main_window->main_window,
        FRAME_LEFT_FOOTER, sbuff, NULL);
        XBell(display, 0);
        return ;
    }
    fscanf(fp,"%s", sbuff);
    fscanf(fp,"%s", sbuff);
    if ( (scanf(fp,"%d", &count) != 1)
    {
        fclose(fp);
        sprintf(sbuff, "%s: can not read file %s\n", prog_name,
        input);
        xv_set(G3dplan_main_window->main_window,
        FRAME_LEFT_FOOTER, sbuff, NULL);
        XBell(display, 0);
        return ;
    }
    for ( i= 0; i < count;i++)
    {
        fscanf(fp,"%s", sbuff);
        fscanf(fp,"%s", sbuff);
        if ( (scanf(fp,"%g", &x) != 1)
        {
            fclose(fp);
            free_list(sk);
            sprintf(sbuff, "%s: can not read file %s\n",
            prog_name, input);
            xv_set(G3dplan_main_window->main_window,
            FRAME_LEFT_FOOTER, sbuff, NULL);
            XBell(display, 0);
            return;
        }
        fscanf(fp,"%s", sbuff);
        if ( (scanf(fp, "%g", &y) != 1)
        {
            fclose(fp);
            free_list(sk);
            sprintf(sbuff, "%s: can not read file %s\n",
            prog_name, input);
            xv_set(G3dplan_main_window->main_window,
```

-continued

```
                FRAME_LEFT_FOOTER, sbuff, NULL);
            XBell(display, 0);
            return;
        }
        fscanf(fp,"%s", sbuff);
        if ( fscanf(fp,"%g", &z) != 1)
        {
            fclose(fp);
            free_list(sk);
            sprintf(sbuff, "%s: can not read file %s\n",
                prog_name, input);
            xv_set(G3dplan_main_window->main_window,
                FRAME_LEFT_FOOTER, sbuff, NULL);
            XBell(display, 0);
            return;
        }
        fscanf(fp,"%s", sbuff);
        if ( fscanf(fp,"%g", &r) != 1)
        {
            fclose(fp);
            free_list(sk);
            sprintf(sbuff, "%s: can not read file %s\n",
                prog_name, input);
            xv_set(G3dplan_main_window->main_window,
                FRAME_LEFT_FOOTER, sbuff, NULL);
            XBell(display, 0);
            return;
        }
        sk = add_node(x,y,z,r, 0, sk);
    }
    fclose(fp);
    /*
     * done reading plan file . . .
     */
    tmpsk = sk;
    while (tmpsk != NULL)
    {
        shot.x = tmpsk->position.x;
        shot.y = tmpsk->position.y;
        shot.z = tmpsk->position.z;
        shot.r = tmpsk->thickness;
        cutimg(img, shot);
        tmpsk = tmpsk->next;
    }
    xv_set(G3dplan_main_window->main_window,
        FRAME_LEFT_FOOTER, "", NULL);
    display_status(DISPLAY_ALL, 1, img, sk);
    return;
}
/*
 * processing routines for g3dplan:
 * make_skeleton
 * add_shots
 *
 */
#include "includes.h"
#include "g3dplan_ui.h"
#include "g3dplan.h"
extern g3dplan_main_window_objects *get_main_window_objects( );
extern char *get_prog_name( );
extern CONTOUR    get_contour( );
extern int        get_img_width( ), get_img_height( ),
                  get_img_depth( );
/* range of the image */
extern int mag3D( );
extern void GFree( );
extern int get_current_slice( );
extern void set_current_slice( );
extern ILIST *atoil(char *);
extern void FreeIlist(ILIST *);
extern SKELETON *add_node( );
extern void set_first_skelet( ), set_tmp_skelet( );
extern SKELETON *copylist( );
extern SKELETON *get_tmp_skelet( );
extern SKELETON *delete_node( );
/* X display variables */
extern Visual *get_visual( );
extern Display *get_display( );
extern Colormap get_colormap( );
```

-continued

```
extern Window   get_paint_window( ), get_sub_paint_window( );
extern GC   get_gc( ), get_sub_gc( );
extern unsigned long get_black_pixel( ), get_white_pixel( ),
get_red_pixel( ),
                get_yellow_pixel( ), get_green_pixel( ),
                get_gray_start_pixel( );
extern int    set_canvas_width( ), set_canvas_height( ),
              set_sub_canvas_height( ), set_sub_canvas_width( );
extern int    get_depth( );
extern unsigned char *get_img( );
extern unsigned char *get_tmp_img( );
extern unsigned short *get_dist_img( );
extern void set_temp_img( );
extern SKELETON *get_first_skelet( );
extern int    get_load_mag( );
extern void   display_array(int, int *, unsigned char *, SKELETON *);
extern void   display_status(int, . . . );
void make_skeleton( )
{
    g3dplan_window_array_objects    *get_window_array_pointer( );
    g3dplan_main_window_objects    *main_win =
    get_main_window)objects( );
    g3plan_window_array_objects    *array =
    get_window_array_pointer( );
    int slice = get_current_slice( );
    int img_depth = get_img_depth( ),
    img_width = get_img_width( ),
    img_height = get_img_height( );
    int disp_type;
    int count, i;
    unsigned char *img = get_img( ), *tmp_img = NULL;
    SKELETON *first_skelet = get_first_skelet( );
    SKELETON *tmp_skelet = get_tmp_skelet( );
    Display *display = get_display( );
    char * str = NULL;
    ILIST *list = NULL;
    int *index = NULL;
    SKELETON *tmp = NULL,*sk= NULL, *end = NULL,
    *cross = NULL, *compress( );
    if(img == NULL)
        return;
    if( tmp_img == NULL)
    {
        tmp_img = (unsigned char
        *)calloc(img_height*img_width*img_depth,
        sizeof(unsigned char));
        if( !tmp_img)
        {
            fprintf(stderr,"skel: cannot allocate memory
            for images\n");
            exit(1);
        }
        set_tmp_img(tmp_img);
        (void)
        mag3D(img,img_width,img_height,img_depth,tmp_img,
        1,1,1);
    }
    else
    {
        (void)
        mag3D(tmp_img,img_width,img_height,img_depth,img,
        1,1,1);
    }
    free_list(tmp_skelet);
    tmp_skelet = NULL;
    set_tmp_skelet(tmp_skelet);
    tmp_skelet = copylist(first_skelet);
    set_tmp_skelet(tmp_skelet);
    (void)edtsk3d(tmp_img, &end, &cross, &sk);
    cross = compress(cross);
    end = compress(end);
    display_status2(DISPLAY_IMAGE,tmp_img);
    tmp = end;
    printf("end . . . ");
    printf("\n");
    while(tmp)
    {
        printf(*(%g %g %g %g) *, tmp->position.x,
        tmp->position.y, tmp->position.z, tmp->thickness);
```

```
            tmp=tmp->next;
        }
        printf("\n");
        tmp = cross;
        printf("cross . . . ");
        printf("\n");
        while(tmp)
        {
            printf(*(%g %g %g %g) *; tmp->position.x,
            tmp->position.y, tmp->position.z, tmp->thickness);
            tmp=tmp->next;
        }
        printf("\n");
        printf(" . . . skeleton . . . ");
        printf("\n");
        free_list(sk);
        free_list(end);
        free_list(cross);
        return;
}
SKELETON *compress(skelet)
SKELETON *skelet;
{
    float ax, ay,ax,ar;
    int n;
    float dis, x1,y1,z1,x2,y2,z2,r1,r2;
    SKELETON *tsk = NULL, *compare = NULL, *tmpc= NULL;
    SKELETON *newsk = NULL;
    tsk = skelet;
    while(tsk)
    {
        ar = r1 = tsk->thickness;
        ax = x1 = tsk->position.x;
        ay = y1 = tsk->position.y;
        az = z1 = tsk->position.z;
        n = 1;
        compare = tsk->next;
        while(compare)
        {
            tmpc = compare->next;
            x2 = compare->position.x;
            y2 = compare->position.y;
            z2 = compare->position.z;
            r2 = compare->thickness;
            dis = (zx/n-x2)*(ax/n-x2)
            +(lay/n-y2)*(ay/n-y2)+(az/n-z2)*(az/n-z2);
            if( (float)(dis) <= (float)(d))
            {
                ax += x2;
                ay += y2;
                az += z2;
                if( r2 > ar) ar = r2;
                n ++;
                skelet = delete_node(compare, skelet,
                &tmpc);
            }
            compare = tmpc;
        }
        newsk= add_node((ax/n),(ay/n),(az/n),ar, 0, newsk);
        skelet = delete_node(tsk, skelet, &tmpc);
        tsk = tmpc;
    }
    free_list(skelet);
    return(newsk);
}
void add_shots( )
{
    g3dplan_window_array_objects    *get_window_array_pointer( );
    g3dplan_main_window_objects     *main_win =
    get_main_window_objects( );
    g3dplan_window_array_objects    *array =
    get_window_array_pointer( );
    g3dplan_main_window_objects *G3dplan_main_window =
    get_main_window_objects( );
    int slice = get_current_slice( );
    int disp_type;
    int count, i;
    unsigned char *img = get_img( ), *tmp_img = get_tmp_img( );
    SKELETON *first_skelet = get_first_skelet( );
```

```
        Display *display = get_display( );
        char * str = NULL;
        ILIST *list = NULL;
        int *index = NULL;
        unsigned short *dist_img = get_dist_img( );
        int img_width = get_img_width( ),
        img_height = get_img_height( ),
        img_depth = get_img_depth( );
        SHOT   shot;
        int helmet;
        SKELETON *tmp_skelet = get_tmp_skelet( );
        fputs("add_shots: add_shots & planning\n", stderr);
        /*
        if(dist_img == NULL)
        {
                dist_img = (unsigned short *)
                calloc(img_width*img_height*img_depth; sizeof(short));
                if(dist_img == NULL)
                {
                        fprintf(stderr,"add_shots . . . No memory
                        available :(\n");
                        return;
                }
                if( !sedt(img, dist_img))
                {
                        fprintf(stderr,"add_shots . . . No memory available
                        \n");
                        return;
                }
                set_dist_img(dist_img);
        }
        */
        if( img == NULL || tmp_img == NULL)
        {
                fprintf(stderr,"add_shots . . . img or tmp_img
                isn't there \n");
                return;
        }
        (void) mag3D(tmp_img,img_width,img_height,img_depth,img,
        1,1,1);
        shot.x = (float) atof((char *)xv_get(G3dplan_main_window->x,
        PANEL_VALUE));
        shot.y = (float) atof((char *)xv_get(G3dplan_main_window->y,
        PANEL_VALUE));
        shot.z = (float) atof((char *)xv_get(G3dplan_main_window->z,
        PANEL_VALUE));
        shot.r = (float) atof((char *)xv_get(G3dplan_main_window->r,
        PANEL_VALUE));
        helmet = (int) atoi((char *)xv_get(G3dplan_main_window->
        helmet, PANEL_VALUE));
        cutimg2(tmp_img,shot,helmet);
        free_list(tmp_skelet);
        tmp_skelet = NULL;
        set_tmp_skelet(tmp_skelet);
        tmp_skelet = copylist(first_skelet);
        set_tmp_skelet(tmp_skelet);
        first_skelet = add_node(shot.x, shot.y, shot.z, shot.r, helmet,
        first_skelet);
        set_first_skelet(first_skelet);
        display_status2(DISPLAY_ALL,tmp_img, first_skelet);
        return;
}
void cancel_last_shot( )
{
        SKELETON *tmp_skelet = get_tmp_skelet( );
        SKELETON *first_skelet = get_first_skelet( );
        unsigned char *img = get_img( ), *tmp_img = get_tmp_img( );
        int img_width = get_img_width( ),
        img_height = get_img_height( );
        img_depth = get_img_depth( );
        (void) mag3D(img, img_width, img_height, img_depth, tmp_img,
        1,1,1);
        free_list(first_skelet);
        first_skelet = NULL;
        set_first_skelet(first_skelet);
        first_skelet = copylist(tmp_skelet);
        set_first_skelet(first_skelet);
        display_status2(DISPLAY_ALL, img, first_skelet);
}
SKELETON *copylist(list)
```

-continued

```c
SKELETON *list;
{
    SKELETON *new=NULL;
    if(!list)
        return(list);
    while(list->prev)
        list = list->prev;
    while(list)
    {
        new = add_node(list->position).x, (list->position).y,
              (list->position).z, list->thickness ,
              list ->helmet,new)
        list = list->next;
    }
    return(new);
}
/*
 * steped thining routines for g3dplan;
 *
 * button callback routines
 *
 */
#include "includes.h"
#include "g3dplan_ui.h"
#include "g3dplan.h"
/*
 * Global object definitions.
 */
extern void display_status( );
extern int mag3D( );
/* global variable */
extern int      calc_shots( ), shotsfromend( );
extern void     recur_search( );
extern void     recur_delete( );
extern int      init_dist_3dimg( ), recur_match_mode( );
extern SKELETON *delet_node( ), *add_node( );
extern void     free_list( ), edsk3d( );
extern unsigned short  *get_dist_img( );
extern unsigned char   *get_img( );
extern void     set_dist_img(unsigned short *);
extern void     set_first_skelet(SKELETON *), set_stage(int);
extern int      get_img_width( ),get_img_height( ), get_img_depth( ),
get_load_mag( ), get_stage( );
extern SKELETON *get_first_skelet( );
extern int      sedt( );
void
step_thru( )
{
    unsigned short  *dist_img = get_dist_img( );
    unsigned char *img = get_img( );
    int       img_width = get_img_width( ),
              img_height = get_img_height( ),
              img_depth = get_img_depth( ),
              stage = get_stage( ),
              load_mag = get_load_mag( );
    SKELETON *first_skelet = get_first_skelet( );
    TREE      plantree;
    SHOT      endpt;
    int       filenum=0;
    int       i, j, found, num_shots=0;
    unsigned char   *buf = NULL;
    SKELETON  *ends = NULL, *sks = NULL, *crosses = NULL,
    *tmp = NULL, *newlist = NULL;
    fprintf(stderr, "step_thru . . . \n");
    plantree.shot.x=9999.0;
    plantree.shot.y=9999.0;
    plantree.shot.z=9999.0;
    plantree.shot.r=0.0;
    plantree.prev=NULL;
    plantree.next_count = 0;
    stage = 1;
    free_list(first_skelet);
    set_first_skelet(NULL);
    first_skelet = NULL;
    GFree(dist_img);
    dist_img = NULL;
    set_dist_img(NULL);
    dist_img = (unsigned short *)
    calloc(img_width*img_height*img_depth, sizeof(short));
```

-continued

```
if(dist_img == NULL)
{
    fprintf(stderr,"step_thru . . . No memory available
    :(\n");
    return;
}
buf = (unsigned char *) calloc(img_width*img_height*img_depth,
sizeof(char));
if(buff == NULL)
{
    fprintf(stderr,"step_thru . . . No memory available
    :(\n");
    GFree(dist_img);
    return;
}
if(mag3D(img, img_width, img_height, img_depth, buf, 1,1,1) !=
(img_width*img_height*img_depth))
{
    fprintf(stderr,"step_thru . . . mag3D failed :(\n");
    GFree(buf);
    GFree(dist_img);
    GFree(img);
    return;
}
if( !sedt(buf, dist_img))
{
    fprintf(stderr,"step_thru . . . No memory available \n");
    return;
}
set_dist_img(dist_img);
edtsk3d(buf, &ends, &crosses, &sks);
GFree(buf);
set_first_skelet(sks);
if(ends == NULL)
{
    fprintf(stderr, "step_thru, get empty endlist here\n");
    free_list(sks);
    free_list(crosses);
    return;
}
if( crosses)
{
    fprintf(stderr,"step_thru . . . getting shots form
    crosses\n");
    num_shots = shotsfromcross(crosses, &newlist);
    free_list(crosses);
    crosses = NULL;
}
/*
tmp = ends;
while(tmp != NULL)
{
    fprintf(stderr,"step_thru . . . getting shots from
    ends\n");
    endpt.x= tmp->position.x;
    endpt.y= tmp->position.y;
    endpt.z= tmp->position.z;
    endpt.r= tmp->thickness;
    num_shots = shotsfromend(endpt, sks, *newlist);
    tmp = tmp->next;
}
*/
free_list(ends);
ends=NULL;
/*
free_list(sks);
sks=NULL;
*/
printf("steps_thru: first shots combination: %d\n", num_shots);
display_status(DISPLAY_SKELETON, newlist);
plantree.next_count = num_shots;
plantree.next = (TREE **)calloc(num_shots, sizeof(TREE *));
if(plantree.next == NULL)
```

```
{
    printf("step_thru: cannot allocate the memory for shots
    \n");
    exit(1);
}
tmp = newlist;
for(i=0;i<num_shots;i++)
{
    plantree.next[i] = (TREE *)calloc(1, sizeof(TREE));
    if(plantree.next[i] == NULL)
    {
        printf("step_thru: cannot allocate the memory
        for shots \n");
        exit(1);
    }
    ((plantree.next[i])->shot).x = tmp->position.x;
    ((plantree.next[i])->shot).y = tmp->position.y;
    ((plantree.next[i])->shot).z = tmp->position.z;
    ((plantree.next[i])->shot).r = tmp->thickness;
    (plantree.next[i])->prev = &plantree;
    (plantree.next[i])->next = NULL;
    (plantree.next[i])->next_count = 0;
    tmp = tmp->next;
}
free_list(newlist); newlist = NULL;
for(i=0;i<plantree.next_count;i++)
{
    found = 0;
    for(j =0; j < i;j++)
    {
        found = recur_match_node(plantree.next[j],
        plantree.next[i]);
        if (found) break;
    }
    if( !found )
        recur_search(plantree.next[i], &filenum, 1);
}
for(i=0;i<plantree.next_count;i++)
    recur_delete(plantree.next[i]);
GFree(plantree.next);
first_skelet = get_first_skelet( );
free_list(first_skelet); set_first_skelet(NULL);
GFree(dist_img); set_dist_img(NULL);
GFree(img); set_img(NULL);
return;
}
int recur_match_node(branch, node)
TREE *branch;
SHOT *node;
{
    int match = 0;
    int i;
    double dist, node_distance( );
    int load_mag = get_load_mag( );
    if(!branch || !node)
        return (0);
    if(branch->next_count == 0)
        return (0);
    for(i=0;i<branch->next_count;i++)
    {
        dist = node_distance((branch->next[i])->shot, *node);
        if( dist < (double)3*load_mag)
        {
            match = 1;
            break;
        }
    }
    if(match)
        return (match);
    else
    {
        for(i=0;i<branch->next_count;i++)
        {
            match = recur_match_node(branch->next[i],
            node);
            if(match)
                break;
        }
    }
```

```
        return (match);
}
double node_distance(node1, node2)
SHOT node1, node2,
{
        double dist, dx, dy, dz;
        dx = (node1.x − node2.x);
        dx = dx*dx;
        dy = (node1.y − node2.y);
        dy = dy*dy;
        dz = (node1.z − node2.z);
        dz = dz*dz;
        dist = sqrt(dx + dy + dz);
        return (dist);
}
void recur_delet(tree_node)
TREE *tree_node;
{
        int i;
        TREE *tptr;
        if(tree_node == NULL)
        {
                fprintf(stderr,"recur_delete( ): NULL tree passed\n");
                return;
        }
        if(tree_node->next_count > 0 && tree_node->next != NULL)
        {
                for(i=0;i<tree_node->next_count;i++)
                {
                        tptr = tree_node->next[i];
                        if(tptr != NULL)
                                recur_delet(tptr);
                }
        }
        GFree(tree_node);
        return;
}
/*
 * processing routines for g3dplan:
 * thining.c
 *
 * button callback routines
 *
 */
#include "includes.h"
#include "g3dplan_ui.h"
#include "g3dplan.h"
/*
 * external function definitions.
 */
extern void display_status( );
extern SKELETON *get_first_skelet( );
extern void   free_list( );
extern unsigned char   *get_img( );
extern void set_img(unsigned char *);
extern void set_first_skelet(SKELETON *);
void
thining( )
{
        SKELETON *first_skelet = get_first_skelet( );
        unsigned char   *img = get_img( );
        SKELETON *tmp = NULL,*sk= NULL, *end = NULL,
        *cross = NULL;
        if(img == NULL)
                return;
        (void)edtsk3d(img, &end, &cross, &sk);
        display_status(DISPLAY_IMAGE,img);
/*
        tmp = sk;
        printf("sk . . . ");
        while(tmp)
        {
                printf(*(%g %g %g) *, tmp->position.x, tmp->position.y,
                tmp->position.z);
                tmp=tmp->next;
        }
        printf("\n");
        tmp = end;
        printf("end . . . ");
```

```
        while(tmp)
        {
            printf(*(%g %g %g) *, tmp->position.x, tmp->position.y,
            tmp->position.z);
            tmp=tmp->next;
        }
        printf("\n");
        tmp = cross;
        printf("cross . . . ");
        while(tmp)
        {
            printf(*(%g %g %g) *, tmp->position.x, tmp->position.y,
            tmp->position.z);
            tmp=tmp->next;
        }
        printf("\n");
        */
}
/* >>>>>>>>>>>>>>>>>>>>>>>> <<<<<<<<<<<<<<<<<<<<<<
    >>>>
    >>>>    library function to compute transformation
    >>>>        matrix
    >>>>
    >>>>>>>>>>>>>>>>>>>>>>>> <<<<<<<<<<<<<<<<<<<<<< */
#include "includes.h"
#include "g3dplan.h"
#define Epsilon 1E-05
#define PI 3.1415927
matrix M;
void midentM( ), rotate(float, char), translate(float,float,float),
print_matrix( );
void get_view(float *v, float *u, float x, float y, float z)
{
    *v = M[0][0]*x + M[1][0]*y + M[2][0]*x + M[3][0];
    *u = M[0][1]*x + M[1][1]*y + M[2][1]*z + M[3][1];
    return;
}
void tr_matrix(float alpha, float beta, float gamma, float x,
float y, float z)
{
    (void) midentM( );
    (void) rotate(alpha, 'x');
    (void) rotate(beta, 'y');
    (void) rotate(gamma, 'z');
    (void) translate(x,y,z);
}
/*
 * mcpy4
 *
 *    copies 4 by 4 matrix m2 int m1
 */
void
mcpyr(matrix m1, matrix m2)
{
    int i, j;
    for(i=0;i<4;i++)
        for(j=0;j<4;j++)
            m1[i][j] = m2[i][j];
}
void
mcpyM(matrix m)
{
    int i, j;
    for(i=0;i<4;i++)
        for(j=0;j<4;j++)
            M[i][j] = m[i][j];
}
/*
 * midentM
 *
 *    set m to a 4 by 4 identity matrix
 */
void
midentM( )
{
    int i, j;
    for(i=0;i<4;i++)
        for(j=0;j<4;j++)
            M[i][j] = 0.0;
```

-continued

```
        M[0][0] = M[1][1] = M[2][2] = M[3][3] = 1.0;
}
/*
/*
 * mmult4
 *
 *     multiplies four by four matrix m3 by m2, leaving result in
 * m1.
 *
 */
void
midentM(matrix m2, matrix m3)
{
    M[0][0] = m2[0][0] * m3[0][0] + m2[0][1] * m3[1][0] + m2[0][2]
        * m3[2][0] + m2[0][3] * m3[3][0];
    M[0][1] = m2[0][0] * m3[0][1] + m2[0][1] * m3[1][1] + m2[0][2]
        * m3[2][1] + m2[0][3] * m3[3][1];
    M[0][2] = m2[0][0] * m3[0][2] + m2[0][1] * m3[1][2] + m2[0][2]
        * m3[2][2] + m2[0][3] * m3[3][2];
    M[0][3] = m2[0][0] * m3[0][3] + m2[0][1] * m3[1][3] + m2[0][2]
        * m3[2][3] + m2[0][3] * m3[3][3];
    M[1][1] = m2[1][0] * m3[0][0] + m2[1][1] * m3[1][3] + m2[1][2]
        * m3[2][0] + m2[1][3] * m3[3][0];
    M[1][1] = m2[1][0] * m3[0][1] + m2[1][1] * m3[1][1] + m2[1][2]
        * m3[2][1] + m2[1][3] * m3[3][1];
    M[1][2] = m2[1][0] * m3[0[[2] + m2[1][1] * m3[1][2] + m2[1][3]
        * m3[2][2] + m2[1][3] * m3[3][2];
    M[1][3] = m2[1][0] * m3[0][3] + m2[1][1] * m3[1][3] + m2[1][2]
        * m3[2][3] + m2[1][3] * m3[3][3];
    M[2][0] = m2[2][0] * m3[0][0] + m2[2][1] * m3[1][0] + m2[2][2]
        * m3[2][0] + m2[2][3] * m3[3][0];
    M[2][1] = m2[2][0] * m3[0][1] + m2[2][1] * m3[1][1] + m2[2][2]
        * m3[2][1] + m2[2][3] * m3[3][1];
    M[2][2] = m2[2][0] * m3[0][2 + m2[2][1] * m3[1][2] + M2[2][2]
        * m3[2][2] + m2[2][3] * m3[3][2];
    M[2][3] = m2[2][0] * m3[0][3] + m2[2][1] * m3[1][3] + m2[2][2]
        * m3[2][3] + m2[2][3] * m3[3][3];
    M[3][0] = m2[3][0] * m3[0][0] + m2[3][1] * m3[1][0] + m2[3][2]
        * m3[2][0[ + m2[3][3] * m3[3][0];
    M[3][1] = m2[3][0] * m3[0][1] + m2[3][1] * m3[1][1] + m2[3][2]
        * m3[2][1[ + m2[3][3] * m3[3][1];
    M[3][2] = m2[3][0] * m3[0][2] + m2[3][1] * m3[1][2] + m2[3][2]
        * m3[2][2[ + m2[3][3] * m3[3][2];
    M[3][3] = m2[3][0] * m3[0][3] + m2[3][1] * m3[1][3] + m2[3][2]
        * m3[2][3[ + m2[3][3] * m3[3][3];
}
/*
 * rotate
 *
 *     adjust the transformation matrix for a rotate - done in reverse
 * as it is done to the ray.
 */
void
rotate(float ang, char axis)
{
    int i, j;
    martix   mat, tmp;
    float    sinval, cosval;
    for(i=0;i<4;i++)
        for(j=0;j<4;j++)
            mat[i][j] = 0.0;
    mat[0][0] = mat[1][1] = mat[2][2] = mat[3][3] = 1.0;
    sinval = sin((double)(ang * PI / 180.0));
    cosval = cos((double)(ang * PI / 180.0));
    siwtch (axis) {
    case 'x':
        mat[1][1] = cosval;
        mat[1][2] = sinval;
        mat[2][2] = cosval;
        mat[2][1] = -sinval;
        break;
    case 'y':
        mat[0][0] = cosval;
        mat[0][2] = -sinval;
        mat[2][0] = sinval;
        mat[2][2] = cosval;
        break;
    case 'z':
        mat[0][0] = cosval;
```

-continued

```
            mat[0][1] = sinval;
            mat[1][0] = -sinval;
            mat[1][1] = cosval;
            break;
        }
        for(i=0;i<4;i++)
            for(j=0;j<4;j++)
                tmp[i][j] = M[i][j];
        mmultM(mat, tmp);
}
/*
 * translate
 *
 *   translate - negative as we do this to the ray.
 */
void
translate(float x,float y,float z)
{
    int i,j;
    matrix mat, tmp;
    for(i=0;i<4;i++)
        for(j=0;j<4;j++)
            mat[i][j] = 0.0;
    mat[0][0] = mat[1][1] = mat[2][2] = mat[3][3] = 1.0;
    mat[3][0] = x;
    mat[3][1] = y;
    mat[3][2] = z;
    for(i=0;i<4;i++)
        for(j=0;j<4;j++)
            tmp[i][j] = M[i][j];
    mmultM(mat, tmp);
}
/*
 * transform
 *
 *   apply the transformation matrix m to the matrix stack.
 */
void
transform(matrix m)
{
    matrix   tmp;
    float    x, y, z;
    /*
     * multiply stack
     */
    mcpyM(tmp)
    mmultM(m, tmp);
}
void
print_matrix( )
{
    int i,j;
    printf("Matrix M:\n");
    for(i=0;i<4;i++)
    {
        for(j=0;j<4;j++)
            printf(" %10g", M[i][j]);
        printf("\n");
    }
}
```

What is claimed is:

1. A method for planning radiotherapy treatment comprising the steps of:
   a) determining a first target region of a patient and locating a medial axis of a first target region of a patient;
   b) initializing a plan for the distribution of a plurality of spherical distributions of radiation by identifying endpoints of the medial axis and determining a virtual shot for each endpoint of each plan;
   c) providing additional virtual shots for each plan by excluding portions of said target region which are already covered by any virtual shot which has already been determined;
   d) determining a medial axis for a modified target region which is established by excluding regions from said first target region which would be covered by any virtual shot which has already been determined;
   e) placing additional virtual shots at endpoints or cross points of said medial axis for said modified target region to generate a distribution plan for targeting shots of radiation.

2. The method of claim 1 wherein steps c), d) and e) are repeated.

3. The method of claim 1 wherein steps c), d) and e) are repeated until a therapeutically acceptable portion of said first target region is covered by virtual shots.

4. The method of claim 3 wherein each virtual shot has a virtual size which is determined as dimensions of each said virtual shot where dose levels at a focal plain decrease from a predetermined percentage of a dose level which exists within said virtual shot.

5. The method of claim 3 wherein said dose level which exists within said virtual shot is assigned a value, and said predetermined percentage is less than 80%.

6. The method of claim 4 wherein said dose level which exists within said virtual shot is assigned a value, and said predetermined percentage is less than 65% and greater than 25%.

7. The method of claim 4 wherein said dose level which exists within said virtual shot is assigned a value, and said predetermined percentage is less than 65% and greater than 40%.

8. The method of claim 1 wherein said distribution plan is used to direct a radiation emitting device which can be used to provide a spherical distribution of radiation to position actual distributions of radiation according to said distribution plan.

9. The method of claim 8 wherein said radiation emitting device is selected from gamma emitting devices, linear accelerators, and Brachy therapy sources.

10. The method of claim 9 wherein said radiation emitting device is selected from the group consisting of gamma radiation emitting devices and linear accelerators.

11. The method of claim 8 wherein said distribution plans distributes radiation at a therapeutically effective dose level over at least 85% of said first target region.

12. The method of claim 11 wherein said therapeutically effective dose level is at least 40% of the highest single dose radiation level within any shot.

13. A method for planning and executing radiotherapy treatment comprising the steps of
   (a) taking a non-invasive pictorial representation of a first target region of a volume portion of a patient which is to be treated by radiation therapy;
   (b) locating a medial axis within the pictorial representation of the first target region of the patient;
   (c) calculating from said pictorial representation a plan for the distribution of a plurality of spherical distributions of radiation by identifying endpoints of the medial axis and determining a virtual shot for each endpoint of each plan, said virtual shot at each endpoint having its assumed outer limits defined by a percentage of a therapeutically effective level of radiation which is provided in said virtual shot, the assumed outer limits of each virtual shot extending to at least two edges of the target region, said virtual shots at the endpoints virtually covering a part of the volume portion of the patient, and leaving a virtual untreated portion of said volume where minimally desired therapeutic levels of radiation have not yet been applied, the volume of said target area where minimally desired therapeutic levels of radiation have not yet been applied by virtual shots at the endpoints defining a modified target area;
   (d) providing additional virtual shots for each plan within said virtual untreated portion of said volume by determining a modified medial axis for the modified target region which has been established;
   (e) placing additional virtual shots at endpoints or cross points of said modified medial axis for said modified target region to generate a distribution plan for targeting shots of radiation comprising both the virtual shots at the endpoints of the medial axis and the virtual shots placed on said modified medial axis; and
   (f) directing actual radiation treatment using said distribution plan for targeting shots of radiation.

14. The method of claim 13 performed by repeating steps c), d) and e), until a therapeutically acceptable portion of at least 60% of said first target region is covered by virtual shots.

15. The method of claim 13 wherein said distribution plan is used to direct a radiation emitting device which can be used to provide a spherical distribution of radiation to position actual distributions of radiation according to said distribution plan.

16. The method of claim 15 wherein said radiation emitting device is selected from gamma emitting device, linear accelerators, and Brachy therapy sources.

17. The method of claim 15 wherein said radiation emitting device is selected from the group consisting of gamma radiation emitting devices and linear accelerators.

18. The method of claim 15 wherein said distribution plans distributes radiation at a therapeutically effective dose level over at least 85% of said first target region.

19. The method of claim 18 wherein said therapeutically effective dose level is at least 40% of the highest single dose radiation level within any shot.

20. A system for planning and executing radiotherapy treatment comprising:
   a) means for locating a medial axis of a first target region of a patient;
   b) means for initializing a plan for the distribution of a plurality of spherical distributions of radiation by identifying endpoints of the medial axis and determining a virtual shot for each endpoint of each plan;
   c) means for providing additional virtual shots for each plan by excluding portions of said target region which are already covered by any virtual shot which has already been determined;
   d) means for determining a medial axis for a modified target region which is established by excluding regions from said first target region which would be covered by any virtual shot which has already been determined;
   e) means for placing additional virtual shots at endpoints or cross points of said medial axis for said modified target region to generate a distribution plan for targeting shots of radiation; and
   f) means for directing actual radiation treatment using said distribution plan for targeting shots of radiation.

* * * * *

UNITED STATES PATENT AND TRADEMARK OFFICE
CERTIFICATE OF CORRECTION

PATENT NO. : 6,201,988 B1
DATED : March 13, 2001
INVENTOR(S) : Bourland et al.

It is certified that error appears in the above-identified patent and that said Letters Patent is hereby corrected as shown below:

Title page,
Inventors, delete "Oing R. Wu, Westlake, OH (US)" and insert -- Qing R. Wu, Henderson, NV (US) --, therefore.

Claim 1,
Line 3, delete "determining a first target region of a patient and", therefore.

Claim 5,
Line 2, delete "value" and insert -- predetermined percentage value --, therefore.

Claim 6,
Line 2, delete "value" and insert -- predetermined percentage value --, therefore.

Claim 7,
Line 2, delete "value" and insert -- predetermined percentage value --, therefore.

Claim 13,
Delete "(f) directing actual radiation treatment using said distribution plan plan for targeting shots of radiation.", therefore.

Claim 13, section (e),
Line 6, delete "axis; and" and insert -- axis. --, therefore.

Signed and Sealed this

Nineteenth Day of February, 2002

Attest:

JAMES E. ROGAN
Director of the United States Patent and Trademark Office

Attesting Officer